US012778450B2

(12) United States Patent
Blades et al.

(10) Patent No.: US 12,778,450 B2
(45) Date of Patent: Nov. 3, 2026

(54) SYSTEM AND METHOD FOR ANALYZING FORCE SENSOR DATA

(71) Applicant: Orpyx Medical Technologies Inc., Calgary (CA)

(72) Inventors: Samuel Carl William Blades, Victoria (CA); Eric Christian Honert, Calgary (CA); Marc Drew Klimstra, Victoria (CA)

(73) Assignee: ORPYX MEDICAL TECHNOLOGIES INC., Calgary (CA)

( * ) Notice: Subject to any disclaimer, the term of this patent is extended or adjusted under 35 U.S.C. 154(b) by 734 days.

(21) Appl. No.: 17/991,501

(22) Filed: Nov. 21, 2022

(65) Prior Publication Data

US 2023/0165484 A1 Jun. 1, 2023

Related U.S. Application Data

(60) Provisional application No. 63/315,847, filed on Mar. 2, 2022, provisional application No. 63/291,424, filed
(Continued)

(30) Foreign Application Priority Data

Sep. 27, 2022 (CA) .................................... 3176028

(51) Int. Cl.
*A61B 5/103* (2006.01)
*A43B 3/34* (2022.01)

(52) U.S. Cl.
CPC ................ *A61B 5/103* (2013.01); *A43B 3/34* (2022.01)

(58) Field of Classification Search
None
See application file for complete search history.

(56) References Cited

U.S. PATENT DOCUMENTS 6,183,425 B1 2/2001 Whalen et al.
9,072,463 B2 7/2015 Sanders et al.
(Continued)

FOREIGN PATENT DOCUMENTS

CA 2312640 A1 * 1/2001 ............. G01P 15/18
CN 105708469 * 6/2016
(Continued)

OTHER PUBLICATIONS

Machine Translation of LU 101071, Patent Translate, pp. 1-16, printed on Jul. 21, 2025, (Year: 2020).*
(Continued)

*Primary Examiner* — Jennifer Robertson
*Assistant Examiner* — Om Patel
(74) *Attorney, Agent, or Firm* — ABM INTELLECTUAL PROPERTY INC.; Adrienne Bieber McNeil

(57) ABSTRACT

A system, method, and computer program product for analyzing force sensor data is provided. Force sensor data collected from a plurality of force sensors positioned underfoot is analyzed to detect foot contact events and/or a foot contact period. Foot contact and/or foot off can be detected based on inflection points identified in the force signal data received from the plurality of sensors. Identifying foot contact events by detecting inflection points in the force sensor data can increase the sensitivity of detecting both foot contact and foot off. The use of inflection points also allows both foot contact and foot off to be identified even when these foot contact events occur at different force signal heights. Methods for determining ground reaction force data and correcting the magnitude of ground reaction force signals are also provided.

18 Claims, 18 Drawing Sheets

Related U.S. Application Data on Dec. 19, 2021, provisional application No. 63/282,234, filed on Nov. 23, 2021.

(56) References Cited

U.S. PATENT DOCUMENTS

| | | | | |
|---|---|---|---|---|
| 10,004,946 | B2 | 6/2018 | Ross | |
| 10,194,837 | B2 | 2/2019 | Kanchan et al. | |
| 10,213,647 | B2 | 2/2019 | Balakrishnan et al. | |
| 10,405,779 | B2 | 9/2019 | Merrell et al. | |
| 10,531,798 | B2 | 1/2020 | Schneider et al. | |
| 11,064,768 | B2 | 7/2021 | Walker et al. | |
| 2007/0197274 | A1 | 8/2007 | Dugan | |
| 2014/0013862 | A1 | 1/2014 | Lind | |
| 2014/0066816 | A1* | 3/2014 | McNames | A61B 5/6831 600/595 |
| 2015/0065893 | A1* | 3/2015 | Ye | A61B 5/0205 600/595 |
| 2018/0046215 | A1 | 2/2018 | Gosieski, Jr. et al. | |
| 2019/0208865 | A1 | 7/2019 | Walker et al. | |
| 2020/0000373 | A1 | 1/2020 | Agrawal et al. | |
| 2020/0218974 | A1 | 7/2020 | Cheng et al. | |

FOREIGN PATENT DOCUMENTS

| | | | | | |
|---|---|---|---|---|---|
| EP | 1163492 | B1 | | 10/2008 | |
| EP | 2335510 | A1 | | 6/2011 | |
| EP | 2241209 | B1 | | 3/2019 | |
| EP | 3714785 | A1 | | 9/2020 | |
| KR | 102095439 | B1 | | 4/2020 | |
| KR | 102116802 | B1 | | 6/2020 | |
| LU | 101071 | B1 | * | 6/2020 | A61B 5/6807 |
| WO | WO-2009152456 | A2 | * | 12/2009 | A63B 69/00 |
| WO | WO-2014089238 | A1 | * | 6/2014 | A61B 5/112 |
| WO | WO-2017157604 | A1 | * | 9/2017 | G01C 22/006 |
| WO | WO-2020152817 | A1 | * | 7/2020 | A61B 5/112 |
| WO | 2020186171 | A1 | | 9/2020 | |
| WO | 2021092676 | A1 | | 5/2021 | |

OTHER PUBLICATIONS

Machine Translation of CN-105708469, Patent Translate, pp. 1-10, printed on Jul. 21, 2025, (Year: 2016).*
Machine Translation of WO-2020152817, Patent Translate, pp. 1-15, printed on Jul. 21, 2025, (Year: 2020).*
Machine Translation of WO-2017157604, Patent Translate, pp. 1-10, printed on Jul. 21, 2025, (Year: 2017).*
Daniel Tik-Pui Fong et al., Estimating the complete ground reaction forces with pressure insoles in walking, Journal of Biomechanics, 2008, 41(11), pp. 2597-2601.
Ryan S. Alcantara et al., Predicting continuous ground reaction forces from accelerometers during uphill and downhill running: A recurrent neural network solution, bioRxiv (The Preprint Server for Biology), 2021.
H.H.C.M. Savelberg et al., Assessment of the horizontal, fore-aft component of the ground reaction force from insole pressure patterns by using artificial neural networks, Clinical Biomechanics, 1999, 14(8), pp. 585-592.
A. Forner Cordero et al., Use of pressure insoles to calculate the compete ground reaction forces, Journal of Biomechanics, 2004, 37(9), pp. 1427-1432.
H. Rouhani et al., Ambulatory assessment of 3D ground reaction force using plantar pressure distribution, Gait & Posture, 2010, 32(3), pp. 311-316.
A. Forner Cordero et al., Inverse dynamics calculations during gait with restricted ground reaction force information from pressure insoles, Gait & Posture, 2006, 23(2), pp. 189-199.
Kenichiro Fukushi et al., Three-dimensional GRF and CoP Estimation during Stair and Slope Ascent/Descent with Wearable IMUs and Foot Pressure Sensors, 2019 41st Annual Conference of the IEEE Engineering in Medicine and Biology Society (EMBC), 2019, pp. 6401-6404.
Su-Bin Joo et al., Improving the ground reaction force prediction accuracy using one-axis plantar pressure: Expansion of input variable for neural network, Journal of Biomechanics, 2016, 49(14), pp. 3153-3161.
Tsolmonbaatar Khurelbaatar et al., Consistent accuracy in whole-body joint kinetics during gait using wearable inertial motion sensors and in-shoe pressure sensors, Gait & Posture, 2015, 42(1), pp. 65-69.
Taeyong Sim et al., Predicting Complete Ground Reaction Forces and Moments During Gait With Insole Plantar Pressure Information Using a Wavelet Neural Network, Journal of Biomechanical Engineering, 2015, 137(9), pp. 091001-1-091001-9.
Feng Wei et al., Prediction of ground reaction forces in level and incline/decline walking from a multistage analysis of plantar pressure data, Journal of Biomechanics, 2019, 84, pp. 46-51.
Ho Seon Choi et al., Design of an Artifical Neural Network Algorithm for a Low-Cost Insole Sensor to Estimate the Ground Reaction Force (GRF) and Calibrate the Center of Pressure (CoP), Sensors, 2018, 18(12), pp. 4349-4361.
D.C. Billing et al., Predicting ground reaction forces in running using micro-sensors and neural networks, Sports Engineering, 2006, 9, pp. 15-27.
Willaim R. Johnson et al., Multidimensional Ground Reaction Forces and Moments From Wearable Sensor Accelerations via Deep Learning, IEEE Transactions on Biomedical Engineering, 2021, 68(1), pp. 289-297.
Eva Dorschky et al., CNN-Based Estimation of Sagittal Plane Walking and Running Biomechanics From Measured and Simulated Inertial Sensor Data, Frontiers in Bioengineering and Biotechnology, 2020, 8(604).
Mark Pogson et al., A neural network method to predict task- and step-specific ground reaction force magnitudes from trunk accelerations during running activities, Medical Engineering and Physics, 2020, 78(4), pp. 82-89.
Frank J. Wouda et al., Estimation of Vertical Ground Reaction Forces and Sagittal Knee Kinematics During Running Using Three Inertial Sensors, Frontiers in Physiology, 2018, 9(218).
Myunghyun Lee et al., Estimation of Three-Dimensional Lower Limb Kinetics Data during Walking Using Machine Learning from a Single IMU Attached to the Sacrum, Sensors, 2020, 20(21), pp. 6277-6292.
David V. Thiel et al., Predicting Ground Reaction Forces in Sprint Running Using a Shank Mounted Inertial Measurement Unit, Proceedings, 2018, 2(6), pp. 199-204.
Dimitrios-Sokratis Komaris et al., Predicting Three-Dimensional Ground Reaction Forces in Running by Using Artificial Neural Networks and Lower Body Kinematics, IEEE Access, 2019, 7, pp. 156779-156786.
Xianta Jiang et al., Estimating Vertical Ground Reaction Force during Walking Using a Single Inertial Sensor, Sensors, 2020, 20(15), pp. 4345-4357.
Ngoh Kieron Jie-Han et al., Estimation of vertical ground reaction force during running using neural network model and uniaxial accelerometer, Journal of Biomechanics, 2018, 76, pp. 269-273.
Mohamed Irfan Mohamed Refai et al., Portable Gait Lab: Estimating Over-Ground 3D Ground Reaction Forces Using Only a Pelvis IMU, Sensors, 2020, 20(21), pp. 6363-6374.
Tian Tan et al., Influence of IMU position and orientation placement errors on ground reaction force estimation, Journal of Biomechanics, 2019, 97, pp. 109416-109420.
Benjamin Leblanc et al., Continuous estimation of ground reaction force during long distance running within a fatigue monitoring framework: A Kalman filter-based model-data fusion approach, Journal of Biomechanics, 2021, 115, pp. 110130-110137.
Mohamed Irfan Mohamed Refai et al., Portable Gait Lab: Estimating 3D GRF Using a Pelvis IMU in a Foot IMU Defined Frame, IEEE Transactions on Neural Systems and Rehabilitation Engineering, 2020, 28(6), pp. 1308-1316.
E. Shahabpoor, Estimation of vertical walking ground reaction force in real-life environments using single IMU sensor, Journal of Biomechanics, 2018, 79, pp. 181-190.

(56) References Cited

OTHER PUBLICATIONS

Bumjoon Kim et al., Spring-loaded inverted pendulum modeling improves neural network estimation of ground reaction forces, Journal of Biomechanics, 2020, 113, pp. 110069-110075.
Dheepak Arumukhom Revi et al., Indirect measurement of anterior-posterior ground reaction forces using a minimal set of wearable inertial sensors: from healthy to hemiparetic walking, Journal of NeuroEngineering and Rehabilitation, 2020, 17(82).
Niels J. Nedergaard et al., The feasibility of predicting ground reaction forces during running from a trunk accelerometry driven mass-spring-damper model, PeerJ, 6, pp. 6105-6121.
Peter M. Mills et al., Agreement between footswitch and ground reaction force techniques for identifying gait events: Inter-session repeatability and the effect of walking speed, Gait & Posture, 2007, 26(2), pp. 323-326.
Oren Tirosh et al., Identifying Heel Contact and Toe-Off Using Forceplate Threshold With a Range of Digital-Filter Cutoff Frequencies, Journal of Applied Biomechanics, 2003, 19(2), pp. 178-184.
Jessica Leitch et al., Identifying gait events without a force plate during running: A comparison of methods, Gait & Posture, 2011, 33(1), pp. 130-132.
Rebecca E. Fellin et al., Comparison of method for kinematic identification of footstrike and toe-off during overground and treadmill running, Journal of Science and Medicine in Sport, 2010, 13(6), pp. 646-650.
Jeffrey M. Hausdorff et al., Footswitch system for measurement of the temporal parameter of gait, Journal of Biomechanics, 1995, 28(3), pp. 347-351.
Robert Mann et al., Reliability and validity of pressure and temporal parameters recorded using a pressure-sensitive insole during running, Gait & Posture, 2014, 39(1), pp. 455-459.
R. Harle et al., Towards real-time profiling of sprints using wearable pressure sensors, Computer Communications, 2012, 35(6), pp. 650-660.
Michael Hanlon et al., Real-time gait event detection using wearable sensors, Gait & Posture, 2009, 30(4), pp. 523-528.
Joe C. Handsaker et al., A kinematic algorithm to identify gait events during running at different speeds and with different footstrike types, Journal of Biomechanics, 2016, 49(16), pp. 4128-4133.
Brad D. Hendershot et al., A comparison of kinematic-based gait event detection methods in a self-paced treadmill application, Journal of Biomechanics, 2016, 49(16), pp. 4146-4149.
Vivek Chandel et al., PI-Sole: A Low-Cost Solution for Gait Monitoring Using Off-The-Shelf Piezoelectric Sensors and IMU, 2019 41st Annual International Conference of the IEEE Engineering in Medicine and Biology Society (EMBC), 2019, pp. 3290-3296.
Rajesh Dey et al., Creeping and Drifting Correction of Sensor Using Adaptive Method, International Journal of Advanced Research in Electrical, Electronics and Instrumentation Engineering, 2014, 3(1), pp. 6670-6676.
Elkin I. Gutierrez Velasquez et al., Error compensation in force sensing resistors, Sensing and Bio-Sensing Research, 2019, 26(2), pp. 100300-100308.
Jonathan S. Schofield et al., The effect of biomechanical variables on force sensitive resistor error: Implications for calibration and improved accuracy, 2016, 49(5), pp. 786-792.
Leonel Paredes-Madrid et al., Self-Compensated Driving Circuit for Reducing Drift and Hysteresis in Force Sensing Resistors, Electronics, 2018, 7(8), pp. 146-165.
A. Arndt, Correction for sensor creep in the evaluation of long-term plantar pressure data, Journal of Biomechanics, 2003, 36(12), pp. 1813-1817.
Chatzaki, et al."The Smart-Insole Dataset: Gait Analysis Using Wearable Sensors with a Focus on Elderly and Parkinson's Patient", Sensors 2021, 21, 2821 (Year: 2021).
Jung, et al., "Ensemble Leaming Using Pressure Sensor for Gait Recognition", 2021 IEEE Region 10 Symposium (TENSYMP) ( 2021): 1-3 (Year: 2021).
Sunarya, et al., "Feature Analysis of Smart Shoe Sensors for Classification of Gait Patterns", Sensors 2020, 20(21), 6253; (Year: 2020).
Eom, et al., "A Deep Learning-Based Optimal Smart Shoes Sensor Selection for Energy Expenditure and Heart Rate Estimation", Sensors 2021, 21, 7058. https://doi.org/10.3390/s21217058 (Year: 2021).
Liu, et al., 2020 J. Phys.: Conf. Ser. 1453 012009, IOP Publishing.
SABOOR_Saboor, et al., "Latest Research Trends in Gait Analysis Using Wearable Sensors and Machine Learning: A Systematic Review," in IEEE Access, vol. 8, pp. 167830-167864, 2020 (Year: 2020).

* cited by examiner

SYSTEM AND METHOD FOR ANALYZING FORCE SENSOR DATA

CROSS-REFERENCE TO RELATED APPLICATIONS

This application claims the benefit of priority of Canadian Patent Application No. 3,176,028 filed Sep. 27, 2022, U.S. Provisional Application No. 63/315,847 filed Mar. 2, 2022, U.S. Provisional Application No. 63/291,424 filed Dec. 19, 2021, and U.S. Provisional Application No. 63/282,234 filed Nov. 23, 2021. All of the above applications are incorporated herein by reference.

FIELD

This document relates to systems and methods for processing data from sensors monitoring human movement or human activity. In particular, this document relates to analyzing force sensor data to identify foot contact events and determine ground reaction forces.

BACKGROUND

U.S. Pat. No. 10,405,779 of Merrell et al. purports to disclose an apparatus including a shoe having a sole with at least a portion of foam replaced with a composite polymeric foam, at least one probe disposed in the composite polymeric foam, a voltage detector coupled to the probe that detects voltage data generated by the composite polymeric foam, and a transformation module that converts voltage data generated by the composite polymeric foam in response to deformation events into GRF, acceleration, or pressure data. In another example, a method includes receiving voltage data produced by composite polymeric foam, the composite polymeric foam providing support and padding in the sole of a shoe, converting the voltage data to force data, comparing the force data to a profile, and transmitting, when the force data fails to fall within a threshold of the profile, a feedback signal to a physical feedback device, the feedback signal indicating a difference with the profile.

U.S. Pat. No. 6,183,425 of Whalen et al. purports to disclose a device to record and analyze habitual daily activity in terms of the history of gait-related musculoskeletal loading. The device consists of a pressure-sensing insole-placed into the shoe or embedded in a shoe sole-which detects contact of the foot with the ground. The sensor is coupled to a portable battery-powered digital data logger clipped to the shoe or worn around the ankle or waist. During the course of normal daily activity, the system maintains a record of time-of-occurrence of all non-spurious foot-down and lift-off events. Offline, these data are filtered and converted to a history of foot-ground contact times, from which measures of cumulative musculoskeletal loading, average walking- and running-specific gait speed, total time spent walking and running, total number of walking steps and running steps, and total gait-related energy expenditure are estimated from empirical regressions of various gait parameters to the contact time reciprocal. Data are available as cumulative values or as daily averages by menu selection. The data provided by this device are useful for assessment of musculoskeletal and cardiovascular health and risk factors associated with habitual patterns of daily activity.

SUMMARY

The following summary is intended to introduce the reader to various aspects of the detailed description, but not to define or delimit any invention.

A system, method, and computer program product for analyzing force sensor data is provided. Force sensor data collected from a plurality of force sensors positioned underfoot can be analyzed in order to detect foot contact events and/or a foot contact period. Foot contact and/or foot off can be detected based on inflection points identified in the force signal data received from the plurality of sensors. Identifying foot contact events by detecting inflection points in the force sensor data can increase the sensitivity of detecting both foot contact and foot off. The use of inflection points also allows both foot contact and foot off to be identified even when these foot contact events occur at different force signal heights.

The force sensor data can be collected using force sensors disposed on a wearable device worn by the user. The wearable device can include a plurality of force sensors. For example, an insole can be provided with the plurality of force sensors and the inertial measurement unit. Sensor data from the force sensors can be used to detect foot contact events for a user regardless of where they are performing an activity. This may allow the user to perform activities at various locations while still tracking and monitoring various gait metrics.

According to some aspects, the present disclosure provides a method for analyzing force sensor data from a plurality of force sensors positioned underfoot, the method comprising: obtaining a sensor signal dataset based on sensor readings from the plurality of force sensors during a first time period, wherein the sensor signal dataset defines a series of signal values extending over the first time period; based on the series of signal values, identifying a pair of interstride interval periods within the first time period, the pair of interstride interval periods including a foot contact interstride interval and a foot off interstride interval, wherein each interstride interval includes a subset of signal values from the series of signal values; identifying a foot contact period by: for each interstride interval, identifying an inflection point in the corresponding subset of signal values; identifying the foot contact period as a time period extending between the inflection points identified for the pair of interstride intervals; and outputting foot contact period data corresponding to the foot contact period.

The plurality of force sensors can be disposed on a wearable device that is worn on a foot.

The wearable device can include a deformable material.

The deformable material can be a foam.

The wearable device can be an insole.

The wearable device can be a shoe.

The wearable device can be a compression-fit garment.

The wearable device can be a sock.

The method can include computing at least one additional foot contact period data based on the foot contact period data.

The at least one additional foot contact period data can be a ground contact time.

The at least one additional foot contact period data can be a ground contact time asymmetry.

The at least one additional foot contact period data can be a stride rate.

The at least one additional foot contact period data can be a swing time.

The at least one additional foot contact period data can be a step count.

The method can include outputting an output dataset, which can include the foot contact period data and/or the at least one additional foot contact period data.

The output dataset can be used as an input to a game.

The output dataset can be used to execute an action in the game.

A gaming scaling factor can be applied to the output dataset in the game.

The gaming scaling factor can be an integer.

The gaming scaling factor can have a value of 1.

An avatar can be generated in the game with motion defined according to the output dataset.

The output dataset can be used to model the dynamics of virtual objects and surroundings with which a user interacts in the game.

A game score in the game can be calculated based on the output dataset.

A training goal can be generated based on the output dataset and/or the game score.

The output dataset and/or the game score can be used to calculate a percentage of progress towards achieving the training goal.

A technique quality of a user performing a movement can be calculated from the output dataset.

A task readiness score can be calculated from the output dataset and/or the technique quality.

A first user can be challenged to replicate the output dataset of a second user in the game.

The wearable device can include at least one vibrotactile motor.

The at least one vibrotactile motor can generate a haptic signal based on the output dataset.

An audio signal can be generated based on the output dataset.

A visual display can be generated based on the output dataset.

For each interstride interval, identifying the inflection point in the corresponding subset of signal values can include: identifying a threshold crossing value in the subset of signal values for that interstride interval; dividing the interstride interval into a plurality of segments; identifying a transition signal value in the subset of signal values for that interstride interval, where the transition signal value is identified at a transition point between adjacent segments in the plurality of segments; tracing a unity line between the threshold crossing value and the transition signal value, the unity line identifying a series of unity line values within the interstride interval; and identifying the inflection point as a point of maximum difference between the unity line values and the subset of signal values.

The foot contact interstride interval can be identified by: identifying a pair of subsequent positive threshold crossings in the series of signal values, where each positive threshold crossing is identified as a point in the first time period where the series of signal values is increasing and crosses a specified threshold value; and defining the foot contact interstride interval as a first interstride period extending between the pair of subsequent positive threshold crossings.

The threshold crossing value for the foot contact interstride interval can be identified at the second positive threshold crossing in the pair of subsequent positive threshold crossings.

The transition signal value for the foot contact interstride interval can be identified at the transition point at the beginning of the last segment in the plurality of segments.

The foot off interstride interval can be identified by: identifying a pair of subsequent negative threshold crossings in the series of signal values, where each negative threshold crossing is identified as a location in the first time period where the series of signal values is decreasing and crosses a specified threshold value; and defining the foot off interstride interval as a second interstride period extending between the pair of subsequent negative threshold crossings.

The threshold crossing value for the foot off interstride interval can be identified at the first negative threshold crossing in the pair of subsequent negative threshold crossings.

The transition signal value for the foot off interstride interval can be identified at the transition point located at the end of the first segment in the plurality of segments.

The method can include classifying the sensor signal dataset as a running dataset or a walking dataset based on the series of signal values; and determining a number of segments in the plurality of segments based on the classification of the sensor signal dataset.

In response to classifying the sensor signal dataset as a running dataset, the number of segments can be determined to be 3 segments.

The specified threshold value can be defined as 50% of the maximum signal value.

The first time period can be at least 5 seconds.

The method can include filtering the sensor signal dataset prior to identifying the pair of interstride intervals.

The filtering can include applying a low-pass filter to the sensor signal dataset.

The method can include classifying the sensor signal dataset as a running dataset or a walking dataset prior to filtering the data.

The method can include identifying a plurality of foot contact periods using a rolling window as the first time period.

The method can include calculating one or more temporal gait metrics using the series of signal values corresponding to the plurality of foot contact periods.

The method can include identifying a swing phase time period that extends between a pair of adjacent foot contact periods, the pair of adjacent foot contact periods including a first foot contact period and a second foot contact period; determining a minimum value of the signal values in the swing phase time period; and adjusting the signal values in the first foot contact period by subtracting the minimum value from each signal value in the first foot contact period.

The foot contact period can extend between a foot contact inflection point and a foot-off inflection point and the method can include accounting for signal hysteresis by: identifying a local maximum signal value in the foot contact period; identifying an unloading signal period extending between the maximum signal value and the foot-off inflection point; and scaling the signal values in the unloading signal period to span from a minimum value of the signal values in the swing phase time period to the local maximum signal value.

The method can include individually accounting for the signal hysteresis for force signal values received from each force sensor in the plurality of force sensors.

According to some aspects, there is also provided a system for analyzing force sensor data, the system comprising: a plurality of force sensors positionable underfoot; and one or more processors communicatively coupled to the plurality of force sensors; wherein the one or more processors are configured to: obtain a sensor signal dataset based on sensor readings from the plurality of force sensors during a first time period, wherein the sensor signal dataset defines a series of signal values extending over the first time period; based on the series of signal values, identify a pair of interstride interval periods within the first time period, the pair of interstride interval periods including a foot contact interstride interval and a foot off interstride interval, wherein each interstride interval includes a subset of signal values from the series of signal values; identify a foot contact period by: for each interstride interval, identifying an inflection point in the corresponding subset of signal values; identifying the foot contact period as a time period extending between the inflection points identified for the pair of interstride intervals; and output foot contact period data corresponding to the foot contact period.

The system can include a wearable device on which the plurality of force sensors are disposed, and the wearable device can be worn on a foot.

The wearable device can include a deformable material.

The deformable material can be a foam.

The wearable device can be an insole.

The wearable device can be a shoe.

The wearable device can be a compression-fit garment.

The wearable device can be a sock.

The one or more processors can be further configured to compute at least one additional foot contact period data based on the foot contact period data.

The at least one additional foot contact period data can be a ground contact time.

The at least one additional foot contact period data can be a ground contact time asymmetry.

The at least one additional foot contact period data can be a stride rate.

The at least one additional foot contact period data can be a swing time.

The at least one additional foot contact period data can be a step count.

The one or more processors can be further configured to output an output dataset, which can include the foot contact period data and/or the at least one additional foot contact period data.

The one or more processors can be further configured to use the output dataset as an input to a game.

The one or more processors can be further configured to execute an action in the game based on the output dataset.

The one or more processors can be further configured to apply a gaming scaling factor to the output dataset in the game.

The gaming scaling factor can be an integer.

The gaming scaling factor can have a value of 1.

The one or more processors can be further configured to generate an avatar in the game with motion defined according to the output dataset.

The one or more processors can be further configured to model the dynamics of virtual objects and surroundings with which a user interacts in the game based on the output dataset.

The one or more processors can be further configured to compute a game score in the game based on the output dataset.

The one or more processors can be further configured to generate a training goal based on the output dataset and/or the game score.

The one or more processors can be further configured to calculate a percentage of progress towards achieving the training goal based on the output data and/or the game score.

The one or more processors can be further configured to determine a technique quality of a user performing a movement based on the output dataset.

The one or more processors can be further configured to determine a task readiness score based on the output dataset and/or the technique quality.

The one or more processors can be further configured to challenge a first user to replicate the output dataset of a second user in the game.

The system can include at least one vibrotactile motor.

The at least one vibrotactile motor can be configured to generate a haptic signal based on the output dataset.

The one or more processors can be further configured to generate an audio signal based on the output dataset.

The one or more processors can be further configured to generate a visual display based on the output dataset.

The one or more processors can be configured to, for each interstride interval, identify the inflection point in the corresponding subset of signal values by: identifying a threshold crossing value in the subset of signal values for that interstride interval; dividing the interstride interval into a plurality of segments; identifying a transition signal value in the subset of signal values for that interstride interval, where the transition signal value is identified at a transition point between adjacent segments in the plurality of segments; tracing a unity line between the threshold crossing value and the transition signal value, the unity line identifying a series of unity line values within the interstride interval; and identifying the inflection point as a point of maximum difference between the unity line values and the subset of signal values.

The one or more processors can be configured to identify the foot contact interstride interval by: identifying a pair of subsequent positive threshold crossings in the series of signal values, where each positive threshold crossing is identified as a point in the first time period where the series of signal values is increasing and crosses a specified threshold value; and defining the foot contact interstride interval as a first interstride period extending between the pair of subsequent positive threshold crossings.

The one or more processors can be configured to identify the threshold crossing value for the foot contact interstride interval at the second positive threshold crossing in the pair of subsequent positive threshold crossings.

The one or more processors can be configured to identify the transition signal value for the foot contact interstride interval at the transition point at the beginning of the last segment in the plurality of segments.

The one or more processors can be configured to identify the foot off interstride interval by: identifying a pair of subsequent negative threshold crossings in the series of signal values, where each negative threshold crossing is identified as a location in the first time period where the series of signal values is decreasing and crosses a specified threshold value; and defining the foot off interstride interval as a second interstride period extending between the pair of subsequent negative threshold crossings.

The one or more processors can be configured to identify the threshold crossing value for the foot off interstride interval at the first negative threshold crossing in the pair of subsequent negative threshold crossings.

The one or more processors can be configured to identify the transition signal value for the foot off interstride interval at the transition point located at the end of the first segment in the plurality of segments.

The one or more processors can be further configured to: classify the sensor signal dataset as a running dataset or a walking dataset based on the series of signal values; and determine a number of segments in the plurality of segments based on the classification of the sensor signal dataset.

The one or more processors can be configured to, in response to classifying the sensor signal dataset as a running dataset, determine the number of segments to be 3 segments.

The one or more processors can be configured to define the specified threshold value as 50% of the maximum signal value.

The first time period can be at least 5 seconds.

The one or more processors can be configured to filter the sensor signal dataset prior to identifying the pair of interstride intervals.

The one or more processors can be configured to filter the sensor signal dataset by applying a low-pass filter to the sensor signal dataset.

The one or more processors can be configured to classify the sensor signal dataset as a running dataset or a walking dataset prior to filtering the data.

The one or more processors can be configured to identify a plurality of foot contact periods using a rolling window as the first time period.

The one or more processors can be configured to calculate one or more temporal gait metrics using the series of signal values corresponding to the plurality of foot contact periods.

The one or more processors can be further configured to: identify a swing phase time period that extends between a pair of adjacent foot contact periods, the pair of adjacent foot contact periods including a first foot contact period and a second foot contact period; determine a minimum value of the signal values in the swing phase time period; and adjust the signal values in the first foot contact period by subtracting the minimum value from each signal value in the first foot contact period.

The one or more processors can be configured to identify the foot contact period as extending between a foot contact inflection point and a foot-off inflection point and the one or more processors can be further configured to account for signal hysteresis by: identifying a local maximum signal value in the foot contact period; identifying an unloading signal period extending between the maximum signal value and the foot-off inflection point; and scaling the signal values in the unloading signal period to span from a minimum value of the signal values in the swing phase time period to the local maximum signal value.

The one or more processors can be configured to individually account for the signal hysteresis for force signal values received from each force sensor in the plurality of force sensors.

A non-transitory computer readable medium storing computer-executable instructions, which, when executed by a computer processor, cause the computer processor to carry out a method for analyzing force sensor data from a plurality of force sensors positioned underfoot wherein the method comprises: obtaining a sensor signal dataset based on sensor readings from the plurality of force sensors during a first time period, wherein the sensor signal dataset defines a series of signal values extending over the first time period; based on the series of signal values, identifying a pair of interstride interval periods within the first time period, the pair of interstride interval periods including a foot contact interstride interval and a foot off interstride interval, wherein each interstride interval includes a subset of signal values from the series of signal values; identifying a foot contact period by: for each interstride interval, identifying an inflection point in the corresponding subset of signal values; identifying the foot contact period as a time period extending between the inflection points identified for the pair of interstride intervals; and outputting foot contact period data corresponding to the foot contact period.

The non-transitory computer readable medium can store computer-executable instructions, which, when executed by a computer processor, cause the computer processor to carry out the method for analyzing force sensor data from a plurality of force sensors positioned underfoot, where the method is described herein.

A system, method, and computer program product for adjusting the magnitude of a ground reaction force is provided. More particularly, in some examples, force sensor data from a plurality of force sensors positioned underfoot can be used to determine a ground reaction force signal. IMU data collected from an inertial measurement unit (IMU) associated with the plurality of force sensors can be used to determine IMU ground reaction force data. The IMU ground reaction force data can be used to determine a scaling factor for the ground reaction force signal determined from the force sensor data. The scaling factor can be applied to the ground reaction force signal to determine a magnitude-adjusted ground reaction force signal. The magnitude-adjusted ground reaction force signal may account for losses in accuracy in the sensor readings that may occur during repetitive dynamic loading.

According to some aspects, the present disclosure provides a method for analyzing force sensor data from a plurality of force sensors positioned underfoot, the method comprising: obtaining force sensor readings from the plurality of force sensors during a first time period; from an inertial measurement unit (IMU), obtaining IMU data during the first time period, the IMU data comprising acceleration data and angular velocity data; identifying a foot contact period based on the force sensor readings; calculating a vertical ground reaction force signal for the foot contact period based on the force sensor readings; determining a scaling factor for the foot contact period by: calculating a mean vertical ground reaction force for the foot contact period based on the force sensor readings; determining a IMU mean vertical ground reaction force using the IMU data for the foot contact period; determining the scaling factor based on the mean vertical ground reaction force and the IMU mean vertical ground reaction force; and adjusting the vertical ground reaction force signal using the scaling factor.

The plurality of force sensors can be disposed on a wearable device that is worn on a foot.

The wearable device can include a deformable material.

The deformable material can be a foam.

The wearable device can be an insole.

The wearable device can be a shoe.

The wearable device can be a compression-fit garment.

The wearable device can be a sock.

The method can include outputting the adjusted vertical ground reaction force signal.

The adjusted vertical ground reaction force signal can be used as an input to a game.

The adjusted vertical ground reaction force signal can be used to execute an action in the game.

A gaming scaling factor can be applied to the adjusted vertical ground reaction force signal in the game.

The gaming scaling factor can be an integer.

The gaming scaling factor can have a value of 1.

An avatar can be generated in the game with motion defined according to the adjusted vertical ground reaction force signal.

The adjusted vertical ground reaction force signal can be used to model the dynamics of virtual objects and surroundings with which a user interacts in the game.

A game score in the game can be calculated based on the adjusted vertical ground reaction force signal.

A training goal can be generated based on the adjusted vertical ground reaction force signal and/or the game score.

The adjusted vertical ground reaction force signal and/or the game score can be used to calculate a percentage of progress towards achieving the training goal.

A technique quality of a user performing a movement can be calculated from the adjusted vertical ground reaction force signal.

A task readiness score can be calculated from the adjusted vertical ground reaction force signal and/or the technique quality.

A first user can be challenged to replicate the adjusted vertical ground reaction force signal of a second user in the game.

The wearable device can include at least one vibrotactile motor.

The at least one vibrotactile motor can generate a haptic signal based on the adjusted vertical ground reaction force signal.

An audio signal can be generated based on the adjusted vertical ground reaction force signal.

A visual display can be generated based on the adjusted vertical ground reaction force signal.

The visual display can be an adjusted vertical ground reaction force signal vs. time graph.

The scaling factor can be determined by dividing the IMU mean vertical ground reaction force by the mean vertical ground reaction force.

The scaling factor can be a linear scaling factor.

The IMU mean vertical ground reaction force can be determined using a machine learning model trained to predict the mean vertical ground reaction force in response to receiving the IMU data as an input.

The machine learning model can be a regression model.

The machine learning model can be trained using training data acquired from one or more users running or walking on a treadmill equipped with force measurement sensors while wearing the wearable device comprising a training IMU.

The machine learning model can be trained to determine the coefficients $C_1$, $C_2$, $C_3$, $C_4$, and $C_5$ of the equation $C_1$*speed+$C_2$*$pACC_2$+$C_3$*pACC+$C_4$*$pGYR_x$+$C_5$=$VGRF_{mean}$, where speed represents a running speed of a given user, $pACC_2$ represents a peak of the absolute value of the vertical acceleration during a training foot contact period as measured by the training IMU, $pACC_y$ represents a peak of the absolute value of the fore-aft acceleration during the training foot contact period as measured by the training IMU, $pGYR_x$ represents a peak of the absolute value of the sagittal plane gyroscope during the training foot contact period as measured by the training IMU, and $vGRF_{mean}$ represents a training IMU mean vertical ground reaction force of the training data during the training foot contact period.

The method can include identifying a plurality of foot contact periods; and for each foot contact period, repeating the steps of calculating the vertical ground reaction force signal, determining the scaling factor, and adjusting the vertical ground reaction force signal using the scaling factor.

Each foot contact period can be identified according to the methods described herein.

According to some aspects, there is also provided a system for analyzing force sensor data, the system comprising: a plurality of force sensors positionable underfoot; and one or more processors communicatively coupled to the plurality of force sensors; wherein the one or more processors are configured to: obtaining force sensor readings from the plurality of force sensors during a first time period; from an inertial measurement unit (IMU), obtaining IMU data during the first time period, the IMU data comprising acceleration data and angular velocity data; identifying a foot contact period based on the force sensor readings; calculating a vertical ground reaction force signal for the foot contact period based on the force sensor readings; determining a scaling factor for the foot contact period by: calculating a mean vertical ground reaction force for the foot contact period based on the force sensor readings; determining a IMU mean vertical ground reaction force using the IMU data for the foot contact period; determining the scaling factor based on the mean vertical ground reaction force and the IMU mean vertical ground reaction force; and adjusting the vertical ground reaction force signal using the scaling factor.

The system can include a wearable device on which the plurality of force sensors are disposed, and the wearable device can be worn on a foot.

The wearable device can include a deformable material.

The deformable material can be a foam.

The wearable device can be an insole.

The wearable device can be a shoe.

The wearable device can be a compression-fit garment.

The wearable device can be a sock.

The one or more processors can be further configured to output the adjusted vertical ground reaction force signal.

The one or more processors can be further configured to use the adjusted vertical ground reaction force signal as an input to a game.

The one or more processors can be further configured to execute an action in the game based on the adjusted vertical ground reaction force signal.

The one or more processors can be further configured to apply a gaming scaling factor to the adjusted vertical ground reaction force signal in the game.

The gaming scaling factor can be an integer.

The gaming scaling factor can have a value of 1.

The one or more processors can be further configured to generate an avatar in the game with motion defined according to the adjusted vertical ground reaction force signal.

The one or more processors can be further configured to model the dynamics of virtual objects and surroundings with which a user interacts in the game based on the adjusted vertical ground reaction force signal.

The one or more processors can be further configured to compute a game score in the game based on the adjusted vertical ground reaction force signal.

The one or more processors can be further configured to generate a training goal based on the adjusted vertical ground reaction force signal and/or the game score.

The one or more processors can be further configured to calculate a percentage of progress towards achieving the training goal based on the adjusted vertical ground reaction force signal and/or the game score.

The one or more processors can be further configured to determine a technique quality of a user performing a movement based on the adjusted vertical ground reaction force signal.

The one or more processors can be further configured to determine a task readiness score based on the adjusted vertical ground reaction force signal and/or the technique quality.

The one or more processors can be further configured to challenge a first user to replicate the adjusted vertical ground reaction force signal of a second user in the game.

The wearable device can include at least one vibrotactile motor.

The at least one vibrotactile motor can be configured to generate a haptic signal based on the adjusted vertical ground reaction force signal.

The one or more processors can be further configured to generate an audio signal based on the adjusted vertical ground reaction force signal.

The one or more processors can be further configured to generate a visual display based on the adjusted vertical ground reaction force signal.

The visual display can be an adjusted vertical ground reaction force signal vs. time graph.

The one or more processors can be configured to determine the scaling factor by dividing the IMU mean vertical ground reaction force by the mean vertical ground reaction force.

The one or more processors can be configured to determine the scaling factor as a linear scaling factor.

The system can include a non-transitory storage memory storing a machine learning model trained to predict the mean vertical ground reaction force; and the one or more processors can be configured to determine the IMU mean vertical ground reaction force by inputting the IMU data to the machine learning model.

The machine learning model can be a regression model.

The machine learning model can be trained using training data acquired from one or more users running or walking on a treadmill equipped with force measurement sensors while wearing the wearable device comprising a training IMU.

The machine learning model can be trained to determine the coefficients $C_1$, $C_2$, $C_3$, $C_4$, and $C_5$ of the equation $C_1*speed+C_2*pACC_2+C_3*pACC_y+C_4*pGYR_x+C_5=VGRF_{mean}$, where speed represents a running speed of a given user, $pACC_z$ represents a peak of the absolute value of the vertical acceleration during a training foot contact period as measured by the training IMU, $pACC_y$ represents a peak of the absolute value of the fore-aft acceleration during the training foot contact period as measured by the training IMU, $pGYR_x$ represents a peak of the absolute value of the sagittal plane gyroscope during the training foot contact period as measured by the training IMU, and $vGRF_{mean}$ represents a training IMU mean vertical ground reaction force of the training data during the training foot contact period.

The one or more processors can be configured to: identify a plurality of foot contact periods; and for each foot contact period, repeat the steps of calculating the vertical ground reaction force signal, determining the scaling factor, and adjusting the vertical ground reaction force signal using the scaling factor.

The one or more processors are configured to identify each foot contact period according to the methods described herein.

A non-transitory computer readable medium storing computer-executable instructions, which, when executed by a computer processor, cause the computer processor to carry out a method for analyzing force sensor data from a plurality of force sensors positioned underfoot wherein the method comprises: obtaining force sensor readings from the plurality of force sensors during a first time period; from an inertial measurement unit (IMU), obtaining IMU data during the first time period, the IMU data comprising acceleration data and angular velocity data; identifying a foot contact period based on the force sensor readings; calculating a vertical ground reaction force signal for the foot contact period based on the force sensor readings; determining a scaling factor for the foot contact period by: calculating a mean vertical ground reaction force for the foot contact period based on the force sensor readings; determining a IMU mean vertical ground reaction force using the IMU data for the foot contact period; determining the scaling factor based on the mean vertical ground reaction force and the IMU mean vertical ground reaction force; and adjusting the vertical ground reaction force signal using the scaling factor.

The non-transitory computer readable medium can store computer-executable instructions, which, when executed by a computer processor, cause the computer processor to carry out the method for analyzing force sensor data from a plurality of force sensors positioned underfoot, where the method is described herein.

A system, method, and computer program product for determining a ground reaction force is provided. More particularly, in some examples, force sensor data is collected from a plurality of force sensors positioned underfoot of a user performing an activity such as running or walking. A user mass, user speed, and user slope can be obtained corresponding to the first time period. The force sensor data can be used along with the user mass, user speed and user slope to determine ground reaction force data with improved accuracy. The ground reaction force data can include multiple components of the ground reaction force (i.e. ground reaction force data corresponding to multiple directions).

According to some aspects, the present disclosure provides a method of determining a ground reaction force using force sensor data from a plurality of force sensors positioned underfoot, the method comprising: obtaining force sensor data for a plurality of specified foot regions based on sensor readings from the plurality of force sensors during a first time period; based on the force sensor data, identifying at least one foot contact period within the first time period; obtaining a user mass, a user speed, and a user slope associated with the force sensor data for the first time period; and for each foot contact period, determining a corresponding vertical ground reaction force signal and a corresponding anterior-posterior ground reaction force signal based on the user mass, the user speed, the user slope, and the force sensor data for the plurality of specified foot regions during the corresponding foot contact period.

The plurality of force sensors can be disposed on a wearable device that is worn on a foot.

The wearable device can include a deformable material.

The deformable material can be a foam.

The wearable device can be an insole.

The wearable device can be a shoe.

The wearable device can be a compression-fit garment.

The wearable device can be a sock.

The method can include outputting an output dataset, which can include the corresponding vertical ground reaction force signal and the corresponding anterior-posterior ground reaction force signal for each foot contact period.

The output dataset can be used as an input to a game.

The output dataset can be used to execute an action in the game.

A gaming scaling factor can be applied to the output dataset in the game.

The gaming scaling factor can be an integer.

The gaming scaling factor can have a value of 1.

An avatar can be generated in the game with motion defined according to the output dataset.

The output dataset can be used to model the dynamics of virtual objects and surroundings with which a user interacts in the game.

A game score in the game can be calculated based on the output dataset.

A training goal can be generated based on the output dataset and/or the game score.

The output dataset and/or the game score can be used to calculate a percentage of progress towards achieving the training goal.

A technique quality of a user performing a movement can be calculated from the output dataset.

A task readiness score can be calculated from the output dataset and/or the technique quality.

A first user can be challenged to replicate the output dataset of a second user in the game.

The wearable device can include at least one vibrotactile motor.

The at least one vibrotactile motor can generate a haptic signal based on the output dataset.

An audio signal can be generated based on the output dataset.

A visual display can be generated based on the output dataset.

The visual display can be an output dataset vs. time graph.

For each foot contact period, determining the corresponding vertical ground reaction force signal and the corresponding anterior-posterior ground reaction force signal can include inputting the user mass, the user speed, the user slope, and the force sensor data for the plurality of specified foot regions during the corresponding foot contact period to a neural network trained to output the corresponding vertical ground reaction force signal and the corresponding anterior-posterior ground reaction force signal.

The neural network can be a recurrent neural network.

The recurrent neural network can have 9 layers.

The neural network can be trained by: obtaining concurrent force sensor training data and ground reaction force measurement training data; obtaining user mass training data, user speed training data, and user slope training data corresponding to the force sensor training data; defining the ground reaction force measurement training data as desired output data; inputting the force sensor training data, the user mass training data, the user speed training data, and the user slope training data to the neural network to cause the neural network to output predicted data; and training the neural network to minimize a cost function determined based on a difference between the desired output data and the predicted data.

The neural network can be a recurrent neural network and the final layer of the recurrent neural network can be a regression output layer and training the neural network to minimize the cost function can include optimizing the regression output layer to minimize a mean square error of the difference between the desired output data and the predicted data.

The regression output layer can be optimized using Adam optimization.

The method can include separating the force sensor data for each specified foot region into a distinct region dataset; and providing each region dataset to the neural network as a separate input.

The force sensor data can be acquired from a particular user; the neural network model can be initially trained using the force sensor training data, ground reaction force measurement training data, user mass training data, user speed training data, and user slope training data for a plurality of users; and the neural network can be enhanced for the particular user prior to determining the corresponding vertical ground reaction force signal and the corresponding anterior-posterior ground reaction force signal.

The neural network can be enhanced by: obtaining concurrent user-specific force sensor training data and user-specific ground reaction force measurement training data for the particular user; obtaining user-specific mass training data, user-specific speed training data, and user-specific slope training data for the particular user corresponding to the user-specific force sensor training data; defining the user-specific ground reaction force measurement training data as user-specific desired output data; inputting adjusted training data to the neural network to cause the neural network to output user-specific predicted data, wherein the adjusted training data includes the user-specific force sensor training data, the user-specific mass training data, the user-specific speed training data, and the user-specific slope training data in addition to the force sensor training data, the user mass training data, the user speed training data, and the user slope training data; and re-training the neural network to minimize the cost function determined based on a user-specific difference between the adjusted desired output data and the user-specific predicted data, wherein the adjusted desired output data includes the desired output data and the user-specific desired output data.

The plurality of specified foot regions can include 5 foot regions.

The force sensor data can be obtained as continuous-time force sensor data over the first time period.

Each foot contact period can be identified using the methods described herein.

According to some aspects, there is also provided a system for determining a ground reaction force, the system comprising: a plurality of force sensors positionable underfoot; and one or more processors communicatively coupled to the plurality of force sensors; wherein the one or more processors are configured to: obtain force sensor data for a plurality of specified foot regions based on sensor readings from the plurality of force sensors during a first time period; based on the force sensor data, identify at least one foot contact period within the first time period; obtain a user mass, a user speed, and a user slope associated with the force sensor data for the first time period; and for each foot contact period, determine a corresponding vertical ground reaction force signal and a corresponding anterior-posterior ground reaction force signal based on the user mass, the user speed, the user slope, and the force sensor data for the plurality of specified foot regions during the corresponding foot contact period.

The system can include a wearable device on which the plurality of force sensors are disposed, and the wearable device can be worn on a foot.

The wearable device can include a deformable material.

The deformable material can be a foam.

The wearable device can be an insole.

The wearable device can be a shoe.

The wearable device can be a compression-fit garment.

The wearable device can be a sock.

The one or more processors can be further configured to output an output dataset, which can include the corresponding vertical ground reaction force signal and the corresponding anterior-posterior ground reaction force signal for each foot contact period.

The one or more processors can be further configured to use the output dataset as an input to a game.

The one or more processors can be further configured to execute an action in the game based on the output dataset.

The one or more processors can be further configured to apply a gaming scaling factor to the output dataset in the game.

The gaming scaling factor can be an integer.

The gaming scaling factor can have a value of 1.

The one or more processors can be further configured to generate an avatar in the game with motion defined according to the output dataset.

The one or more processors can be further configured to model the dynamics of virtual objects and surroundings with which a user interacts in the game based on the output dataset.

The one or more processors can be further configured to compute a game score in the game based on the output dataset.

The one or more processors can be further configured to generate a training goal based on the output dataset and/or the game score.

The one or more processors can be further configured to calculate a percentage of progress towards achieving the training goal based on the output data and/or the game score.

The one or more processors can be further configured to determine a technique quality of a user performing a movement based on the output dataset.

The one or more processors can be further configured to determine a task readiness score based on the output dataset and/or the technique quality.

The one or more processors can be further configured to challenge a first user to replicate the output dataset of a second user in the game.

The system can include at least one vibrotactile motor.

The at least one vibrotactile motor can be configured to generate a haptic signal based on the output dataset.

The one or more processors can be further configured to generate an audio signal based on the output dataset.

The one or more processors can be further configured to generate a visual display based on the output dataset.

The visual display can be an output dataset vs. time graph.

The system can include a non-transitory storage memory storing a neural network trained to determine the corresponding vertical ground reaction force signal and the corresponding anterior-posterior ground reaction force signal; and the one or more processors can be configured to, for each foot contact period, determine the corresponding vertical ground reaction force signal and the corresponding anterior-posterior ground reaction force signal by inputting the user mass, the user speed, the user slope, and the force sensor data for the plurality of specified foot regions during the corresponding foot contact period to the neural network.

The neural network can be a recurrent neural network.

The recurrent neural network can have 9 layers.

The neural network can be trained by: obtaining concurrent force sensor training data and ground reaction force measurement training data; obtaining user mass training data, user speed training data, and user slope training data corresponding to the force sensor training data; defining the ground reaction force measurement training data as desired output data; inputting the force sensor training data, the user mass training data, the user speed training data, and the user slope training data to the neural network to cause the neural network to output predicted data; and training the neural network to minimize a cost function determined based on a difference between the desired output data and the predicted data.

The neural network can be a recurrent neural network and the final layer of the recurrent neural network can be a regression output layer and the neural network can be trained to minimize the cost function by optimizing the regression output layer to minimize a mean square error of the difference between the desired output data and the predicted data.

The regression output layer can be optimized using Adam optimization.

The one or more processors can be configured to separate the force sensor data for each specified foot region into a distinct region dataset; and provide each region dataset to the neural network as a separate input.

The force sensor data can be acquired from a particular user; the neural network model can be initially trained using the force sensor training data, ground reaction force measurement training data, user mass training data, user speed training data, and user slope training data for a plurality of users; and the neural network can be enhanced for the particular user prior to determining the corresponding vertical ground reaction force signal and the corresponding anterior-posterior ground reaction force signal.

The neural network model can be enhanced by: obtaining concurrent user-specific force sensor training data and user-specific ground reaction force measurement training data for the particular user; obtaining user-specific mass training data, user-specific speed training data, and user-specific slope training data for the particular user corresponding to the user-specific force sensor training data; defining the user-specific ground reaction force measurement training data as user-specific desired output data; inputting adjusted training data to the neural network to cause the neural network to output user-specific predicted data, wherein the adjusted training data includes the user-specific force sensor training data, the user-specific mass training data, the user-specific speed training data, and the user-specific slope training data in addition to the force sensor training data, the user mass training data, the user speed training data, and the user slope training data; and re-training the neural network to minimize the cost function determined based on a user-specific difference between the adjusted desired output data and the user-specific predicted data, wherein the adjusted desired output data includes the desired output data and the user-specific desired output data.

The plurality of specified foot regions can include 5 foot regions.

The force sensor data can be obtained as continuous-time force sensor data over the first time period.

The one or more processors can be configured to identify each foot contact period using the methods described herein.

According to some aspects, there is provided a non-transitory computer readable medium storing computer-executable instructions, which, when executed by a computer processor, cause the computer processor to carry out a method of determining a ground reaction force using force sensor data from a plurality of force sensors positioned underfoot, wherein the method comprises: obtaining force sensor data for a plurality of specified foot regions based on sensor readings from a plurality of force sensors positioned underfoot during a first time period; based on the force sensor data, identifying at least one foot contact period within the first time period; obtaining a user mass, a user speed, and a user slope associated with the force sensor data for the first time period; for each foot contact period, determining a corresponding vertical ground reaction force signal and a corresponding anterior-posterior ground reaction force signal based on the user mass, the user speed, the user slope, and the force sensor data for the plurality of specified foot regions during the corresponding foot contact period; and outputting the corresponding vertical ground reaction force signal and the corresponding anterior-posterior ground reaction force signal for each foot contact period.

The non-transitory computer readable medium can store computer-executable instructions, which, when executed by a computer processor, cause the computer processor to carry out the method of determining a ground reaction force using force sensor data from a plurality of force sensors positioned underfoot, where the method is described herein.

BRIEF DESCRIPTION OF THE DRAWINGS

The drawings included herewith are for illustrating various examples of articles, methods, and apparatuses of the present specification and are not intended to limit the scope of what is taught in any way. In the drawings.

DETAILED DESCRIPTION

Figure 1:
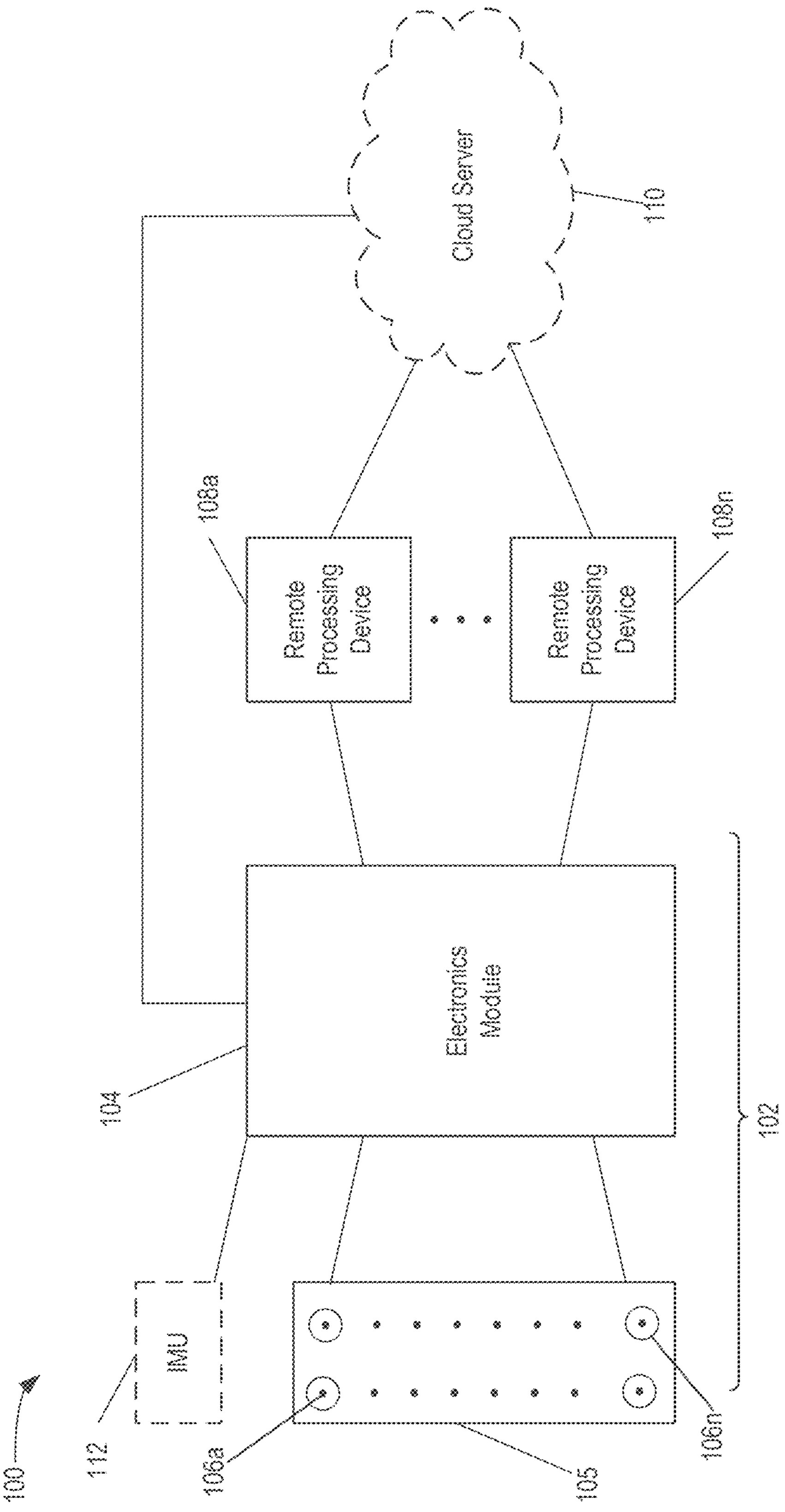
FIG. 1 is a block diagram illustrating an example of a system for analyzing force sensor data.

Various apparatuses or processes or compositions will be described below to provide an example of an embodiment of the claimed subject matter. No embodiment described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

For simplicity and clarity of illustration, reference numerals may be repeated among the figures to indicate corresponding or analogous elements. In addition, numerous specific details are set forth in order to provide a thorough understanding of the subject matter described herein. However, it will be understood by those of ordinary skill in the art that the subject matter described herein may be practiced without these specific details. In other instances, well-known methods, procedures and components have not been described in detail so as not to obscure the subject matter described herein. The description is not to be considered as limiting the scope of the subject matter described herein.

The terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices are directly connected to one another or connected to one another through one or more intermediate elements or devices via an electrical element, electrical signal, or a mechanical element depending on the particular context. Furthermore, the term "communicative coupling" may be used to indicate that an element or device can electrically, optically, or wirelessly send data to another element or device as well as receive data from another element or device.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Terms of degree such as "substantially", "about", and "approximately" as used herein mean a reasonable amount of deviation of the modified term such that the end result is not significantly changed. These terms of degree may also be construed as including a deviation of the modified term if this deviation would not negate the meaning of the term it modifies.

Any recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

Some elements herein may be identified by a part number, which is composed of a base number followed by an alphabetical or subscript-numerical suffix (e.g. 112*a*, or 1121). Multiple elements herein may be identified by part numbers that share a base number in common and that differ by their suffixes (e.g. 1121, 1122, and 1123). All elements with a common base number may be referred to collectively or generically using the base number without a suffix (e.g. 112).

Described herein are systems, methods and devices for analyzing force sensor data from a plurality of force sensors positioned underfoot. The systems, methods, and devices can in some examples use sensors attached to, or contained within, wearable devices or fitness equipment to measure and monitor data relating to movement or activity of a user. The measured data from the sensors can be used to calculate various metrics, such as foot contact events and ground reaction forces.

The sensors can be force sensors and can be disposed on the insole of a shoe or within the footwear worn by the user. The force data acquired by the force sensors can be used to determine the level of force applied by a user's foot while performing various activities. This force data can be used to derive additional force derivatives or force-based metrics, such as the foot contact events and ground reaction forces for the user. The force data, and other data derived therefrom, can be used to determine various metrics for the user that may be useful for medical, fitness, athletic, gaming, security, entertainment or other purposes.

The systems, methods, and devices described herein may be implemented as a combination of hardware or software. In some cases, the systems, methods, and devices described herein may be implemented, at least in part, by using one or more computer programs, executing on one or more programmable devices including at least one processing element, and a data storage element (including volatile and non-volatile memory and/or storage elements). These devices may also have at least one input device (e.g. a pushbutton keyboard, mouse, a touchscreen, and the like), and at least one output device (e.g. a display screen, a printer, a wireless radio, and the like) depending on the nature of the device.

Some elements that are used to implement at least part of the systems, methods, and devices described herein may be implemented via software that is written in a high-level procedural language such as object oriented programming. Accordingly, the program code may be written in any suitable programming language such as Python or C, for example. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods described herein may be capable of being distributed in a computer program product including a computer readable medium that bears computer usable instructions for one or more processors. The medium may be provided in various forms, including non-transitory forms such as, but not limited to, one or more diskettes, compact disks, tapes, chips, and magnetic and electronic storage. Alternatively, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The present disclosure relates in general to systems, methods, and devices that can be used to analyze force sensor data from a plurality of force sensors positioned underfoot. Directly measuring the force (or pressure) applied by a user using underfoot force sensors (as opposed to deriving the force data from other sensors such as accelerometers) can contribute to more accurate calculations of force data and related metrics. As used herein, the term "force" is used broadly and can refer to raw force (i.e. with units of N), or pressure resulting from a raw force (i.e. with units of $N/m^2$).

The systems, methods and devices described herein can also include one or more inertial measurement units (IMUs). Each IMU can be associated with a corresponding plurality of force sensors. That is, each IMU can be configured to collect inertial measurement data relating to movement of the same foot under which the force sensors are positioned.

The systems, methods and devices described herein can also be used to acquire sensor data for both of a user's feet at the same time. In some cases, this may require a separate plurality of force sensors for each foot (e.g. where the force sensors are incorporated into a wearable device). Alternatively, a single plurality of force sensors may be used to acquire force sensor data for both feet (e.g. where the force sensors are provided by fitness equipment).

Where an IMU is included in the system and method, a separate IMU can be provided for each foot. This allows the IMU to collect inertial measurement data relating to movement of that foot. Collecting separate IMU data for each foot may also allow the force sensor data to be distinguished for each foot in cases where a single plurality of force sensors are used to acquire force sensor data for both feet.

General Description of a System for Analyzing Force Sensor Data

The following is a description of a system for analyzing force sensor data that may be used by itself or in any combination or sub-combination with any other feature or features disclosed including the method of identifying foot contact events, the method for correcting the magnitude of a ground reaction force signal, and the method of determining ground reaction force data.

Referring now to FIG. 1, shown therein is a block diagram illustrating an example system 100 that can be used to analyze force sensor data from a plurality of force sensors. System 100 includes a plurality of sensors positioned underfoot of a user performing an activity or other type of movement. The sensors may be provided using a wearable device and/or fitness equipment.

System 100 includes an input unit 102 (also referred to herein as an input device), one or more processing devices 108 (also referred to herein as a receiving device or an output device) and an optional remote cloud server 110. As will be described in further detail below, the input unit 102 may for example be combined with, or integrated into, a carrier unit such as a wearable device or a piece of fitness equipment.

Input unit 102 generally includes a sensing unit 105. The sensing unit 105 can include a plurality of sensors 106*a*-106*n*. The plurality of sensors 106*a*-106*n* can be configured to collect force sensor data from underneath a user's foot.

Optionally, input unit 102 can include an inertial measurement unit (IMU) 112. IMU 112 can include one or more sensors for measuring the position and/or motion of the user's foot (e.g. via a carrier unit). For example, IMU 112 may include sensors such as one or more of a gyroscope, accelerometer (e.g., a three-axis accelerometer), magnetometer, orientation sensor (for measuring orientation and/or changes in orientation), angular velocity sensor, and inclination sensor. Generally, IMU 112 includes at least an accelerometer.

The IMU 112 can also be positioned underneath a user's foot. However, the IMU 112 need not be positioned underfoot so long as the IMU 112 can collect inertial measurement data relating to the position and/or motion of the foot.

Optionally, the input unit 102 can include one or more temperature sensors (not shown) and/or a global positioning system (GPS) (not shown).

The carrier unit can be configured to position the sensors 106 in contact with (or in close proximity to) a user's body to allow the sensors 106 to measure an aspect of the activity being performed by the user. The plurality of sensors 106*a*-106*n* may be configured to measure a particular sensed variable at a location of a user's body when the carrier unit is engaged with the user's body (e.g. when the user is wearing a wearable device containing the sensors 106 or when the user is using fitness equipment containing the sensors 106). In system 100, the plurality of sensors 106*a*-106*n* can be arranged to measure force underneath the foot (underfoot) of a user.

In some examples, the carrier unit may include one or more wearable devices. The wearable devices can be manufactured of various materials such as fabric, cloth, polymer, or foam materials suitable for being worn close to, or in contact with, a user's skin. All or a portion of the wearable device may be made of breathable materials to increase comfort while a user is performing an activity.

In some examples, the wearable device may be formed into a garment or form of apparel such as a sock, a shoe, or an insole. Some wearable devices such as socks may be in direct contact with a user's skin. Some wearable devices, such as shoes, may not be in direct contact with a user's skin but still positioned within sufficient proximity to a user's body to allow the sensors to acquire the desired readings.

In some cases, the wearable device may be a compression-fit garment. The compression-fit garment may be manufactured from a material that is compressive. A compression-fit garment may minimize the impact from "motion artifacts" by reducing the relative movement of the wearable device with respect to a target location on the user's body. In some cases, the wearable device may also include anti-slip components on the skin-facing surface. For example, a silicone grip may be provided on the skin-facing surface of the wearable device to further reduce the potential for motion artifacts.

The wearable device can be worn on a foot. For example, the wearable device may be a shoe, a sock, or an insole, or a portion of a shoe, a sock, or an insole. The wearable device may include a deformable material, such as foam. This may be particularly useful where the wearable device is a shoe or insole.

The plurality of sensors 106*a*-106*n* can be positioned to acquire sensor reading from specified locations on a user's body (via the arrangement of the sensors on the carrier unit). The sensors 106 can be integrated into the material of the carrier unit (e.g. integrated into a wearable device or fitness equipment). Alternatively, the sensors 106 can be affixed or attached to the carrier unit, e.g. printed, glued, laminated or ironed onto a surface, or between layers, of a wearable device or fitness equipment.

In some examples, the carrier unit may include fitness equipment. The fitness equipment may include various types of fitness equipment on which a user can exert force with their foot while performing an activity. For example, the carrier unit may be fitness equipment such as an exercise mat or a treadmill (e.g. a force-instrumented treadmill).

In some examples, the sensors 106 and IMU 112 may be provided by the same carrier unit. Alternatively, the IMU 112 may be provided by a separate carrier unit.

For clarity, the below description relates to a carrier unit in the form of an insole. The insole carrier unit may be provided in various forms, such as an insert for footwear, or integrated into a shoe. However, other carrier units may be implemented using the systems and methods described herein, such as the wearable devices and fitness equipment described above. Incorporating the sensing unit 105 (and optionally the IMU 112) into a carrier unit in the form of a wearable device may be desirable as it allows force sensor data to be analyzed for a user performing activities at various locations and without requiring specifically configured fitness equipment.

The below description relates to an insole in which the plurality of sensors 106 are force sensors. Various types of force sensors may be used, such as force sensing resistors (also referred to as "sensels" or sensing elements), pressure sensors, piezoelectric tactile sensors, elasto-resistive sensors, capacitive sensors or more generally any type of force sensor that can be integrated into a wearable device or fitness equipment.

The plurality of sensors 106 may be arranged into a sensor array. As used herein, the term sensor array refers to a series of sensors arranged in a defined grid. The plurality of sensors 106 can be arranged in various types of sensor arrays. For example, the plurality of sensors 106 can be provided as a set of discrete sensors (see e.g. FIG. 2). A discrete sensor is an individual sensor that acquires a sensor reading at a single location. A set of discrete sensors generally refers to multiple discrete sensors that are arranged in a spaced apart relationship in a sensing unit.

Sensors 106*a*-106*n* may be arranged in a sparse array of discrete sensors that includes void locations where no sensors 106 are located. Alternatively, sensors 106*a*-106*n* may be arranged in a continuous or dense sensor array in which sensors 106 are arranged in a continuous, or substantially continuous manner, across the grid.

Discrete sensors can provide an inexpensive alternative to dense sensor arrays for many applications. However, because no sensors are positioned in the interstitial locations between the discrete sensors and the void locations external to the set of discrete sensors, no actual sensors readings can be acquired for these locations. Accordingly, depending on the desired resolution for the force sensor data, sensor readings may be estimated (rather than measured) at the interstitial locations and at the void locations external to the set of discrete sensors in order to provide sensor data with similar resolution to a dense sensor array. Alternatively, where lower resolution force sensor data is sufficient, sensor readings may not necessarily be estimated.

Various interpolation and extrapolation techniques may be used to estimate sensor values at interstitial locations and external void locations. For instance, sensor values may be estimated using methods of synthesizing sensor data.

According to some aspects, a method for synthesizing sensor data can include: obtaining a plurality of sensor readings from a corresponding plurality of sensors, the plurality of sensors arranged in a first predetermined pattern, wherein the first predetermined pattern maps each of the plurality of sensors to respective locations on a wearable device; and based on the plurality of sensor readings and a plurality of estimation weights, estimating a plurality of synthesized sensor readings for a corresponding plurality of synthesized sensors, the plurality of synthesized sensors arranged in a second predetermined pattern, wherein the second predetermined pattern maps each of the plurality of synthesized sensors to respective locations on the wearable device.

The plurality of estimation weights can be predetermined in a preprocessing phase, and the preprocessing phase can include: obtaining training data, the training data including a plurality of sets of physical sensor readings from physical sensors arranged according to both the first and second predetermined patterns; filtering the training data to obtain filtered training data; using the filtered training data, computing an average sensor reading for each physical sensor to produce an input data set and a reference data set, the input data set including average sensor readings for sensors corresponding to the first predetermined pattern, the reference data set including average sensor readings for sensors corresponding to the second predetermined pattern; and optimizing the estimation weights.

Optimizing the estimation weights can include: initially estimating the estimation weights; computing estimated sensor values based on the input data set and the estimation weights; and performing gradient descent optimization to update the estimation weights, where the gradient descent optimization compares error between the estimated sensor values and the reference data set.

Filtering the training data can include resizing each instance of the training data to a common size. Filtering the training data can also include: dividing the training data into stance data and swing data; and resizing each instance in the set of stance data to a common size.

The plurality of sensor readings can be associated with an activity, and the plurality of synthesized sensor readings can be estimated when the activity is an activity requiring more sensors than can be provided by the plurality of sensors in the first predetermined pattern. The activity can be running, jogging, walking, or cycling.

The method can include predetermining and optimizing estimation weights associated with a specific activity.

The first predetermined pattern can include at least 32 locations.

The first predetermined pattern can include sensors arranged in a 2-3-4-4-4-3 arrangement in a forefoot portion. The first predetermined pattern can include sensors arranged in a 1-1-1 arrangement in a midfoot portion. The first predetermined pattern can include sensors arranged in a 2-1-2-1-2-1 arrangement in a heel portion.

The second predetermined pattern can include at least 32 locations. The second predetermined pattern can include at least 68 locations.

System 100 can be configured to implement various methods of processing force sensor data. The methods of processing force sensor data may be implemented using a controller of the input device 102, a remote processing device 108, or cloud server 110. Examples of methods of processing force sensor data that may be implemented using system 100, include methods 300, 400, 700, 800, 1000, and 1200 shown in FIGS. 3, 4, 7, 8, 10, and 12 respectively and described in further detail herein below.

As shown in FIG. 1, input unit 102 includes an electronics module 104 coupled to the plurality of sensors 106 and to optional IMU 112. In some cases, the electronics module 104 can include a power supply, a controller or other processing unit, a memory, a signal acquisition unit operatively coupled to the controller and to the plurality of sensors 106 (and to IMU 112), and a wireless communication module operatively coupled to the controller.

Generally, the sensing unit refers to the plurality of sensors 106 and the signal acquisition unit. The signal acquisition unit may provide initial analog processing of signals acquired using the sensors 106, such as amplification. The signal acquisition unit may also include an analog-to-digital converter to convert the acquired signals from the continuous time domain to a discrete time domain. The analog-to-digital converter may then provide the digitized data to the controller for further analysis or for communication to a remote processing device 108 or remote cloud server 110 for further analysis.

Optionally, the electronics module 104 may include a controller or other processing device configured to perform the signal processing and analysis. In such cases, the controller on the electronics module 104 may be configured to process the received sensor readings in order to analyze the force sensor data. In some cases, the controller may be coupled to the communication module (and thereby the sensing unit) using a wired connection such as Universal Serial Bus (USB) or other port.

The electronics module 104 can be communicatively coupled to one or more remote processing devices 108*a*-108*n*, e.g. using a wireless communication module (e.g., Bluetooth, Bluetooth Low-Energy, Wi-Fi, ANT+IEEE 802.11, etc.). The remote processing devices 108 can be any type of processing device such as (but not limited to) a personal computer, a tablet, and a mobile device such as a smartphone, a smartwatch or a wristband. The electronics modules 104 can also be communicatively coupled to remote cloud server 110 over, for example, a wide area network such as the Internet.

Each remote processing device 108 and optional remote cloud server 110 typically includes a processing unit, an output device (such as a display, speaker, and/or tactile feedback device), a user interface, an interface unit for communicating with other devices, Input/Output (I/O) hardware, a wireless unit (e.g. a radio that communicates using CDMA, GSM, GPRS or Bluetooth protocol according to standards such as IEEE 802.11a, 802.11b, 802.11g, or 802.11n), a power unit, and a memory unit. The memory unit can include RAM, ROM, one or more hard drives, one or more flash drives, or some other suitable data storage elements such as disk drives, etc.

The processing unit controls the operation of the remote processing device 108 or the remote cloud server 110 and can be any suitable processor, controller or digital signal processor that can provide sufficient processing power processor depending on the desired configuration, purposes, and requirements of the system 100.

The display can be any suitable display that provides visual information. For instance, the display can be a cathode ray tube, or a flat-screen monitor and the like if the remote processing device 108 or remote cloud server 110 is a desktop computer. In other cases, the display can be a display suitable for a laptop, tablet, or handheld device, such as an LED or LCD-based display and the like.

System 100 can generally be used to analyze force sensor data for various purposes such as identifying foot contact events, foot contact periods and ground reaction forces based on sensor readings received from a plurality of sensors positioned underfoot. In some cases, system 100 may also track additional data derived from the sensor readings. The sensor readings, foot contact event data, foot contact period data, ground reaction force data, and derived data may be monitored, stored, and analyzed for the user. Aspects of the monitoring, storage and analysis of biometric features and other metrics may be performed by one or more of the input unit 102, and/or a remote processing device 108, and/or the cloud server 110. For example, a non-transitory storage memory of one or more of the input unit 102, and/or a remote processing device 108, and/or the cloud server 110 can store a machine learning model trained to predict ground reaction forces.

A remote cloud server 110 may provide additional processing resources not available on the input unit 102 or the remote processing device 108. For example, some aspects of processing the sensor readings acquired by the sensors 106 may be delegated to the cloud server 110 to conserve power resources on the input unit 102 or remote processing device 108. In some cases, the cloud server 110, input unit 102 and remote processing device 108 may communicate in real-time to provide timely feedback to a user regarding the sensor readings, foot contact event data, foot contact period data, ground reaction force data, and other related data.

In the example system 100 illustrated in FIG. 1, a single input unit 102 is shown. However, system 100 may include multiple input units 102 associated with the same user. For example, system 100 may include two separate input units 102, each input unit 102 associated with one of the user's legs. Sensor data from an individual input unit 102 may be used for analysis of the force sensor data for the user's corresponding leg.

Accordingly, the system 100 may include a separate sensing unit 105 (and a separate IMU 112 where IMU 112 is included in system 100) for each foot of a user. This may allow the force sensor data to be determined separately for each of the user's feet.

Alternatively, a single sensing unit 105 may be used to acquire force sensor data for both feet of a user. This may be the case where the sensing unit 105 is incorporated into fitness equipment such as an exercise mat or treadmill. In such cases, the force sensor data acquired by the sensing unit 105 may be associated with individual feet through further processing by electronics module 104 and/or processing device 108.

The IMU 112 is associated with a single foot. Accordingly, separate IMUs 112 may be provided for both feet. IMU data acquired by the IMU 112 associated with each foot may be used to associate the force sensor data acquired by a single sensing unit 105 with the corresponding foot.

Certain hardware and software features of the system may be enabled, disabled, or changed. For example, a user may enable or disable certain sensors 106. This may be desirable if the user has a foot condition which inhibits them from activating certain sensors, such as a broken or missing toe. Sampling rate may also be modifiable. Sampling rate may be modified to minimize processing time and to save memory, or to increase data output to gain deeper insights. The location of processing (the input unit 102, the remote processing device 108, or the cloud server 110) may also be changed. If additional sensors are included in the wearable device (e.g. IMU, temperature sensors, and/or GPS), certain sensor types may be enabled or disabled. For example, a GPS system can be disabled to conserve battery power of a carrier unit, if a user operates the carrier unit while running on a treadmill at home.

Figure 2:
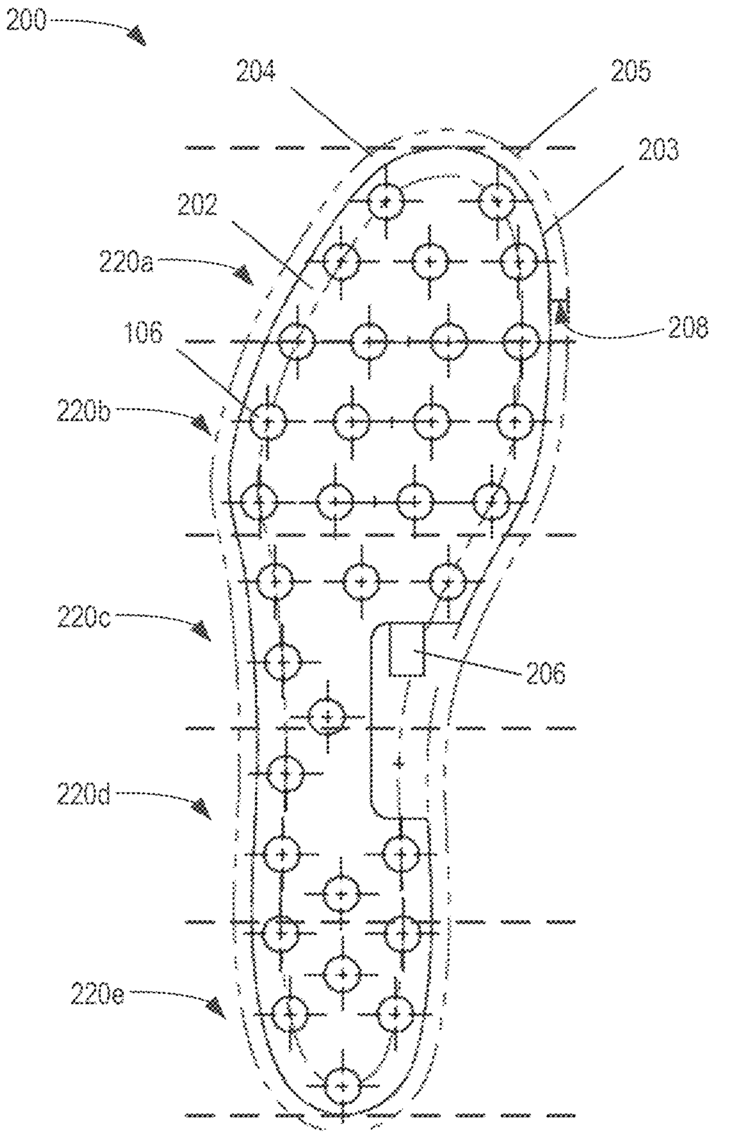
FIG. 2 is a diagram illustrating an example of a wearable device incorporating a sensing unit that can be used in the system of FIG. 1.

Referring now to FIG. 2, shown therein is an example of an insole 200 that includes a sensing unit 202. The insole 200 is an example of an input device 102 that may be used in the system 100 shown in FIG. 1. The insole 200 may be the footwear insert described in PCT Application No. PCT/CA2020/051520 published on May 20, 2021, which is incorporated herein by reference. The insole 200 may be an Orpyx SI® Sensory Insole sold by Orpyx Medical Technologies Inc.

The insole 200 includes a sensor unit 202 and an optional liner 204. The liner 204 can provide a protective surface between the sensor unit 202 and a user's foot. The liner 204 may have a slightly larger profile as compared to the sensor unit 202. That is, the outer perimeter 203 of the sensor unit 202 may be inwardly spaced from the outer perimeter 205 of the liner 204 by an offset 208. The offset 208 may be substantially consistent throughout the perimeter of the sensor unit 202 such that the sensor unit 202 is completely covered by the liner 204.

Optionally, the sensor unit 202 can include an IMU (not shown). The sensor unit 202 can also include a connector 206. The connector 206 may provide a coupling interface between the plurality of sensors 106 (and the optional inertial measurement unit) and an electronics module (not shown) such as electronics module 104. The coupling interface can allow signals from the sensors 106 and/or IMU to be transmitted to the electronics module. In some cases, the coupling interface may also provide control or sampling signals from the electronics module to the sensors 106 and/or IMU.

The arrangement of sensors 106 in the sensor unit 202 is an example of a sparse sensor array that may be used to collect force sensor data. In alternative examples, various different types of force sensors, force sensor arrays, and arrangements of force sensors may be used. For example, sensor units containing a dense force sensor array (e.g. a Pedar® insole with 99 sensors or Tekscan® system) may also be used.

Incorporating the sensor unit 202 in a wearable device such as insole 200 may provide a number of advantages. Fitness equipment equipped with sensors, such as force-instrumented treadmills, are often expensive and may require specialized installation. By contrast, including the sensor unit 202 in a wearable device (e.g. an insole 200) does not require any special installation or modifications to the fitness equipment used by a user.

Incorporating the sensing system into a wearable device may help reduce the cost of the sensing system. Furthermore, the wearable device may allow a user to measure force and other sensor data (e.g. IMU sensor data) while performing various activities including running, walking, jumping, cycling, gaming etc.). This can further offset the cost of the sensing system, as a single sensing system may be used for multiple activities, rather than requiring separate specialized sensing systems for each activity.

Method of Identifying Foot Contact Events

The following is a description of a method of identifying foot contact events that may be used by itself or in any combination or sub-combination with any other feature or features disclosed including the system for analyzing force sensor data, the method for correcting the magnitude of a ground reaction force signal, and the method of determining ground reaction force data.

The motion that a user goes through while running or walking is typically referred to as a gait cycle. The gait cycle generally refers to the time period between the time when a user's foot contacts the ground and the subsequent time when the same foot contacts the ground again. In some cases, the term gait cycle may also refer to the events that occur over that time period.

The term 'stride' is often used to refer to a single gait cycle for one foot. A stride can be divided into two phases, a stance phase, and a swing phase. The stance phase generally refers to the period when the user's foot remains, at least partially, in contact with a surface such as the ground. The swing phase generally refers to the period when the user's foot is not in contact with the surface (e.g. as the foot swings in the air between periods when the foot is in contact with the ground). A stride period generally refers to the time period over which a single gait cycle extends. The stride period includes the time period of one swing phase and one stance phase.

A foot contact event refers to a specific time in the gait cycle. Examples of foot contact events include foot-contact, foot-off and foot flat for example.

Foot contact (FC) refers to the part of a stride when the foot first strikes the ground. Foot contact ends the swing phase of a stride and begins the stance phase of a stride (depending on how the endpoints of the stride period are defined, the strides may be considered the same stride or a different stride). The point in time at which foot contact occurs is referred to herein as the foot-contact time.

Foot off (FO) refers to the part of a stride when the foot completely leaves the ground. Foot off ends the stance phase of a stride and begins the swing phase of a stride (depending on how the endpoints of the stride period are defined, the strides may be considered the same stride or a different stride). The point in time at which foot off occurs is referred to herein as the foot-off time.

A foot contact period refers to the period of time during which a user's foot remains in contact with the ground (i.e. the duration of the stance phase). A foot contact period can be identified as the period between the foot-contact time and the foot-off time of a given stride.

In laboratory settings, foot-contact events are typically identified using force-measuring technology such as force plates or force-instrumented treadmills, which use force-based threshold crossings for FCE identification. While this is an effective technology for laboratory research, this approach cannot be used for measurements taken in real-world settings and across varied locations. Additionally, a threshold crossing-based method requires highly precise and reliable measurement equipment, thereby increasing the cost and complexity of systems employing threshold crossing-based methods. Consistently and accurately identifying foot contact events outside of laboratory settings remains challenging.

In accordance with this aspect, a method of analyzing force sensor data is provided. Force sensor data collected from a plurality of force sensors positioned underfoot can be analyzed in order to detect foot contact events and/or a foot contact period. Foot contact and/or foot off can be detected based on inflection points identified in the force signal data received from the plurality of sensors. Identifying foot contact events based on detection of inflection points in the force sensor data can increase the sensitivity of detecting both foot contact and foot off. The use of inflection points also allows both foot contact and foot off to be identified even when these foot contact events occur at different force signal heights.

Identifying foot contact events based on detection of inflection points in the force sensor data also facilitates the detection of foot contact and foot off in real-time applications. The described methods for detecting inflection points can be applied to discrete segments of force sensor data without the need for data from before or after the data segment relating to the foot contact event being identified.

The force sensor data can be collected using force sensors provided in a wearable device worn by a user. Accordingly, foot contact events can be identified for a user regardless of where they are performing an activity. In addition, gait metrics such as ground contact time, stride rate, and other parameters can be determined for the user at different locations. This also allows foot contact events to be detected for various different types of activities where a user's foot contacts the ground at discrete times (e.g. contacts the ground and then leaves the ground for discrete time segments) and/or cyclically, such as running, walking, stepping, dancing, hiking, skating, cross country skiing, jumping, bounding, gaming and/or other activities (e.g. occupational activities) where the time period relating to the interaction between the ground and a user's foot may be of interest.

The method of analyzing force sensor data can also account for potential drift offset in the force signal. This can ensure that analysis of the force sensor data is not sensitive to signal drift on the part of the sensors.

Figure 3:
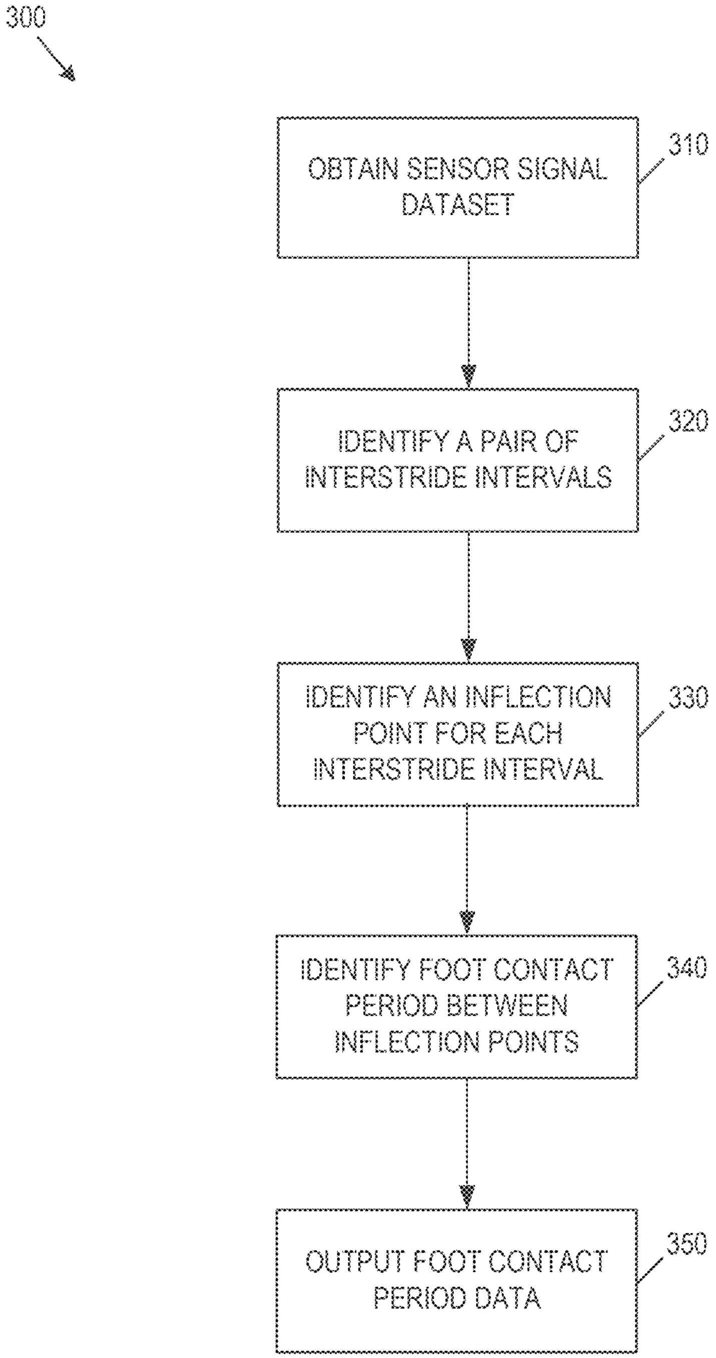
FIG. 3 is a flowchart illustrating an example of a method for analyzing force sensor data.

Referring now to FIG. 3, shown therein is an example method 300 for analyzing force sensor data from a plurality of force sensors positioned underfoot. The method 300 may be used with a plurality of sensors configured to measure human movement or human activity, such as sensors 106. Method 300 is an example of a method for analyzing force sensor data in which a foot contact period is identified based on the force sensor data.

At 310, a sensor signal dataset can be obtained that is based on sensor readings from the plurality of force sensors. The plurality of sensors can include a plurality of force sensors positioned underfoot (i.e. underneath the foot) of a user performing a physical activity. The plurality of force sensors can be configured to acquire force sensor data.

The force sensors can be positioned at specified locations on a carrier unit such as a wearable device or a piece of equipment. The force sensors can be configured to measure force data relating to human activity. As shown in FIG. 2, the plurality of sensors may be force sensors provided at various locations of an insole. The force sensors can measure force applied to the insole during physical activities, such as walking, running, jumping, or gaming.

The sensor signal dataset may be defined by the sensors signals themselves (e.g. where the force sensors are configured to measure force directly). Alternatively, the sensor signal dataset may be generated from the sensor signals (e.g. where the force sensors are configured to measure resistance and the resistance signals are then converted to force signal values).

The sensor readings can be acquired from the plurality of force sensors during a first time period. The sensor signal dataset can define a series of signal values extending over the first time period. The sensor signal dataset can include a plurality of sensor-specific signal values corresponding to each of the force sensors in the plurality of force sensors. Each sensor-specific signal value can correspond to a sensor reading from a particular force sensor at a particular point in time during the first time period.

The sensor signal dataset can be defined as a force signal. The force signal can be a whole foot force signal that is determined using the sensor readings from all of the force sensors in the plurality of force sensors. For example, the force signal can be determined as a sum of the sensor-specific signal values from each of the force sensors in the plurality of force sensors.

The sensor readings may be acquired as a time-continuous set of sensor readings. This may provide a time-continuous set of signal values that can be used to accurately determine the foot contact period. Depending on the nature of the sensors and the signal preprocessing performed, the time-continuous sensor data may be discretized, e.g. using an analog to digital conversion process.

The first time period can be defined to ensure that at least one stride is expected to be captured. The length of time that may be required to capture at least one stride may depend on the activity being performed by a user. Accordingly, the length of the first time period may be adjusted if the activity is known (e.g. by a user inputting data to a processing device 108 indicating the nature of the activity or by identification of the activity through a classification algorithm).

Alternatively, the length of the first time period may be defined to be sufficiently long to capture at least one stride regardless of the activity being performed. For instance, the length of the first time period may be defined to be sufficiently long to capture at least one stride for both running and walking.

For example, the first time period may be defined to be at least about five (5) seconds. This may ensure that at least one stride is captured for both walking and running. A first time period of about 5 seconds may also allow for real-time analysis and feedback of the force sensor data.

Alternatively, a longer time period may be used. This may provide further certainty that a stride is captured for various activities. However, a longer first time period may result in increased processing time, e.g. as a result of needing to filter out superfluous data from adjacent strides.

Alternatively, a shorter first time period may be used. This may further reduce processing time and provide the user with feedback even sooner. For example, a first time period of about 3 seconds may be used.

The first time period may be defined using a rolling window. The rolling window can be used to identify force sensor data corresponding to a plurality of strides.

At 320, a pair of interstride intervals can be identified within the first time period based on the series of signal values obtained at 310. The pair of interstride intervals can include a foot contact interstride interval and a foot off interstride interval.

Each interstride interval can include a corresponding subset of signal values from the series of signal values obtained at 310. The corresponding subset of signal values for each interstride interval generally refers to all of the signal values during that interstride interval. The subset of signal values corresponding to the foot contact interstride interval and the subset of signal values corresponding to the foot off interstride interval can overlap.

Figure 5:
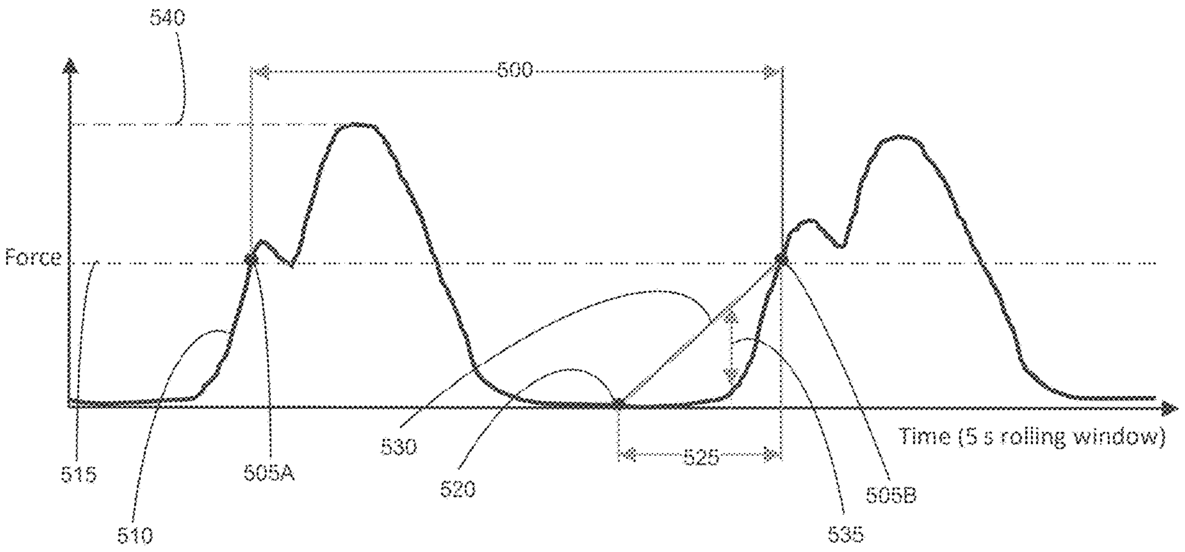
FIG. 5 is a plot illustrating an example of the identification of a foot-contact time.

FIG. 5 illustrates an example process for identifying foot contact. In the example shown in FIG. 5, the process for identifying foot contact is applied to a force signal (e.g. a signal that is determined as the sum of the force sensor values received from each of the force sensors at 310).

As shown in FIG. 5, the foot contact interstride interval 500 can be identified by identifying a pair of subsequent positive threshold crossings **505*a* and 505*b* in the series of signal values (in FIG. 5, the signal values are indicated by the force signal 510). Each positive threshold crossing 505 can be identified as a point in the first time period where the series of signal values is increasing and crosses a specified threshold value 515. The foot contact interstride interval 500 can then be identified as a first interstride period extending between the pair of subsequent positive threshold crossings 505*a* and 505*b*. Accordingly, the signal values between the pair of subsequent positive threshold crossings 505 can be included in the subset of signal values corresponding to the foot contact interstride interval 500**.

Figure 6:
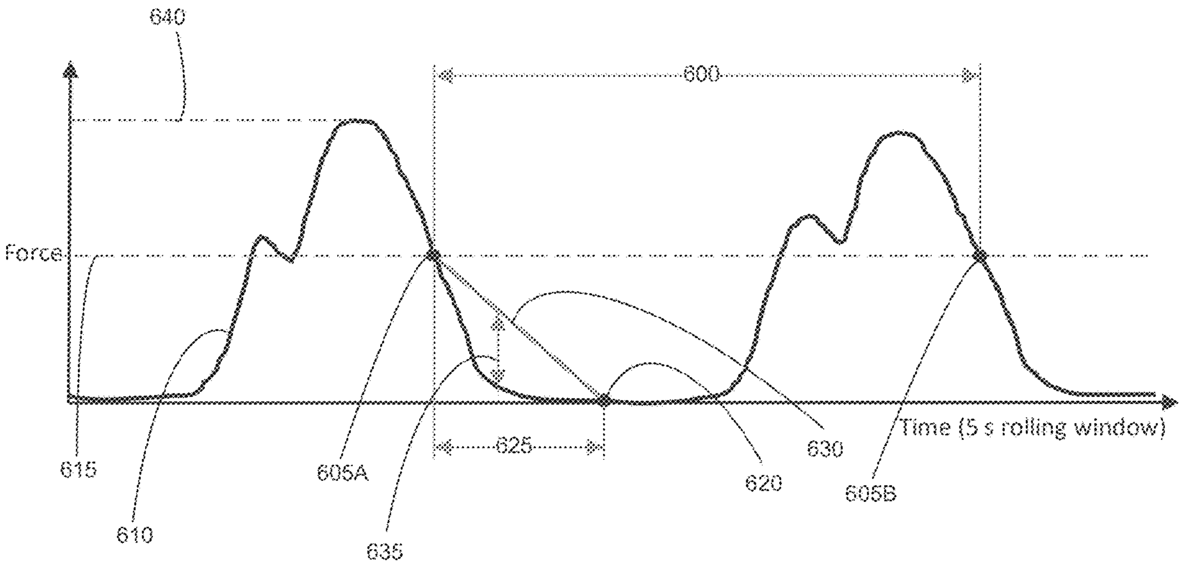
FIG. 6 is a plot illustrating an example of the identification of a foot-off time.

FIG. 6 illustrates an example process for identifying foot off. As shown in FIG. 6, the foot off interstride interval 600 can be identified by identifying a pair of subsequent negative threshold crossings **605*a* and 605*b* in the series of signal values (in FIG. 6, the signal values are indicated by the force signal 610). Each negative threshold crossing 605 can be identified as a point in the first time period where the series of signal values is decreasing and crosses a specified threshold value 615. The foot off interstride interval 600 can then be identified as a second interstride period extending between the pair of subsequent negative threshold crossings 605*a* and 605*b*. Accordingly, the signal values between the pair of subsequent negative threshold crossings 605 can be included in the subset of signal values corresponding to the foot off interstride interval 600**.

The specified threshold value may be defined in various ways. For example, the specified threshold value can be defined as a relative threshold value. A relative threshold value is defined as a signal amplitude threshold that is determined relative to the amplitude of the signals in the sensor signal dataset. For instance, the specified threshold value can be determined relative to a maximum signal value in the sensor signal dataset (e.g. a maximum global signal height in the first time period).

The specified threshold value can be determined as a specified percentage of the maximum signal value. Various different specified percentages may be used. For example, the specified threshold value can be defined as 50% of the maximum signal value (shown at 540 in FIGS. 5 and 640 in FIG. 6). Other specified percentages may be used, such as specified percentages falling within a range between about 20%-80%, or specified percentages falling within a range between about 25% and 75%, or specified percentages falling within a range between about 30% and 70%, or specified percentages falling within a range between about 35% and 65%, or specified percentages falling within a range between about 40% and 60%, for example.

Alternatively, the specified threshold value can be defined as an absolute threshold value. An absolute threshold value is defined as a signal amplitude threshold that is predefined without evaluating the amplitude of the signals in the sensor signal dataset. For example, the specified threshold value can be defined as a predefined force value (e.g. 300N). The predefined force value may be determined based on the user's bodyweight.

The same specified threshold value can be used for both the negative threshold crossing and the positive threshold crossing. This may provide consistency in the detection of the foot contact interstride interval and the foot off interstride interval.

Alternatively, a different specified threshold value may be used to identify the negative threshold crossings and the positive threshold crossings. This may be particularly advantageous for activities with asymmetric force profiles (e.g. where the change in force generated at, and following, foot contact is far more gradual or far more rapid as compared to the change in force generated at, and leading up to, foot off). A number of activities may have asymmetric force profiles, such as jumping (i.e. as compared to landing), skating, and cross-country skiing for example.

For activities with asymmetric force profiles, using a different specified threshold value to detect foot off and foot contact may improve the accuracy of identifying the corresponding inflection point. With jumping, for example, there is a very rapid onset of the force signal at the start of the landing phase (i.e. beginning at foot contact). At the end of the landing phase (i.e. leading up to foot off), there is a more gradual reduction in the force signal and thus a more gradual inflection point. Accordingly, a higher specified threshold value may be used to detect foot off (e.g. 75% of the maximum signal value) as compared to the lower specified threshold value used to detect foot contact (e.g. 50% of the maximum signal value).

The sensor signal dataset can be filtered prior to identifying the pair of interstride intervals. Filtering can be used to remove undesirable signal components such as noise signals and high-frequency vibration signals from the sensor signal dataset. This may help improve accuracy in detecting the inflection points.

To remove undesired signal components, a low-pass filter can be applied to the sensor signal dataset. The filter cut-off frequency can be defined to remove noise signals and high-frequency vibration signals. For example, a cut-off frequency of about 12 Hz may be used, although other suitable cut-off frequencies may also be used (e.g. frequencies in a range between about 5 Hz and 20 Hz).

Various types of filters may be used to remove undesirable signal components, such as perturbations or signal noise. For example, a Butterworth filter may be used to provide low-pass filtering. Alternatively, a different type of filter or a different frequency of Butterworth filter could be used depending on the requirements of a given implementation.

Optionally, the sensor signal data can be classified as a running dataset or a walking dataset prior to filtering the data. For example, an activity classification method may be applied to the sensor signal dataset to determine whether the data corresponds to running or walking. An example of an activity classification method that may be used to classify the sensor signal dataset is described in US Patent Publication No. 2020/0218974 entitled "METHOD AND SYSTEM FOR ACTIVITY CLASSIFICATION", which is incorporated herein by reference.

At 330, an inflection point can be identified for each interstride interval. The inflection point can be identified based on the subset of signal values corresponding to that interstride interval.

The inflection point identified for a given interstride interval can be identified as a foot contact event for that interstride interval. Where the interstride interval is a foot contact interval, the inflection point can correspond to the foot contact time. Where the interstride interval is a foot off interval, the inflection point can correspond to the foot off time.

Various techniques can be used to identify an inflection point in the subset of signal values corresponding to a given interstride interval. An example process 400 for identifying an inflection point is described in further detail herein below with reference to FIG. 4.

At 340, a foot contact period can be identified for the first time period. The foot contact period can be identified as the time period extending between the inflection points identified at 330 for the pair of interstride intervals identified at 320. The foot contact period can reflect the duration of time that a foot remains on the ground during a stride (i.e. the length of the stance phase).

As noted above, the pair of interstride intervals includes a foot contact interval and a foot off interval. The inflection point for the foot contact interval corresponds to the foot-contact time and the inflection point for the foot off interval corresponds to the foot-off time. The foot contact period can be identified as the time period extending between the foot-contact time and the foot-off time to reflect the duration of foot contact for the stride.

At 350, foot contact period data can be output corresponding to the foot contact period. The foot contact period data can include an identification of the foot contact period.

In some examples, additional foot contact period data may be determined based on the identification of one or more foot contact periods. For example, one or more temporal gait metrics may be calculated for one or more foot contact periods. The temporal gait metrics can include various metrics, such as ground contact time (e.g. the length of the foot contact period identified at 340), stride rate, and swing time for example. Other non-temporal gait metrics can also be calculated, such as step count (over one day, during a run, etc.).

The foot contact period data and/or additional foot contact period data can be output directly through an output device to provide a user with feedback on the activity being monitored. This may allow the user to continuously monitor and improve while performing the activity. For example, the foot contact period data may be transmitted to a mobile application on the user's mobile device (e.g. a processing device 108). Alternatively or in addition, the foot contact period data may be stored, e.g. for later review, comparison, analysis, or monitoring. The foot contact period data and/or additional foot contact period data can additionally be used as an input to a game.

The method 300 generally describes the process of determining a foot contact period for one leg. Optionally, method 300 may be applied to determine the foot contact period for both of a user's legs, based, respectively, on data (e.g. sensor readings) collected for each leg. Method 300 may be performed concurrently on the data collected for each leg in order to provide a user with real-time feedback of the foot contact period data corresponding to each leg.

Determining the foot contact period for both feet can also allow further gait metrics to be determined. For example, a ground contact time asymmetry can be calculated by comparing the ground contact time determined for the left foot during a stride to the ground contact time determined for the right foot during its subsequent stride (or vice versa).

Figure 4:
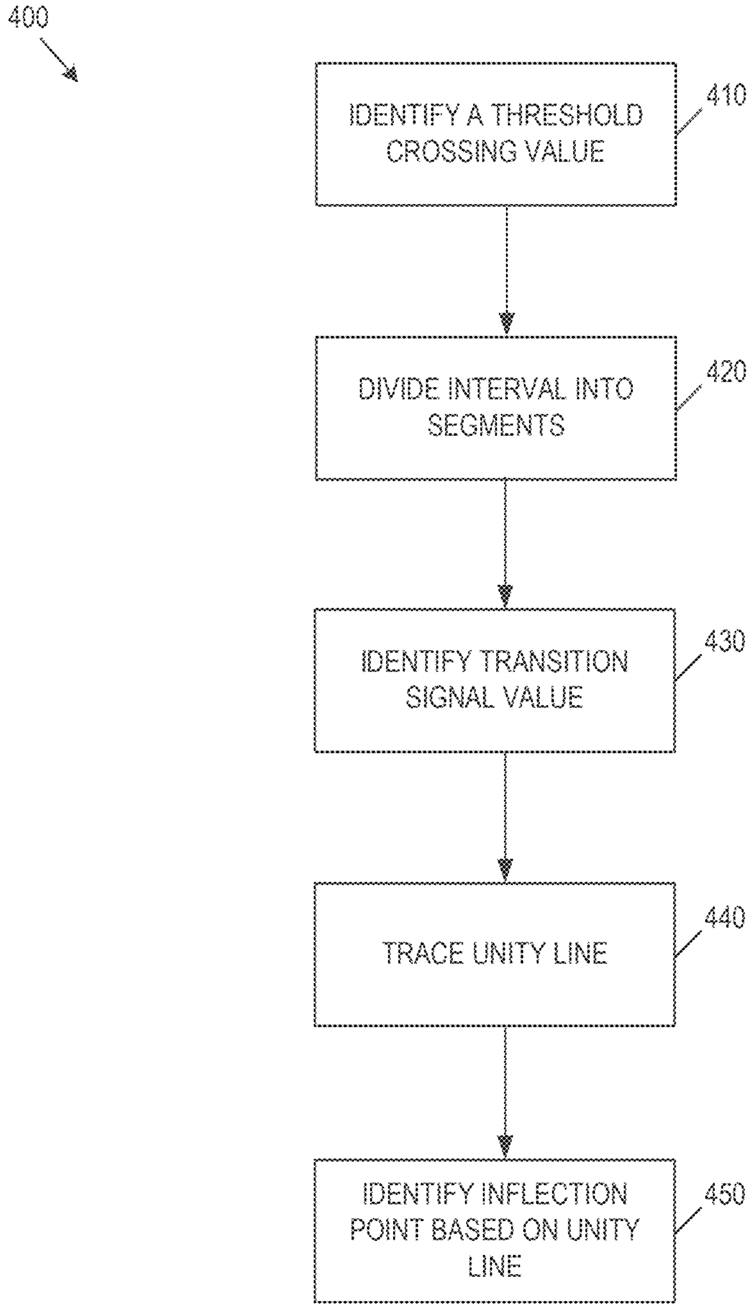
FIG. 4 is a flowchart illustrating an example of a method for identifying an inflection point corresponding to a foot contact event that may be used with the method of FIG. 3.

Referring now to FIG. 4, shown therein is an example method 400 for analyzing force sensor data from a plurality of force sensors positioned underfoot. The method 400 may be used with a plurality of sensors configured to measure human movement or human activity, such as sensors 106. Method 400 is an example of a method for analyzing force sensor data in order to identify a foot contact event. In general, method 400 can be used to identify an inflection point in a given interstride interval that corresponds to a foot contact event.

Method 400 can be used in embodiments of method 300. For example, method 400 may be used to identify inflection points at step 330 of method 300. Method 400 may be applied to identify the inflection point for each interstride interval (identified at 320) in the corresponding subset of signal values for that interstride interval.

Alternatively, method 400 may be used independently to identify an inflection point corresponding to a foot-contact time or a foot-off time. Where method 400 is used independently, steps of obtaining a sensor signal dataset and identifying an interstride interval are performed prior to step 410. Obtaining the sensor signal dataset can be performed in generally the same manner as described above at step 310. Identifying the interstride interval can also be performed in generally the same manner as described above at step 320, except that only one interstride interval need be identified.

At 410, a threshold crossing value can be identified in the subset of signal values for the given interstride interval. The threshold crossing value can be identified as a location where the series of signal values cross a specified threshold value. The specified threshold value can be defined as explained above at step 320 of method 300.

The threshold crossing value can be identified at one of the endpoints of the interstride interval (since the interstride interval can be defined to extend between threshold crossing points). The process of identifying the threshold crossing value may vary based on whether the given interstride interval is a foot contact interval or a foot off interval.

For a foot contact interstride interval, the threshold crossing value can be identified at the second positive threshold crossing 505B (e.g. the last point in time or second endpoint of the foot contact interstride interval 500) in the pair of subsequent positive threshold crossings 505 as shown in the example of FIG. 5.

For a foot off interstride interval, the threshold crossing value can be identified at the first negative threshold crossing 605A (e.g. the first point in time or first endpoint of the foot off interstride interval 600) in the pair of subsequent negative threshold crossings 605 as shown in the example of FIG. 6.

At 420, the interstride interval can be divided into a plurality of segments. Dividing the interstride interval into segments can include separating the interstride interval into multiple portions of equal duration (i.e. of equal length in time).

The number of segments can vary. In some examples, the interstride interval can be divided into 3 segments. Alternatively, a greater or fewer number of segments may be used.

The number of segments can vary based on characteristics associated with the sensor signal data set. For example, the number of segments in the plurality of segments may be determined based on the classification of the sensor signal dataset. As explained herein above, the sensor signal dataset may be classified as a running dataset or a walking dataset based on the series of signal values. For instance, an activity classification algorithm may be applied to the sensor signal dataset to determine whether the data corresponds to running or walking.

The number of segments may then be selected based on whether the sensor signal dataset corresponds to running data or walking data. For example, in response to classifying the sensor signal dataset as a running dataset, the number of segments can be determined to be 3 segments. In response to classifying the sensor signal dataset as a walking dataset, a different number of segments may be used.

Alternatively, the number of segments may be determined based on a length of the interstride interval. For example, the number of segments may be scaled across a range of potential numbers of segments based on the length of the interstride interval. In some cases, the length of the interstride interval may be used to classify the sensor signal dataset as a running dataset or a walking dataset. For example, a shorter interstride interval can be identified as corresponding to a running dataset while a longer interstride interval can be identified as corresponding to a walking dataset.

At 430, a transition signal value can be identified in the subset of signal values for that interstride interval. The transition signal value can be identified at a transition point between adjacent segments in the plurality of segments identified at 420.

The process of identifying the transition signal value may vary based on whether the given interstride interval is a foot contact interval or a foot off interval.

For a foot contact interstride interval 500, the transition signal value 520 can be identified at the transition point at the beginning of the last segment 525 in the plurality of segments as shown in the example of FIG. 5. For instance, where the foot contact interstride interval 500 is divided into 3 segments (as shown in the example of FIG. 5, where the last segment 525 extends across ⅓ of the interstride interval 500), the transition signal value 520 can be identified at a transition point located ⅓ of the interstride interval 500 away from the second threshold crossing 505B.

For a foot off interstride interval 600, the transition signal value 620 can be identified at the transition point located at the end of the first segment 625 in the plurality of segments as shown in the example of FIG. 6. For instance, where the foot off interstride interval is divided into 3 segments (as shown in the example of FIG. 6, where the first segment 625 extends across ⅓ of the interstride interval 600), the transition signal value 620 can be identified at a transition point located ⅓ of the interstride interval 600 away from the first threshold crossing 605A.

At 440, a unity line (see unity line 530 in FIG. 5 and unity line 630 in FIG. 6 for example) can be traced between the threshold crossing value (identified at 410) and the transition signal value (identified at 430). A unity line generally refers to a straight line or linear ramp between two points.

The unity line can identify a series of unity line values within the interstride interval. The unity line values refer to the values identified by the unity line at times between the threshold crossing value and the transition signal value. At the same time, the subset of signal values corresponding to that interstride interval includes values for the times between the threshold crossing value and the transition signal value.

At 450, the inflection point can be identified as a point of maximum difference between the unity line values (identified by the unity line from 440) and the subset of signal values corresponding to the interstride interval.

The point of maximum difference can be identified as the maximum amplitude difference between the unity line values and the subset of signal values. In the example of FIGS. 5 and 6, the maximum amplitude difference (shown as 535 and 635 respectively) can be identified based on the difference in the y-direction between the force signal values and unity line values.

The point of maximum difference can be identified by calculating the difference between the force signal values and unity line values for all times at which the unity line exists. The maximum difference can then be identified. The point in time corresponding to the maximum difference can be identified as the inflection point.

For example, the differences between the force signal values and unity line values for all times at which the unity line exists can populate a one-dimensional array. A MAX function can be used to identify the maximum difference. The index of the maximum difference is identified as the inflection point.

Alternatively, the point of maximum difference can be identified based on a maximum perpendicular difference between the force signal values and unity line values. Rather than determining the difference between the force signal values and unity line values for all times at which the unity line exists, the distance to the force signal along a direction perpendicular to the unity line can be determined for all times at which the unity line exists. The greatest distance can then be identified as the maximum difference. The point in time corresponding to the force signal location at the greatest perpendicular distance to the unity line can be identified as the inflection point.

As noted above, the inflection point can be identified as the time corresponding to a foot contact event such as foot contact or foot off. Once the inflection point is identified, the corresponding foot contact event may also be identified. Corresponding foot contact event data can also be provided for review, feedback or further analysis (e.g. as part of method 300).

The foot contact event data can be output directly through an output device to provide a user with feedback on the activity being monitored. This may allow the user to continuously monitor and improve while performing the activity. For example, the foot contact event data may be transmitted to a mobile application on the user's mobile device (e.g. a processing device 108). Alternatively or in addition, the foot contact event data may be stored, e.g. for later review, comparison, analysis, or monitoring. The foot contact event data can additionally be used as an input to a game.

Methods 300 and 400 can be applied as real-time methods for analyzing force sensor data from a plurality of force sensors positioned underfoot. This may allow a user to be provided with real-time feedback on the activity they are performing. This may be helpful in allowing the user to optimize performance or correct issues with their gait while performing the activity.

Alternatively, methods 300 and 400 can be applied to analyzing force sensor data from a plurality of force sensors positioned underfoot after the activity is complete (e.g. during post-processing or later analysis of stored data).

The foot contact period data, additional foot contact period data, the foot contact event data, or some combination thereof may be outputs (i.e. an output dataset) of the system.

The outputs may be used as inputs to a game. In particular, the data may correspond to a certain foot gesture, and foot gestures may be used to control the game (like buttons on a game controller). In particular, gestures performed in real life may be recreated in a game. For example, the outputs that corresponds to a user walking forward in real life may cause an avatar to walk forward in the same way in a game (e.g. the avatar has the same stride rate). Alternatively, gestures may not be recreated in a game, but may be used to execute controls in a game. For example, a step by a user in real life may serve to select an option in a game menu.

Gestures and outputs and their corresponding actions may be pre-programmed into a game or may be programmed by users. For example, the game may have a preprogrammed heel tap gesture on the left foot that corresponds to an action in the game (e.g. selecting an option in a menu). However, in some cases, not all users are able to perform the heel tap gesture on the left foot (e.g. a user with no left foot). Instead, the user may be able to program their own foot gesture for the selection tool. The user may record another action (e.g. a heel tap on the right foot) that replaces the preprogrammed gesture. In a second example, for a game that uses ground contact time to execute controls, a user may change the length of time that corresponds to different controls in the game. For example, the ground contact times for a user with a prosthetic leg will be different between their right and left foot. The user can program the game to make the ground contact times appear equivalent and execute the same control, whether an action was performed with the right or left foot.

Virtual environments, objects, and avatars may be generated, with which a user using the system can interact. The virtual environment and virtual objects can be altered based on the movements, gestures, and the outputs. Output devices (e.g. a television screen, a virtual reality headset, etc.) may be used to display the virtual environment to users. A user may visit a variety of virtual environments, including imaginary environments or environments that replicate real-life environments (e.g. Central Park, a friend's house, etc.). When a user moves around while wearing the carrier unit, they will move around in and interact with the virtual environment accordingly.

A gaming scaling factor may be applied to outputs in a game. The gaming scaling factor may be an integer (e.g. 1, 2, 5, 10, etc.) or it may not be an integer (e.g. 0.2, 1.5, 2.6, 6.9, etc.). In one example, the gaming scaling factor may be 1. In this case, the outputs are applied equivalently in a game (i.e. a 1:1 scaling). For example, the stride rate of an avatar in a game is equivalent to the stride rate of a user in real life. In another example, the gaming scaling factor may be 5. In this case, outputs are scaled 1:5 from real life to the game. In this case, the stride rate of an avatar in a game is five times the stride rate of a user in real life. Gaming experiences that are directly based on a user's outputs allow users to have a more realistic and immersive gaming experience than games that are not based on a user's biometrics (e.g. games played with buttons on a controller). Output scaling may allow for superhuman performance enhancements in a game. For example, an avatar whose stride rate is scaled by a gaming scaling factor of 5 may be able to outrun a car in a game, but an avatar whose stride rate is scaled by a gaming scaling factor of 1 may not be able to outrun it. Different gaming scaling factors may also be applied to different outputs. For example, a gaming scaling factor of 2 may be applied to the ground contact time, but a gaming scaling factor of 0.5 may be applied to swing time.

Outputs may also be applied to different environmental factors in a game. For example, the gravity in a game can be changed. The gravity can be changed to that of another planet, such as the gravity of Mars. The outputs can be applied to the new environmental factors, so a user can understand how they might perform in a different environment. The performance of the user under the original conditions and the simulated conditions can be shown on a visual display.

The virtual environment can display or generate an avatar representing the portion of a user's body to which the carrier unit is affixed. For example, if the carrier unit is a pair of insoles, a user's feet may be rendered in the virtual environment. The skins and/or shoes applied to the feet in the virtual environment may depend on the user's outputs, or they may be selected by the user. For example, a user may choose a special type of sneaker to be shown in the virtual environment. Special objects and/or abilities may be associated with the virtual skins and shoes. For example, virtual lasers or swords may extend from the virtual shoes that can be used to fight villains in a game. As another example, virtual shoes may contain a special feature, where they can build up energy if a user performs a certain task or reaches certain goals. The built-up energy can be used to create a burst of power in a game involving a cyclic, step-based activity (e.g. a cross-country skiing game).

Alternatively, the virtual environment can display or generate an avatar for the user's entire body. The appearance of the avatar's body may depend on the user's outputs. For example, if a user has long swing times while walking, their avatar may be depicted with long legs. An avatar's appearance may also be location dependent. For example, if a user lives in a warm, dry climate, the avatar may be depicted in shorts and a t-shirt, with dried sand on their skin. Alternatively, if a user lives in the Arctic, their avatar may be depicted in a parka and furry boots. In the virtual environment, there may be location-dependent virtual items that can be unlocked. For example, if a user travels to another country in real life, they may unlock a special running shoe from that country. The carrier unit may contain a GPS system or another location-sensing system to enable the location-dependent items and features to be unlocked.

The outputs may also be used to model the dynamics of virtual objects and/or surroundings within a game, with which a user interacts. For example, if in a game, a user goes on a virtual hike, the amount and trajectory of mud that their avatar kicks up may be modelled based on their stride rate or their swing time.

Additionally, the outputs may be used to control a character in a lifestyle game. These games may require a user to virtually embody a certain lifestyle and complete tasks involved with the lifestyle. For example, a user may embody the lifestyle of an Olympic racewalker in a game. The user will be required to train like an athlete, and the outputs can be used to determine if the user has successfully completed the training. They may also be required to complete other tasks relating to the lifestyle of an Olympic athlete, such as taking rest days, taking part in competitions, achieving sponsorships, going on press tours, going grocery shopping, etc.

The system may also contain safety features to prevent users from injuring themselves on their real life surroundings while gaming. Safety features may be especially important for gaming with virtual reality headsets, where vision is obstructed. One safety feature that may be included in the carrier unit is sensors and/or software that can detect potential or recent collisions of a user with surrounding objects. In response to a detected collision, the system may pause the game to check on the user using a pop-up window. For example, wherein the carrier unit is an insole, software for the Bluetooth system may detect if a user's pair of insoles is in close proximity to another user's pair of insoles. The system may alert the users that they are getting too close to each other and are at risk of a person-to-person collision. In a further example, the system may have a feature where users can measure out a safe playing area. The safe playing area is a real life zone in which a user may safely participate in a game, without risk of collision with surrounding objects. Before a gaming session starts, a user may be asked to walk around the safe playing area, which is recorded in the system. While playing the game, the user may receive feedback and alerts on where they are within the safe playing area. The user's position in the safe playing area may be shown on a visual display on the output or processing device and/or they may receive auditory alerts, visual alerts, tactile alerts, or some combination thereof to indicate they are getting close to or have gone past the edge of the safe playing area.

The system may be paired with other carrier devices in gaming scenarios. For example, the insoles may be paired with other wearable devices, such as wrist-worn IMUs. A gaming platform comprising multiple wearable game controllers at different locations on the body can encourage users to engage with a game using their full body, which may increase their workout and fitness during a game. The system may also be paired with fitness equipment. For example, the insoles can be paired with a treadmill for a running game. The incline of the treadmill can change in response to different virtual terrains (e.g. running up a virtual mountain), and the user's outputs, as determined from the insoles, can determine how they are performing in the game. Visual display carrier units, such as VR headsets, smart glasses, and smart goggles, may also be paired with the insoles to increase the immersivity of games.

The system may also contain additional sensor types, whose data can be used to augment gaming experiences. In particular, temperature sensors may provide various advantages for health, athletic, and gaming applications. The system may include one or more temperature sensors used to measure body or environmental temperature. In a first example, one or more temperature sensors (e.g. thermistors) may be included in a flexible printed circuit within the bulk of the insole. The one or more temperature sensors can detect temperature changes from the body. The temperature changes may be used in an algorithm that adjusts other sensor (e.g. force sensor) readings to account for temperature drift. Alternatively, the one or more temperature sensors may be used to measure the body temperature of users for health and gaming calculations (e.g. calorie burn calculations or task readiness calculations). In another example, the one or more temperature sensors may be affixed to the outside of the shoe or at other locations away from a user's body to determine the external temperature. The external temperature may be used in gaming to send safety messages and notifications to users (e.g. if the external temperature is hot, a user may receive a notification suggesting they hydrate more frequently). The external temperature may also be used to adjust health and gaming calculations and may be used to adjust the virtual environment in a game (e.g. if the external temperature is hot, the game may place the user in a virtual desert).

Additionally, the outputs may contribute to scoring in a game. For example, a performance score may be calculated from the outputs. Improvements in any of the metrics (e.g. ground contact time asymmetry) may result in an increase in the number of points earned in a game, incentivizing users to increase their physical activity and improve their technique during gaming. The outputs may be stored, e.g. for later review, comparison with other users, analysis, or monitoring.

One or more normalization factors may be defined to allow performance scores to be determined fairly for different users. Normalization factors may be applied to account for factors such as mass, weight, age, gender, natural athletic ability, game skill, other physical characteristics, or some combination thereof.

The calculation of performance scores can also include modification factors such as multipliers and bonuses for successful completion of objectives including streaks, skillful movement combinations, and/or other unique game experiences such that performing the same in-game action may not yield the same performance scores each time.

The performance scores and/or outputs may also be used as metrics for zone training. Zone training is a type of athletic training which encourages users to keep their metrics within a range or "zone" of values over a predetermined period of time (e.g. the length of a game). Users may be shown their position in a zone in real-time and may be rewarded for staying within the zone and/or penalized for leaving the zone. For example, a user may be given a ground contact time symmetry zone to stay within for a running game. During the game, the user will be encouraged to keep their ground contact time symmetry in the designated zone to achieve maximum points.

The performance scores and/or the outputs can also be used to determine other gaming-related metrics for a user. For example, a user can be associated with one or more user levels. The user levels generally refer to the experience of a user within a game. User levels may be used to compare users to one another, or to establish progression in fitness and experience over time.

The performance scores and the outputs may also be used to assign and to track progress towards achieving training goals within a predetermined time period. For example, based on a user's performance score over one week, a training goal can be generated for the user to achieve the same or greater performance score the subsequent week. Their performance score can then be tracked the subsequent week to determine the user's percentage of progress towards achieving the training goal.

Training goals can relate to accumulated performance scores, system usage metrics, outputs that should be achieved in a predetermined time period (session, day, week, month, year, season, etc.) or instantaneous values (i.e. a rate) that should be achieved at a certain point in time. Training goals may be suggested by the processing system based on previous activities, be chosen by the user, or be presented as part of a challenge from another user or group of users. Suggested training goals can become increasingly targeted for users as additional sensor data is collected by the system over time.

Training goals can be directed toward weight loss. Wherein the carrier unit is an insole containing force sensors, body weight or mass can be measured by the insoles. Alternatively, an external device may be used to measure body weight or mass and transmit the values to the input device 102, remote processing device 108, or cloud server 110. If a user has a training goal to lose a certain amount of weight, the processing system may recommend certain activities to help them accomplish their goal. In particular, the processing system may recommend fitness-related games that can be played with the carrier unit. For example, for an overweight user, the system may suggest low impact, high calorie burning games. The system may create a fitness-based game schedule for the user to follow, to encourage increased activity and intensity as the user's body weight or mass decreases (i.e. as their percentage of progress towards achieving the training goal increases). The system may also include a digital coach to help the user in their weight loss journey. A user may participate in virtual weight loss groups and/or rooms to encourage participation and support through interacting with other users with similar training goals. Weight loss may also be encouraged through badges, virtual gifts, streaks, and other virtual achievements.

Training goals may also be directed toward education. Specific games and activities may integrate educational concepts (e.g. a jumping game that helps users learn a new language). The same social interactions and virtual achievements in the weight loss example may also apply to a user's journey with an educational goal.

Additionally, the outputs may also be used to assess a user's technique when performing an activity or movement (i.e. their quality of movement). Wherein the carrier unit is an insole containing pressure or force sensors, a user's outputs may be recorded and stored in the system memory for an activity, such as running. As further data is collected for the user, the system may compare previous data against new data to determine differences in technique to notify the user of fatigue or of a potential injury. Alternatively, the system may compare data contralaterally (i.e. between opposing limbs) to determine differences in technique. To assess technique, a machine learning model may be trained on data that includes both "correct" and "incorrect" versions of an activity. In implementation, the model can then classify an activity as "correctly" or "incorrectly" performed. Alternatively, the model can be trained on data that includes rankings (e.g. by a clinician or sports scientist) on technique of certain activities (e.g. a 0 to 5 ranking, where 0 indicates that an activity was poorly executed and where 5 indicates that an activity was perfectly executed). In implementation, the system can reject exercise tasks below a certain ranking and/or output the ranked value. In another example, technique can be assessed based on conditions or restrictions set for each activity. For example, if gait is being assessed, there may be a cut-off ground contact time asymmetry to assess movement quality (e.g. no more than 5% difference between feet). A user's outputs can be used to determine if the condition was met. If the user does not meet the condition or restriction, their technique may be deemed unacceptable.

In a further example, the outputs may also be used to determine a user's "readiness" to participate in a game or activity. At either intermediate or specified points in time, an exercise may be given to a user to assess their state of "task readiness". The exercise may include a jump, squat, balance, sprint, series of steps, or another physical exercise. The exercise may be included as part of a game or challenge or may be separate from game play. Task readiness refers to a user's ability to perform a task at a moment in time. Injury potential, technique, and/or fatigue state of the user may be incorporated in a task readiness score or may be pulled out of the task readiness score and displayed as a separate score. The task readiness, injury potential, technique, and/or fatigue state scores may be recorded over time and may be displayed in a metrics report. The metrics report may be used to quantify improvements and overall fitness. The real-time readiness scores of the user may be reported to the user on the input device 102, remote processing device 108, or cloud server 110. For example, on a display of the remote processing device, a poor task readiness score may be reported as a red bar, an average task readiness score as a yellow bar, and a good task readiness score as a green bar in the top corner of the display. The task readiness feedback may alert the user to a deteriorating quality of their movements, which can be used to make an informed decision on continuation of game play. The task readiness scores may be used to recommend games that are appropriate for the user's physical state (e.g. their fitness level) at a certain point in time. For example, consistently high task readiness scores over a period may indicate that a user should play more advanced games to improve their fitness level. The system may recommend more advanced games to the user or higher-level players to compete against. The task readiness scores may also be used to recommend rest periods for the user or to coach the user through auditory means, visual means, tactile means, or some combination thereof. For example, a virtual coach may be used to instruct the user on how to improve movement quality to gain more points, prevent injury, or achieve another goal in the game.

A virtual coach may be used to assist a user with meeting their training goals. The virtual coach may be trained through machine learning or other algorithms to give suggestions, notifications, and encouragement to the user relating to the training goal. Alternatively, a personal trainer, physiotherapist or other expert in the field may assess a user's historical outputs to develop and suggest training goals and paths to achieving training goals within the game.

Feedback may also be provided to users based on their outputs, their training goals, their task readiness, and their technique. For example, if a user goes on a run and the system calculates significant ground contact time asymmetry between the user's left and right foot, they may be provided with feedback to correct the asymmetry. Feedback may be provided in the form of haptic feedback, such as with vibrational motors embedded in the carrier unit.

Feedback may also be provided in the form of an audio signal. A user's outputs may be sonified and played in real time or post-activity for the user. For example, if a user goes on a run, their ground contact time can be sonified and played in real time. The user can then sonically identify changes in their ground contact time, and they can make real time adjustments to their running technique to maintain or improve their performance. Signal processing techniques may be used to increase the effects of sonification. For example, signals may be amplified, such that the sonification spans a broader range of tones than an unamplified signal, which may make it easier for users to identify changes in tone. Signals may also be layered. For example, the signals from the right and left foot may be added together prior to sonification, or the sonifications from the right and left foot may be played simultaneously. Signals may also be filtered to minimize noise, which may be distracting to a user once the signal is sonified. Visual feedback may also be provided by the system.

Users may review their feedback and data (e.g visualizations, sonifications, and haptics) during or after an activity. Real-time feedback may encourage users to continue to engage with the activity at a higher level of intensity or to increase their intensity. Post-activity data reviews may encourage users to understand their activity and movement statistics to prepare for improvements in the next activity.

Sonification of the outputs may also be used for artistic purposes. For example, these metrics may correspond to certain musical features, such as notes, instruments, tempos, and volumes. In a particular embodiment, a note may be played for the duration of a user's ground contact time while running. Stride rate may control tempo. Users may work together to create music. For example, if two users go running, one user's sonification may create a melody and the other user's sonification may create a harmony. In this regard, users can generate music in real time with their bodies. Similarly, users, such as DJs, may be able to mix music in real time. For example, a DJ may run on a treadmill at a concert while wearing the insoles, and by changing their running technique, they can cue tracks and increase or decrease the speed of tracks.

The outputs may also be used to create visualizations. Visualizations may be data driven (e.g. graphs) or artistic visuals (e.g. data-inspired paintings). For example, a user may be able to "paint" with their insoles by applying force in various areas of the foot and using foot gestures to create different "brush strokes". In another example, a large display screen may be used to show a user's live outputs while they are running, racing, or gaming.

Additionally, information may be communicated to and/or between users through visual, audio, or haptic cues. For example, the system may send a haptic cue to a user's insoles to prompt them to complete a daily challenge based on the outputs (e.g. a step count challenge). The results of their daily challenges may be compared with the results of other users. Alternatively, if cues are sent between users, a first user in a game may challenge a second user in a game to perform an activity by sending a haptic signal to the second user's carrier device. The communicated information may be based upon the two users' outputs. For example, the first user may send a haptic cue to the second user to challenge them to a step count competition, where the user with the most steps in a predetermined time frame will be declared the winner.

Users may also be able to create levels or challenges for other users based on their outputs. For example, in an impersonation game, a first user may be challenged to recreate the walk of a second user (such as a friend or celebrity), by replicating their outputs.

The outputs may be displayed on an output device, as part of the remote processing device 108 or cloud server 110. A user may also be able to interact with a visual display via an interactive medium (e.g. a touchscreen) on the output device. Examples of data visualizations that may be provided on the visual display based on sensor readings and/or derived values of a user using the carrier unit include foot pressure maps to show the pressure distribution on the insoles, foot pressure maps to show the movement of the center of pressure, points displays (e.g. performance score), pop-up notifications of errors in movement, pop-up notifications with suggestions to correct the movement, graphs showing changes in data over time, colour codes (e.g. different colour pop-ups for different performance scores or gestures), footprints whose shapes or depths are estimated based on the sensor readings and/or derived values, cumulative displays (e.g. accumulation of steps, which, when a certain number is reached, may be used to provide a burst of power for an avatar in a game), or any combination thereof. The data visualizations may be altered or enabled or disabled by users, with toggles, buttons, or other actions.

A user's output device may also display information (such as names, their outputs, etc.) of other users in the same area using the same type of system. Carrier units may contain GPS systems or other location-sensing systems to enable viewing information of other users in the same area. Location-sensing may provide opportunities for virtual social interactions between users. Examples of social interactions include gift exchanges, meet-ups in virtual rooms, messaging, game challenges, cooperative games, competitive games, combination games (i.e. games with a competitive and cooperative aspect), tournaments, leaderboards (e.g. for age groups, geographic locations, specific games, etc.), and the ability to "follow" and/or "friend" other users (i.e. adding users to a list of "friends" on the system platform). Other social interactions known in the art, but not listed here, may also be included.

Virtual meeting rooms are digital areas where users may send messages or chats with one another, play games together, and participate in social interactions with other users. The system may have virtual meeting rooms available, or users may create and design their own virtual meeting rooms. The owner of a virtual meeting room may allow open access to the virtual meeting room, or they may restrict access to certain users. The owner may invite users to join their virtual meeting room.

Social interactions may also include competitive races against the outputs of the same user (i.e. their previous scores), other users, a "computer", celebrities, and/or professionals. For example, a user may enable a "ghost" mode, where they can view their previous performances when repeating an activity, to compete against themselves. For example, in a game where a user is required to perform a running activity, they can view a "ghost" of their avatar's best performance while repeating the activity, along with a display window showing the ghost's outputs, to encourage them to match or improve the performance. In another example, in a running game, the user may enable "ghost" mode to view the outputs of a 5000 meter professional runner, who recorded their outputs in the game for other users to copy. The user can work towards matching the professional runner's data to improve their own performance. In another example, a professional runner may create a virtual competition where users can compete against the professional for a month-long running challenge. The participating users' outputs can be compared to the professional's outputs to determine if any of the users beat the professional. Users who participate in and/or win the challenge may receive a virtual reward.

The method 400 generally describes the process of identifying a foot contact event for one leg. Optionally, method 400 may be applied to identify foot contact events for both of a user's legs, based, respectively, on data (e.g. sensor readings) collected for each leg. Method 400 may be performed concurrently on the data collected for each leg in order to provide a user with real-time feedback of the foot contact events corresponding to each leg. Identifying foot contact events for both feet can also allow further gait metrics to be determined. For instance, gait asymmetry metrics can be determined using the foot contact events determined for the right foot and the left foot. For example, a ground contact time asymmetry can be calculated by comparing the ground contact time (e.g. the time between the foot contact and foot off) determined for the left foot during a stride to the ground contact time determined for the right foot during its subsequent stride (or vice versa).

Although method 400 is described in the context of identifying a foot contact time or foot off time corresponding to an inflection point, the steps of method 400 can be applied more generally to identify inflection points using a unity line for various different types of signals. That is, the process of defining a unity line, identifying a point of maximum difference, and identifying the inflection point at the point of maximum difference can be applied to various different types of signals.

As noted above, a plurality of force sensors can be used to measure the force applied by a user's foot. However, force sensors are susceptible to drift over time. The signal offsets that result from sensor drift can lead to inaccurate measurements of the forces underneath a user's foot, which can in turn lead to miscalculation of gait metrics.

Figure 7:
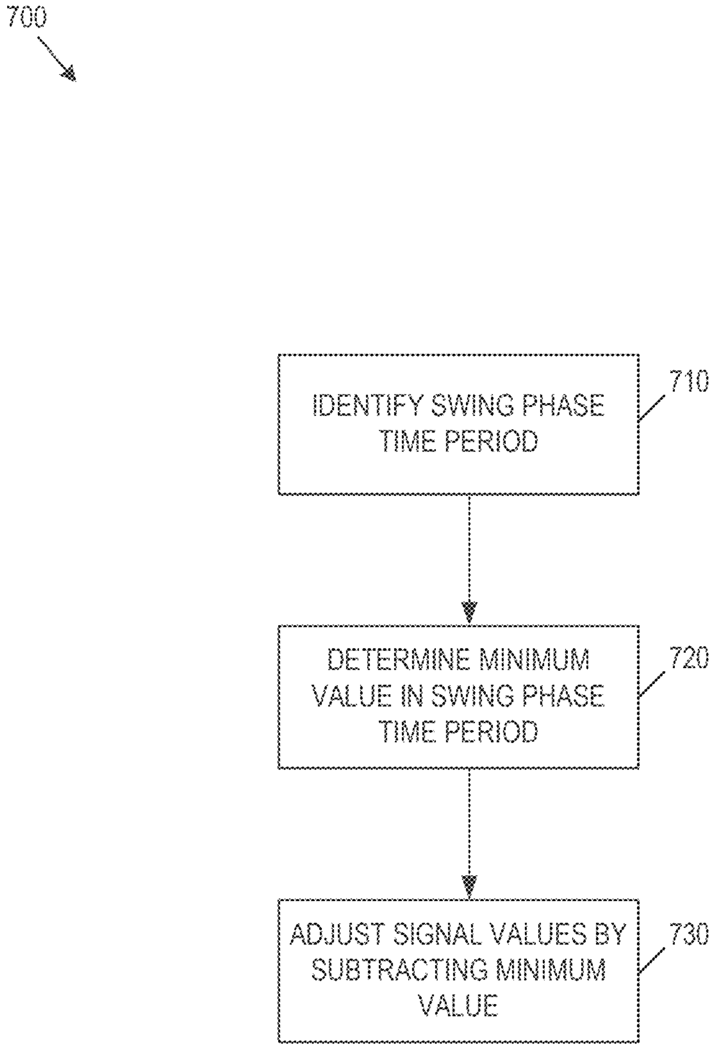
FIG. 7 is a flowchart illustrating an example of a method of adjusting signal values to account for potential signal error that may be used with the method of FIG. 3.

Referring now to FIG. 7, shown therein is an example method 700 for correcting drift offset in force sensor data from a plurality of force sensors positioned underfoot. The method 700 may be used with a plurality of sensors configured to measure human movement or human activity, such as sensors 106. Reference will also be made concurrently to FIG. 9.

Figure 9:
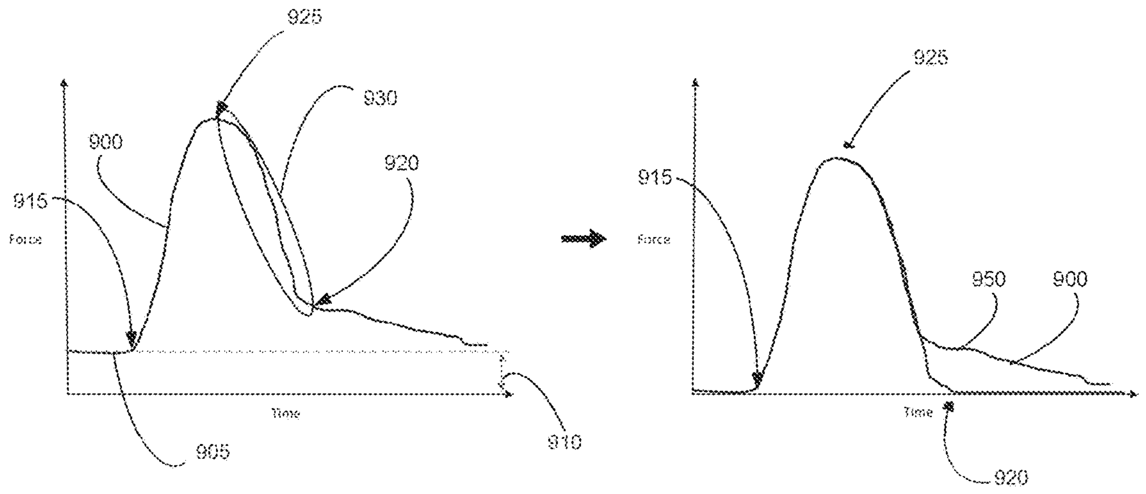
FIG. 9 is a plot illustrating an example of adjusting and scaling signal values according to example implementations of the methods shown in FIGS. 7 and 8.

In general, method 700 can be used to identify signal values (see, for example, the signal values illustrated by signal 900 shown in FIG. 9) that deviate from an expected signal baseline to detect the presence of signal drift. The deviation can then be used to adjust the entire signal to account for the drift.

Method 700 can be used alone or in combination with the other methods described herein involving the analysis of force sensor data, such as methods 300, 400, 800, 1000 and 1200.

At 710, a swing phase time period can be identified. The swing phase time period can be identified as the portion of a stride when the user's foot remains off the ground.

The swing phase time period can be identified based on sensor readings from a plurality of force sensors positioned underfoot (i.e. underneath the foot) of a user performing a physical activity. The plurality of force sensors can be configured to acquire force sensor data.

The swing phase time period can be identified as a period of time that extends between a pair of foot contact periods. The pair of foot contact periods can include a first foot contact period and a second foot contact period. The foot contact periods may be identified using various techniques, such as the example method 300 described herein above.

The swing phase time period can be identified as the time period between the end of the first foot contact period and the start of the second foot contact time period. More generally, the swing phase time period can be identified as a time period extending from a foot-off time (e.g. defining the end of the first foot contact period) and the next foot-contact time (e.g. defining the beginning of the second foot contact period). The foot-off time and foot-contact time may be identified using various techniques, such as the example method 400 described herein above.

At 720, a minimum value 910 of the signal values in the swing phase time period can be determined. The minimum value 910 can be identified as the lowest amplitude signal value 905 in the force sensor data from a point in time during the swing phase time period.

As noted above, the swing phase time period represents the portion of a stride when the user's foot remains off the ground. Accordingly, the signal values in the swing phase time period should return to a baseline value of zero because no force is being applied to the force sensors during this time period. The minimum value 910 identified at 720 can be used to determine if the force sensors include a drift offset value resulting in the signal values not returning to the baseline value of zero.

If the minimum value 910 identified at 720 is non-zero, this can indicate that signal drift has occurred. The minimum value 910 can also be identified as a drift offset value representing the amount of drift that has occurred. This drift offset value can be used to correct for the signal drift by zeroing the swing phase force signal values acquired by the plurality of force sensors.

Alternatively, if the minimum value identified at 720 is zero, the method 700 may end. That is, where the minimum value is zero, the sensor signal dataset may not include a drift offset that needs to be corrected for.

At 730, the signal values in the sensor signal dataset can be adjusted by subtracting the minimum value 910 determined at 720. The minimum value can be subtracted from signal values in the sensor signal dataset corresponding to swing phase time period for which the minimum value was determined. This can include adjusting the signal values in the swing phase time period by subtracting the minimum value.

In addition, signal values during foot contact periods adjacent to the swing phase time period may also be adjusted using the minimum value determined at 720. The signal values in the first foot contact period (the foot contact period immediately preceding the swing phase time period) can be adjusted by subtracting the minimum value. Alternatively or in addition, the signal values in the second foot contact period (the foot contact period immediately after the swing phase time period) can be adjusted by subtracting the minimum value.

A minimum value can be determined separately for a plurality of swing phase time periods. In some cases, a minimum value can be determined for each swing phase time period. The minimum value for a given swing phase time period may be used to adjust the signal values for that given swing phase time period. The minimum value for a given swing phase time period may be used to adjust the signal values for one or both of the foot contact periods adjacent to that given swing phase time period. In some cases, an average of the minimum values determined for successive swing phase time periods may be used to adjust the signal values for the foot contact period between the successive swing phase time periods. Alternatively, the signal values for each foot contact period may be adjusted based on the minimum value for the swing phase time period either immediately before or immediately after the respective foot contact period.

Method 700 can be used to account for signal drift in the sensor signal dataset over time. Method 700 can also be used to identify changes in the signal baseline for the plurality of force sensors. For example, where the sensors are provided by a wearable device, the baseline values may change depending on the tightness of a user's shoes. Method 700 can be applied to adjust the force sensor signals to account for such changes in the baseline signal values.

Figure 8:
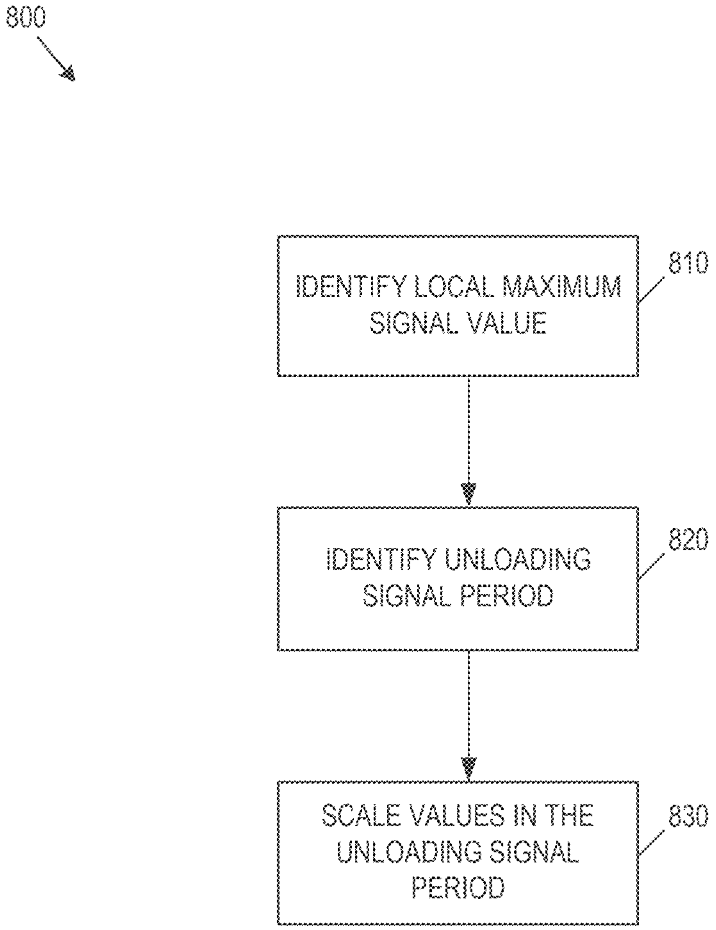
FIG. 8 is a flowchart illustrating an example of a method of scaling signal values to account for potential signal error that may be used with the method of FIG. 3.

Force sensors can also experience hysteresis in the form of a lag in returning to baseline after force has been removed from the sensor. Signal hysteresis may have various causes, such as insufficient airflow to the sensor. Sensor readings that include such a lag result in inaccurate force measurements and can lead to the miscalculation of important temporal gait metrics such as ground contact time (GCT) and stride rate Referring now to FIG. 8, shown therein is an example method 800 for scaling force sensor data from a plurality of force sensors positioned underfoot. The method 800 may be used with a plurality of sensors configured to measure human movement or human activity, such as sensors 106.

In general, method 800 can be used to account for signal hysteresis in the force sensor data acquired by force sensors positioned underfoot. Method 800 can analyze force sensor data corresponding to individual foot contact periods in order to identify, and account for, signal hysteresis.

Method 800 can be used alone or in combination with the other methods described herein involving the analysis of force sensor data, such as methods 300, 400, 700, 1000 and 1200.

As noted above, method 800 can be applied to force signal values (such as the signal values indicated by signal 900 in FIG. 9) corresponding to a foot contact period. The foot contact period can be identified as extending between a foot contact time 915 (e.g. a foot contact inflection point detected using method 400) and a foot-off time 920 (e.g. a foot-off inflection point detected using method 400).

At 810, a local maximum signal value 925 can be identified in the foot contact period. The local maximum signal value 925 can be identified as the highest signal value that occurs in a single stride. As the force sensors experience force primarily during the foot contact period of the stride, the local maximum signal value should occur during the foot contact period.

At 820, an unloading signal period 930 can be identified in the foot contact period. The unloading signal period 930 generally refers to the period during which force applied to the force sensors is unloaded until no force is being applied. The unloading signal period 930 can be identified as extending between the maximum signal value 925 determined at 810 and the foot-off time 920 (or foot-off inflection point). Force unloading generally occurs between these two events.

At 830, the signal values during the unloading signal period 930 can be scaled. The scaling can be defined to account for potential signal hysteresis during the unloading signal period. The signal values in the unloading signal period 930 can be scaled to span from a minimum value 905 of the signal values in the swing phase time period (e.g. as determined at step 720 of method 700) to the local maximum signal value 925.

That is, the signal values in the unloading portion 930 can be stretched in the y-direction (e.g. stretched in amplitude) such that the signal values in the unloading portion 930 span from the baseline/minimum value 905 to the local maximum signal value 925. The signal values after the foot-off time 920 may also be adjusted to account for potential signal hysteresis. For instance, the signal values after the foot-off time period can be adjusted to the baseline/minimum value 905.

The signal values in the unloading portion may be scaled using a linear scaling factor (see e.g. FIG. 9). Alternatively, a non-linear scaling factor (e.g. a quadratic scaling factor) may be used to scale the signal values in the unloading portion.

Method 800 may be used in combination with method 700 to provide error correction in the force signals acquired from a plurality of force sensors. Accordingly, method 700 may be used to adjust the signal such that its baseline is zero, and method 800 may be used to correct the unloading portion of the signal, such that the signal values span from zero to the local maximum signal value after correcting for the offset drift (i.e. the local maximum signal value would be adjusted as a result of the signal adjustment provided by method 700).

Method 800 can be applied to force sensor data from the force sensors' individual signals and/or to an overall force signal. For instance, method 800 can be applied to data from an individual force sensor in order to individually account for the signal hysteresis of force signal values received from that force sensor. This can be repeated for each and every force sensor. Method 800 can also be applied to the overall force signal generated from the force signals from all of the force sensors in the plurality of force sensors.

FIG. 9 illustrates an example plot of an initial force signal 900 (left hand plot) and a plot of a corresponding error-corrected force signal 950 (right hand plot). The error-corrected force signal is illustrated after applying the error-correction methods 700 and 800.

The error-correction methods described herein (e.g, methods 700, 800, and 1000), both individually and collectively, may provide a number of advantages when analyzing force sensor data. For instance, the error-correction methods described herein can ensure that force sensor data obtained from a plurality of force sensors remains accurate for longer periods of time. This may reduce or delay the need for re-calibration, maintenance or replacement, which can be inconvenient and difficult to perform for an end-user.

Ensuring the accuracy of the force sensor data also increases the accuracy in determining derived metrics, such as temporal gait metrics (FCEs, GCT, etc.), as well as pressure, force, and other derived calculations, which would otherwise be impacted by signal drift and signal hysteresis, as well as magnitude errors (see method 1000 described herein below).

Method for Correcting the Magnitude of a Ground Reaction Force Signal

The following is a description of a method for correcting the magnitude of a ground reaction force signal that may be used by itself or in any combination or sub-combination with any other feature or features disclosed including the system for analyzing force sensor data, the method of identifying foot contact events, and the method of determining ground reaction force data.

Force sensors can lose accuracy during repetitive dynamic loading. This can produce magnitude errors in the force sensor signal over the time of loading (i.e. the signal amplitude may increase or decrease as loading continues, even though the same force is applied). To ensure that accurate data is collected and generated relating to a user's movement and activity, the magnitudes of these force signals should be corrected.

In accordance with this aspect, a method of analyzing force sensor data to determine a magnitude-adjusted force signal is provided. Force sensor data collected from a plurality of force sensors positioned underfoot can be analyzed to determine a ground reaction force signal. IMU data collected from an inertial measurement unit (IMU) associated with the plurality of force sensors can also be analyzed to determine IMU ground reaction force data. The IMU ground reaction force data can be used to determine a scaling factor for the ground reaction force signal determined from the force sensor data. The scaling factor can be applied to the ground reaction force signal to determine a magnitude-adjusted ground reaction force signal. The magnitude-adjusted ground reaction force signal may account for any loss in accuracy in the sensor readings from the plurality of force sensors.

Figure 10:
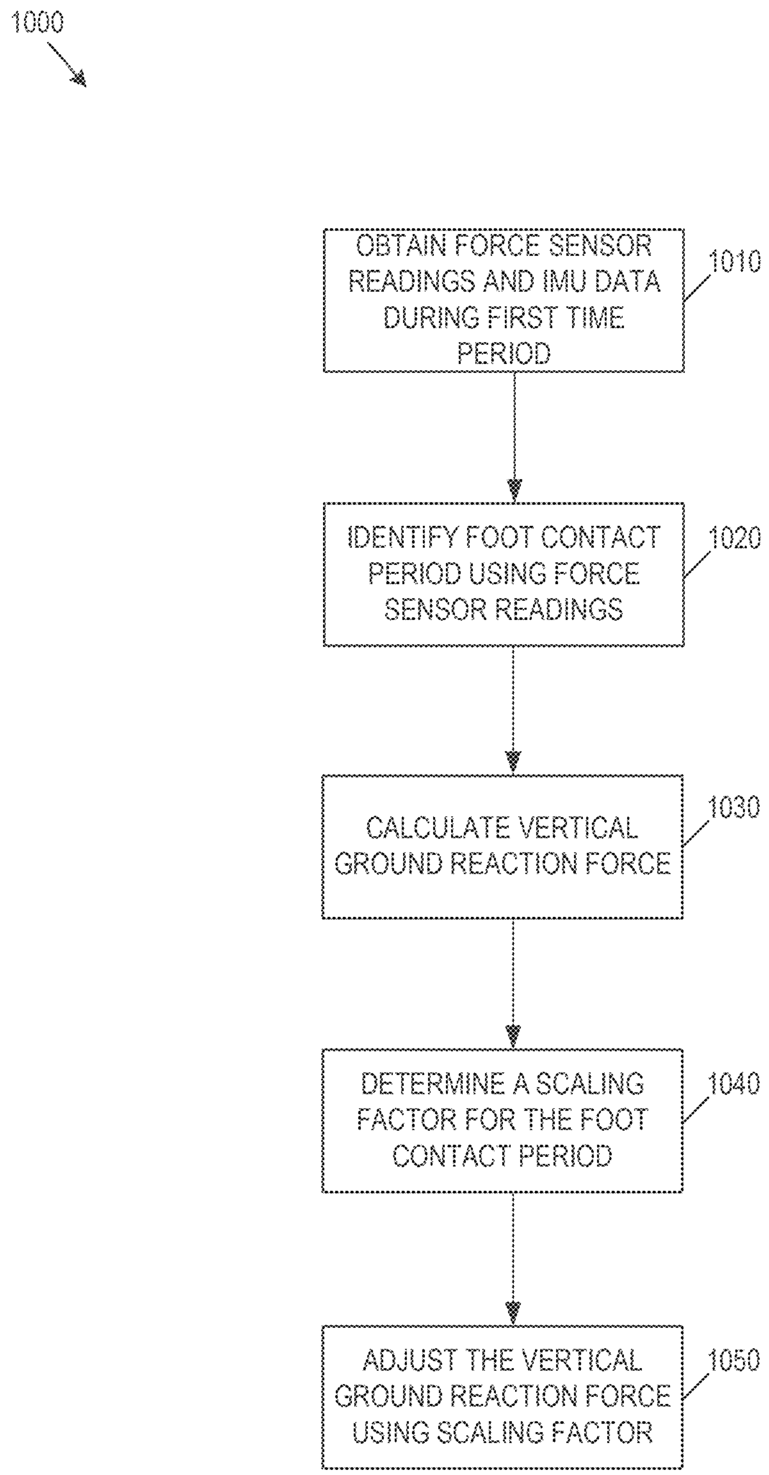
FIG. 10 is a flowchart illustrating an example of a method for determining a magnitude-corrected force signal using data from an inertial measurement sensor.

Referring now to FIG. 10, shown therein is an example method 1000 for determining a magnitude-adjusted ground reaction force using force sensor data from a plurality of force sensors positioned underfoot and IMU data from an inertial measurement unit. The method 1000 may be used with a plurality of sensors configured to measure human movement or human activity, such as sensors 106 and IMU 112. Method 1000 is an example of a method for determining a magnitude-adjusted ground reaction force in which IMU data is used to determine a scaling factor for a ground reaction force signal generated based on force sensor data from the plurality of force sensors.

At 1010, force sensor readings can be obtained from a plurality of force sensors. The force sensor readings can be acquired during a first time period.

Similar to step 310, the sensor readings can be obtained from a corresponding plurality of sensors. The plurality of sensors can include a plurality of force sensors positioned underfoot (i.e. underneath the foot) of a user performing a physical activity. The plurality of force sensors can be configured to acquire force sensor data.

The plurality of sensors may also include one or more inertial measurement units (also referred to as inertial measurement sensors) IMUs. Accordingly, the plurality of sensor readings acquired at 1010 can include IMU data received from the one or more inertial measurement units (IMUs). The IMU data can include acceleration data and angular velocity data.

Each inertial measurement unit (IMU) can be associated with the plurality of force sensors. For example, the IMU may be incorporated into the same wearable device as the plurality of force sensors. More generally, the IMU can be configured to collect IMU sensor data about a single foot of a user. This IMU sensor data can be acquired for the same foot for which the sensor readings were obtained from the plurality of force sensors.

The plurality of force sensors and the IMU can collect sensor data simultaneously while a user is performing an activity. The plurality of force sensors and the IMU can collect sensor data over a first time period. The first time period may be defined in various ways, as explained in further detail herein above with reference to step 310.

The sensor readings may be acquired over the course of a plurality of strides taken by a user. The sensor readings can be used to determine various data associated with individual strides. The plurality of strides can be identified using data from the sensor readings.

At 1020, a foot contact period can be identified based on the force sensor readings obtained at 1010. The foot contact period may be identified using various techniques, such as the example method 300 described herein above. Alternatively, IMU data (e.g. accelerometer data) may be used to identify the foot contact period.

As noted above, the sensor readings may be acquired over the course of a plurality of strides taken by a user. A corresponding foot contact period can be identified for each stride. Each foot contact period may be identified using various techniques, such as the example method 300 described herein above. Alternatively, IMU data (e.g. accelerometer data) may be used to identify the foot contact period.

At 1030, a vertical ground reaction force signal can be calculated for the foot contact period identified at 1020. The vertical ground reaction force signal can be calculated using the force sensor readings obtained at 1010. For example, the vertical ground reaction force signal can be calculated using the example method 1200 described herein below. Alternatively, the vertical ground reaction force signal can be determined based on a sum of the sensor-specific values from each force sensor in the force sensor readings obtained at 1010. Alternatively or in addition, the vertical ground reaction force signal may be calculated using data from an IMU in addition to using the force sensor readings obtained at 1010.

The sensor readings may be acquired as a time-continuous set of sensor readings. This may provide a time-continuous set of signal values that can be used to determine a time-continuous vertical ground reaction force signal. Depending on the nature of the sensors and the signal preprocessing performed, the time-continuous sensor data may be discretized, e.g. using an analog to digital conversion process.

At 1040, a scaling factor can be determined for the foot contact period. The scaling factor can be determined using the IMU data obtained at 1010 as well as the force sensor data obtained at 1010.

A mean vertical ground reaction force for the foot contact period can be calculated using the force sensor readings. Optionally additional inputs may also be used to determine the mean vertical ground reaction force, for instance as described in the example of method 1200 herein below.

The mean vertical ground reaction force may be determined as a mean value of the vertical ground reaction force signal determined at 1030. For example, the mean vertical ground reaction force may be determined according to:

$$vGRF_{mean} = \left(\sum_{i=FC}^{FO} vGRF_i\right) / (i_{FO} - i_{FC})$$

where $vGRF_{mean}$ represents the mean vertical ground reaction force, $vGRF_i$ represents a value of the vertical ground reaction force signal at time i, FC represents the foot contact time for the given stride, FO represents the foot off time for the given stride, and $i_{FO}$-$i_{FC}$ represents the number of time steps between the foot contact time and the foot off time.

An IMU mean vertical ground reaction force can also be determined for the foot contact period using the IMU data for the foot contact period.

The scaling factor can then be determined based on the mean vertical ground reaction force and the IMU mean vertical ground reaction force. For example, the scaling factor can be determined by dividing the IMU mean vertical ground reaction force by the mean vertical ground reaction force.

The IMU mean vertical ground reaction force may be determined in various ways. For example, IMU mean vertical ground reaction force can be determined using a prediction model that is defined to predict an IMU mean vertical ground reaction force in response to receiving the IMU data as an input.

The prediction model may be a machine learning model trained to predict the IMU mean vertical ground reaction force in response to receiving IMU data as an input. The IMU data can include acceleration data and angular velocity data based on acceleration and angular velocity readings measured by the IMU. For example, the IMU data can include a running speed of the user, a peak value of vertical acceleration, a peak value of fore-aft acceleration, and a peak value of a sagittal plane gyroscope signal during the foot contact period.

The IMU data (e.g. the running speed, peak vertical acceleration, peak fore-aft acceleration and peak sagittal plane gyroscope value) can be input to the machine learning model. The machine learning model can be trained to output IMU ground reaction force data (e.g. the IMU mean vertical ground reaction force) in response to receiving the IMU data as inputs. Accordingly, the IMU ground reaction force data associated with the plurality of sensor readings can be determined by the machine learning model.

The IMU ground reaction force data may be defined in various ways. For example, the IMU ground reaction force data can be defined as an IMU mean vertical ground reaction force. The machine learning model can be trained to output the IMU mean vertical ground reaction force for each stride based on the IMU data for the entire stride.

Alternatively or in addition, the IMU ground reaction force data can be determined as time-continuous IMU ground reaction force data. The time-continuous IMU ground reaction force data may be defined using a fully continuous time scale or a discretized time scale that includes time steps. The machine learning model can be trained to output time-continuous IMU ground reaction force data based on time-continuous input data (i.e. IMU data corresponding to each point in time or time step within a given stride). This may provide more granular data for feedback and analysis with the trade-off of requiring increased computational expense. This may also allow a scaling factor to be determined on a time-continuous basis across the stride—i.e. separate scaling factors can be determined for each time point within a single stride. In order to determine a time-continuous scaling factor, the vertical ground reaction force calculated from the force sensor data can also be generated as a time-continuous value.

Various different types of machine learning models may be used to determine the IMU mean vertical ground reaction force. For example, a linear model such as a regression model may be used.

Alternatively, a different type of machine learning model could be used to determine the IMU mean vertical ground reaction force, such as, for example a non-linear model such as a neural network.

The machine learning model can be trained using training data acquired from one or more users running or walking on a treadmill equipped with force measurement sensors while wearing a wearable device comprising a training IMU.

The training data can be defined to include the set of inputs (e.g. the IMU data) determined from IMU sensor data. The inputs can be determined based on training sensor readings from an IMU (as at 1010).

The training data can also include measured data representing the force output by a user. A training mean vertical ground reaction force can be determined using a treadmill equipped with force measurement sensors.

The training data can be collected from one or more users performing an activity. Once the machine learning model is trained using the training data, the machine learning model can be applied to determine the IMU mean vertical ground reaction force of the same or different users performing the same or different activities.

The training process may vary depending on the type of machine learning model being implemented. A regression model may be trained to determine the coefficients of a mean vertical ground reaction force prediction equation. For example, the machine learning model can be trained to determine the coefficients $C_1$, $C_2$, $C_3$, $C_4$, and $C_5$ of the equation:

$$C_1 * \text{speed} + C_2 * pACC_z + C_3 * pACC_y + C_4 * pGYR_x + C_5 = vGRF_{mean}$$

where speed represents a running speed of a given user, $pACC_z$ represents a peak of the absolute value of the vertical acceleration during a training foot contact period as measured by the training IMU, $pACC_y$ represents a peak of the absolute value of the fore-aft acceleration during the training foot contact period as measured by the training IMU, $pGYR_x$ represents a peak of the absolute value of the sagittal plane gyroscope during the training foot contact period as measured by the training IMU, and $vGRF_{mean}$ represents a training IMU mean vertical ground reaction force of the training data during the training foot contact period.

The regression model can be trained to determine the coefficients $C_1$, $C_2$, $C_3$, $C_4$, and $C_5$ using various regression techniques, such as a least squares regression or an optimization algorithm for example. Once trained, the machine learning model can be configured to determine the IMU mean vertical ground reaction force according to:

$$C_1 * \text{speed} + C_2 * pACC_z + C_3 * pACC_y + C_4 * pGYR_x + C_5 = vGRF_{meanIMU}$$

using the coefficients $C_1$, $C_2$, $C_3$, $C_4$, and $C_5$ determined through the training process.

Alternatively, with a neural network model, an optimization algorithm can be applied to optimize the connection weights between the neurons and between layers of the neural network model. The optimization algorithm may employ a cost function based on the difference between the training mean vertical ground reaction force and the model outputs calculated from the given IMU input data. The trained model can then be used, as at 1040, to determine the IMU mean vertical ground reaction force based on IMU data acquired by an IMU.

Different combinations of input data may be used to train and implement the machine learning model. For example, the machine learning model may be trained to receive 4 inputs, namely a speed value, a peak vertical acceleration value, a peak fore-aft acceleration value, and a peak sagittal plane gyroscope value.

In some cases, the input data may be determined as a single value for each stride. For instance, a single speed value, peak vertical acceleration value, a peak fore-aft acceleration value, and a peak sagittal plane gyroscope value can be determined for a given stride. The speed value may be determined as an average speed for that stride.

In some cases, the input data may include multiple values for each stride. For instance, the input data may be determined as time-continuous inputs that include multiple values at each time point or time step in a given stride.

Alternatively, a different number of inputs may be used. For example, a different number of inputs can be used where other inputs (e.g. mean acceleration in the z-direction, peak angular velocity in the y-direction, magnetometer data) are included in addition to, or in place of, the example inputs described herein above.

Alternatively or in addition, some of the inputs may be adjusted or modified. For example, mean acceleration values may be used as an input in place of peak acceleration values.

The IMU data may also be captured in various forms. For example, the IMU data may be collected using Euler angles and/or quaternions.

Alternatively, a peak vertical ground reaction force and IMU peak vertical ground reaction force may be used to determine the scaling factor in place of the mean vertical ground reaction force and the IMU mean vertical ground reaction force.

Alternatively, method 1000 may be applied with other components of the ground reaction force (other than the vertical ground reaction force), e.g. the anterior-posterior ground reaction force.

At 1050, the vertical ground reaction force signal (from 1030) can be adjusted using the scaling factor (from 1040). For example, the scaling factor can be applied to all of the vertical ground reaction force signal values in the vertical ground reaction force signal in the foot contact period. The adjusted vertical ground reaction force signal may also be referred to as a normalized vertical ground reaction force signal.

The scaling factor determined at 1040 can be a linear scaling factor. Accordingly, the vertical ground reaction force signal values may be scaled linearly to generate the normalized vertical ground reaction force signal.

As noted above, the sensor readings may be acquired over the course of a plurality of strides taken by a user. A corresponding foot contact period can be identified for each stride. The steps of calculating the vertical ground reaction force signal, determining the scaling factor, and adjusting the vertical ground reaction force signal using the scaling factor can be repeated individually for each foot contact period.

The adjusted vertical ground reaction force signal determined at 1050 can be output. This may provide a user with data representing the force applied by their foot when performing an activity like running or walking. The output data can provide the user with insight into their level of performance while performing movement or an activity.

The adjusted vertical ground reaction force signal can be output directly through an output device to provide a user with feedback on the activity being monitored. This may allow the user to continuously improve their force output while performing the activity. For example, the adjusted vertical ground reaction force signal may be transmitted to a mobile application on the user's mobile device (e.g. a processing device 108). Alternatively or in addition, the adjusted vertical ground reaction force signal may be stored, e.g. for later review, comparison, analysis, or monitoring.

The adjusted vertical ground reaction force signal can be used as an input to a game. In particular, the data may correspond to a certain foot gesture, and foot gestures may be used to control the game (like buttons on a game controller). In particular, gestures performed in real life may be recreated in a game. For example, the adjusted vertical ground reaction force signal that corresponds to a user running in real life may cause an avatar to run the same way in a game. Alternatively, gestures may not be recreated in a game, but may be used to execute controls in a game. For example, a step by a user in real life may serve to select an option in a game menu.

Gestures and user data (e.g. the adjusted vertical ground reaction force signal) and their corresponding actions may be pre-programmed into a game or may be programmed by users. For example, the game may have a preprogrammed heel tap gesture on the left foot that corresponds to an action in the game (e.g. selecting an option in a menu). However, in some cases, not all users are able to perform the heel tap gesture on the left foot (e.g. a user with no left foot). Instead, the user may be able to program their own foot gesture for the selection tool. The user may record another action (e.g. a heel tap on the right foot with a lower vertical ground reaction force (vGRF)) that replaces the preprogrammed gesture).

Virtual environments, objects, and avatars may be generated, with which a user using the system can interact. The virtual environment and virtual objects can be altered based on the movements, gestures, and adjusted vertical ground reaction force signals of users. Output devices (e.g. a television screen, a virtual reality headset, etc.) may be used to display the virtual environment to users. A user may visit a variety of virtual environments, including imaginary environments or environments that replicate real-life environments (e.g. Central Park, a friend's house, etc.). When a user moves around while wearing the carrier unit, they will move around in and interact with the virtual environment accordingly.

A gaming scaling factor may be applied to the adjusted vertical ground reaction force signal in a game. The gaming scaling factor may be an integer (e.g. 1, 2, 5, 10, etc.) or it may not be an integer (e.g. 0.2, 1.5, 2.6, 6.9, etc.). In one example, the gaming scaling factor may be 1. In this case, the adjusted vertical ground reaction force signal is applied equivalently in a game (i.e. a 1:1 scaling). For example, the adjusted vertical ground reaction force signal applied to the ground when an avatar stamps their foot in a game is equivalent to the adjusted vertical ground reaction force signal a user exerts on the ground in real life. In another example, the gaming scaling factor may be 5. In this case, the adjusted vertical ground reaction force signal is scaled 1:5 from real life to the game. In this case, the adjusted vertical ground reaction force signal applied to the ground when an avatar stamps their foot in a game is five times the adjusted vertical ground reaction force signal that a user applies to the ground in real life. Gaming experiences that are directly based on a user's data allow users to have a more realistic and immersive gaming experience than games that are not based on a user's biometrics (e.g. games played with buttons on a controller). Gaming scaling factors may allow for superhuman performance enhancements in a game. For example, an avatar whose adjusted vertical ground reaction force signal is scaled by a gaming scaling factor of 5 may be able to break through a glass floor when they stamp their foot in a game, but an avatar whose adjusted vertical ground reaction force signal is scaled by a gaming scaling factor of 1 may not be able to break through it.

The adjusted vertical ground reaction force signal may also be applied to different environmental factors in a game. For example, the gravity in a game can be changed. The gravity can be changed to that of another planet, such as the gravity of Mars. The adjusted vertical ground reaction force signal can be applied to the new environmental factors, so a user can understand how they might perform in a different environment. The performance of the user under the original conditions and the simulated conditions can be shown on a visual display.

The virtual environment can display or generate an avatar representing the portion of a user's body to which the carrier unit is affixed. For example, if the carrier unit is a pair of insoles, a user's feet may be rendered in the virtual environment. The skins and/or shoes applied to the feet in the virtual environment may depend on the user's outputs, or they may be selected by the user. For example, if a user's adjusted vertical ground reaction force signal indicates that they are performing a leisurely task, they may be depicted wearing flip flops in the game environment. As another example, if the adjusted vertical ground reaction force signal of a user indicates that they are running, they may be depicted wearing sneakers in the game environment. Special objects and/or abilities may be associated with the virtual skins and shoes. For example, virtual lasers or swords may extend from the virtual shoes that can be used to fight villains in a game. As another example, virtual shoes may contain a special feature, where they can build up energy if a user performs a certain task or reaches certain goals. The built-up energy can be used to create a burst of power in a game involving a cyclic, step-based activity (e.g. a running game).

Alternatively, the virtual environment can display or generate an avatar for the user's entire body. The appearance of the avatar's body may depend on the user's adjusted vertical ground reaction force signal. For example, if large vertical ground reaction forces are frequently recorded for a user, it may be inferred that they regularly perform high-intensity physical activities such as running, and their avatar may appear lean. An avatar's appearance may also be location dependent. For example, if a user lives in a warm, dry climate, the avatar may be depicted in shorts and a t-shirt, with dried sand on their skin. Alternatively, if a user lives in the Arctic, their avatar may be depicted in a parka and furry boots. There may be location-dependent virtual items that can be unlocked. For example, if a user travels to another country in real life, they may unlock a special running shoe from that country. The carrier unit may contain a GPS system or another location-sensing system to enable the location-dependent items and features to be unlocked.

The adjusted vertical ground reaction force signal may also be used to model the dynamics of virtual objects and/or surroundings within a game. For example, if an avatar jumps on a trampoline in a game, the deflection of the trampoline in the game and the jump height of the avatar will be affected by the vertical ground reaction force applied to the ground by a user jumping in real life. The appearance of the surroundings will change based on the avatar's jump height (e.g. the higher the avatar jumps, the more sky (and less ground) that will be shown in the surroundings).

Additionally, the adjusted vertical ground reaction force signal may be used to control a character in a lifestyle game. These games may require a user to virtually embody a certain lifestyle and complete tasks involved with the lifestyle. For example, a user may embody the lifestyle of an Olympic runner in a game. The user will be required to train like an athlete, and the adjusted vertical ground reaction force signal can be used to determine if the user has successfully completed the training. They may also be required to complete other tasks relating to the lifestyle of an Olympic athlete, such as taking rest days, taking part in competitions, achieving sponsorships, going on press tours, going grocery shopping, etc.

The system may also contain safety features to prevent users from injuring themselves on their real life surroundings while gaming. Safety features may be especially important for gaming with virtual reality headsets, where vision is obstructed. One safety feature that may be included in the carrier unit is sensors and/or software that can detect potential or recent collisions of a user with surrounding objects. In response to a detected collision, the system may pause the game to check on the user using a pop-up window. For example, wherein the carrier unit is an insole, software for the Bluetooth system may detect if a user's pair of insoles is in close proximity to another user's pair of insoles. The system may alert the users that they are getting too close to each other and are at risk of a person-to-person collision. In a further example, the system may have a feature where users can measure out a safe playing area. The safe playing area is a real life zone in which a user may safely participate in a game, without risk of collision with surrounding objects. Before a gaming session starts, a user may be asked to walk around the safe playing area, which is recorded in the system. While playing the game, the user may receive feedback and alerts on where they are within the safe playing area. The user's position in the safe playing area may be shown on a visual display on the output or processing device and/or they may receive auditory alerts, visual alerts, tactile alerts, or some combination thereof to indicate they are getting close to or have gone past the edge of the safe playing area.

The system may be paired with other carrier devices in gaming scenarios. For example, the insoles may be paired with other wearable devices, such as wrist-worn IMUs. A gaming platform comprising multiple wearable game controllers at different locations on the body can encourage users to engage with a game using their full body, which may increase their workout and fitness during a game. The system may also be paired with fitness equipment. For example, the insoles can be paired with a treadmill for a running game. The incline of the treadmill can change in response to different virtual terrains (e.g. running up a virtual mountain), and the user's adjusted vertical ground reaction force signal, as determined from the insoles, can determine how they are performing in the game. Visual display carrier units, such as VR headsets, smart glasses, and smart goggles, may also be paired with the insoles to increase the immersivity of games.

The system may also contain additional sensor types, whose data can be used to augment gaming experiences. In particular, temperature sensors may provide various advantages for health, athletic, and gaming applications. The system may include one or more temperature sensors used to measure body or environmental temperature. In a first example, one or more temperature sensors (e.g. thermistors) may be included in a flexible printed circuit within the bulk of the insole. The one or more temperature sensors can detect temperature changes from the body. The temperature changes may be used in an algorithm that adjusts other sensor (e.g. force sensor) readings to account for temperature drift. Alternatively, the one or more temperature sensors may be used to measure the body temperature of users for health and gaming calculations (e.g. calorie burn calculations or task readiness calculations). In another example, the one or more temperature sensors may be affixed to the outside of the shoe or at other locations away from a user's body to determine the external temperature. The external temperature may be used in gaming to send safety messages and notifications to users (e.g. if the external temperature is hot, a user may receive a notification suggesting they hydrate more frequently). The external temperature may also be used to adjust health and gaming calculations and may be used to adjust the virtual environment in a game (e.g. if the external temperature is hot, the game may place the user in a virtual desert).

Additionally, the adjusted vertical ground reaction force signal may contribute to scoring in a game. For example, a performance score may be calculated from the adjusted vertical ground reaction force signal. If a user's adjusted vertical ground reaction force signal indicates that they are regularly exercising or increasing their exercise load and/or intensity, the number of points they earn in a game may increase. Increased points earning may incentivize users to increase their physical activity and improve their technique during gaming. The adjusted vertical ground reaction force signal may be stored, e.g. for later review, comparison with other users, analysis, or monitoring.

One or more normalization factors may be defined to allow performance scores to be determined fairly for different users. Normalization factors may be applied to account for factors such as mass, weight, age, gender, natural athletic ability, game skill, other physical characteristics, or some combination thereof.

For example, wherein the carrier unit is an insole containing force sensors, vertical ground reaction forces will be larger for heavier users than lighter users, as heavier users will naturally apply more force to the ground. However, normalization factors allow users of different sizes to obtain the same performance scores for performing equivalent activities.

The calculation of performance scores can also include modification factors such as multipliers and bonuses for successful completion of objectives including streaks, skillful movement combinations, and/or other unique game experiences such that performing the same in-game action may not yield the same performance scores each time.

The performance scores and/or the adjusted vertical ground reaction force signal may also be used as metrics for zone training. Zone training is a type of athletic training which encourages users to keep their metrics within a range or "zone" of values over a predetermined period of time (e.g. the length of a game). Users may be shown their position in a zone in real-time and may be rewarded for staying within the zone and/or penalized for leaving the zone. For example, a user may be given a ground reaction force symmetry zone to stay within for a running game. During the game, the user will be encouraged to keep their ground reaction force symmetry in the designated zone to achieve maximum points.

The performance scores and/or the adjusted vertical ground reaction force signal can also be used to determine other gaming-related metrics for a user. For example, a user can be associated with one or more user levels. The user levels generally refer to the experience of a user within a game. User levels may be used to compare users to one another, or to establish progression in fitness and experience over time.

The performance scores and/or the adjusted vertical ground reaction force signal may also be used to assign and to track progress towards training goals within a predetermined time period. For example, based on a user's performance score over one week, a training goal can be generated for the user to achieve the same or a greater performance score the subsequent week. The performance scores can then be tracked the subsequent week to determine the user's percentage of progress towards achieving the training goal.

Training goals can relate to accumulated performance scores, system usage metrics and/or adjusted vertical ground reaction force signals that should be achieved in a predetermined time period (session, day, week, month, year, season, etc.) or instantaneous values (i.e. a rate) that should be achieved at a certain point in time. Training goals may be suggested by the processing system based on previous activities, be chosen by the user, or be presented as part of a challenge from another user or group of users. Suggested training goals can become increasingly targeted for users as additional sensor data is collected by the system over time.

Training goals can be directed toward weight loss. Wherein the carrier unit is an insole containing force sensors, body weight or mass can be measured by the insoles. Alternatively, an external device may be used to measure body weight or mass and transmit the values to the input device 102, remote processing device 108, or cloud server 110. If a user has a training goal to lose a certain amount of weight, the processing system may recommend certain activities to help them accomplish their goal. In particular, the processing system may recommend fitness-related games that can be played with the carrier unit. For example, for an overweight user, the system may suggest low impact, high calorie burning games. The system may create a fitness-based game schedule for the user to follow, to encourage increased activity and intensity as the user's body weight or mass decreases (i.e. as their percentage of progress towards achieving the training goal increases). The system may also include a digital coach to help the user in their weight loss journey. A user may participate in virtual weight loss groups and/or rooms to encourage participation and support through interacting with other users with similar training goals. Weight loss may also be encouraged through badges, virtual gifts, streaks, and other virtual achievements.

Training goals may also be directed toward education. Specific games and activities may integrate educational concepts (e.g. a jumping game that helps users learn a new language). The same social interactions and virtual achievements in the weight loss example may also apply to a user's journey with an educational goal.

Additionally, the adjusted vertical ground reaction force signal may also be used to assess a user's technique when performing an activity or movement (i.e. their quality of movement). Wherein the carrier unit is an insole containing pressure or force sensors, a user's adjusted vertical ground reaction force signal may be recorded and stored in the system memory for an activity, such as running. As further data is collected for the user, the system may compare previous data against new data to determine differences in technique to notify the user of fatigue or of a potential injury. Alternatively, the system may compare data contralaterally (i.e. between opposing limbs) to determine differences in technique. To assess technique, a machine learning model may be trained on data that includes both "correct" and "incorrect" versions of an activity. In implementation, the model can then classify an activity as "correctly" or "incorrectly" performed. Alternatively, the model can be trained on data that includes rankings (e.g. by a clinician or sports scientist) on technique of certain activities (e.g. a 0 to 5 ranking, where 0 indicates that an activity was poorly executed and where 5 indicates that an activity was perfectly executed). In implementation, the system can reject exercise tasks below a certain ranking and/or output the ranked value. In another example, technique can be assessed based on conditions or restrictions set for each activity. For example, if running gait is the task being assessed, there may be a cut-off vertical ground reaction force asymmetry used to assess movement quality (e.g. no more than 5% difference between feet). A user's adjusted vertical ground reaction force signal can be used to determine if the condition was met. If the user does not meet the condition or restriction, their technique may be deemed unacceptable.

In a further example, the adjusted vertical ground reaction force signal may also be used to determine a user's "readiness" to participate in a game or activity. At either intermediate or specified points in time, an exercise may be given to a user to assess their state of "task readiness". The exercise may include a jump, squat, balance, sprint, series of steps, or another physical exercise. The exercise may be included as part of a game or challenge or may be separate from game play. Task readiness refers to a user's ability to perform a task at a moment in time. Injury potential, technique, and/or fatigue state of the user may be incorporated in a task readiness score or may be pulled out of the task readiness score and displayed as a separate score. The task readiness, injury potential, technique, and/or fatigue state scores may be recorded over time and may be displayed in a metrics report. The metrics report may be used to quantify improvements and overall fitness. The real-time readiness scores of the user may be reported to the user on the input device 102, remote processing device 108, or cloud server 110. For example, on a display of the remote processing device, a poor task readiness score may be reported as a red bar, an average task readiness score as a yellow bar, and a good task readiness score as a green bar in the top corner of the display. The task readiness feedback may alert the user to a deteriorating quality of their movements, which can be used to make an informed decision on continuation of game play. The task readiness scores may be used to recommend games that are appropriate for the user's physical state (e.g. their fitness level) at a certain point in time. For example, consistently high task readiness scores over a period may indicate that a user should play more advanced games to improve their fitness level. The system may recommend more advanced games to the user or higher-level players to compete against. The task readiness scores may also be used to recommend rest periods for the user or to coach the user through auditory means, visual means, tactile means, or some combination thereof. For example, a virtual coach may be used to instruct the user on how to improve movement quality to gain more points, prevent injury, or achieve another goal in the game.

A virtual coach may be used to assist a user with meeting their training goals. The virtual coach may be trained through machine learning or other algorithms to give suggestions, notifications, and encouragement to the user relating to the training goal. Alternatively, a personal trainer, physiotherapist or other expert in the field may assess a user's historical outputs to develop and suggest training goals and paths to achieving training goals within the game.

Feedback may also be provided to users based on their adjusted vertical ground reaction force signal, their training goals, their task readiness, and their technique. For example, if a user goes on a run and the system calculates significant bilateral asymmetry for the vertical ground reaction force between the user's left and right foot, they may be provided with feedback to correct the asymmetry. Feedback may be provided in the form of haptic feedback, such as with vibrational motors embedded in the carrier unit.

Feedback may also be provided in the form of an audio signal. A user's adjusted vertical ground reaction force signal may be sonified and played in real time or post-activity for the user. For example, if a user goes on a run, their adjusted vertical ground reaction force signal can be sonified and played in real time. The user can then sonically identify changes in their adjusted vertical ground reaction force signal, and they can make real time adjustments to their running technique to maintain or improve their performance. Signal processing techniques may be used to increase the effects of sonification. For example, signals may be amplified, such that the sonification spans a broader range of tones than an unamplified signal, which may make it easier for users to identify changes in tone. Signals may also be layered. For example, the signals from the right and left foot may be added together prior to sonification, or the sonifications from the right and left foot may be played simultaneously. Signals may also be filtered to minimize noise, which may be distracting to a user once the signal is sonified. Visual feedback may also be provided by the system.

Users may review their feedback and data (e.g. visualizations, sonifications, and haptics) during or after an activity. Real-time feedback may encourage users to continue to engage with the activity at a higher level of intensity or to increase their intensity. Post-activity data reviews may encourage users to understand their activity and movement statistics to prepare for improvements in the next activity.

Sonification of the adjusted vertical ground reaction force signal may also be used for artistic purposes. For example, the signal may correspond to certain musical features, such as notes, instruments, tempos, and volumes. In a particular embodiment, the magnitude of the adjusted vertical ground reaction force signal may control the volume of a track. As the vertical ground reaction force increases, the volume may increase. Users may work together to create music. For example, if two users go running, one user's sonification may create a melody and the other user's sonification may create a harmony. In this regard, users can generate music in real time with their bodies. Similarly, users, such as DJs, may be able to mix music in real time. For example, a DJ may run on a treadmill at a concert while wearing the insoles, and by changing their running technique, they can cue tracks and increase or decrease the speed of tracks.

The adjusted vertical ground reaction force signal may also be used to create visualizations. Visualizations may be data driven (e.g. graphs) or artistic visuals (e.g. data-inspired paintings). For example, a user may be able to "paint" with their insoles by applying force in various areas of the foot and using foot gestures to create different "brush strokes". In another example, a large display screen may be used to show a user's adjusted vertical ground reaction force signal while they are running, racing, or gaming.

Additionally, information may be communicated to and/or between users through visual, audio, or haptic cues. For example, the system may send a haptic cue to a user's insoles to prompt them to complete a daily challenge based on the adjusted vertical ground reaction force signal. The results of their daily challenges may be compared with the results of other users. Alternatively, if cues are sent between users, a first user in a game may challenge a second user in a game to perform an activity by sending a haptic signal to the second user's carrier device. The communicated information may be based upon the two users' adjusted vertical ground reaction force signals. For example, the first user may send a haptic cue to the second user to challenge them to a run, where the user with the best vertical ground reaction force symmetry during the run will be declared the winner.

Users may also be able to create levels or challenges for other users based on their adjusted vertical ground reaction force signal. For example, in an impersonation game, a first user may be challenged to recreate the walk of a second user (such as a friend or celebrity), by replicating their adjusted vertical ground reaction force signal.

The adjusted vertical ground reaction force signal may be displayed on an output device, as part of the remote processing device 108 or cloud server 110. A user may also be able to interact with a visual display via an interactive medium (e.g. a touchscreen) on the output device. Examples of data visualizations that may be provided on the visual display based on sensor readings and/or derived values of a user using the carrier unit include foot pressure maps to show the pressure distribution on the insoles, foot pressure maps to show the movement of the center of pressure, points displays (e.g. performance score), pop-up notifications of errors in movement, pop-up notifications with suggestions to correct the movement, graphs showing changes in data over time, colour codes (e.g. different colour pop-ups for different performance scores or gestures), footprints whose shapes or depths are estimated based on the sensor readings and/or derived values, cumulative displays (e.g. accumulation of peak vertical ground reaction forces, which, when a certain level is reached, may be used to provide a burst of power for an avatar in a game), or some combination thereof. The data visualizations may be altered or enabled or disabled by users, with toggles, buttons, or other actions.

A user's output device may also display information (such as names, adjusted vertical ground reaction force signals, etc.) of other users in the same area using the same type of system. Carrier units may contain GPS systems or other location-sensing systems to enable viewing information of other users in the same area. Location-sensing may provide opportunities for virtual social interactions between users. Examples of social interactions include gift exchanges, meet-ups in virtual rooms, messaging, game challenges, cooperative games, competitive games, combination games (i.e. games with a competitive and cooperative aspect), tournaments, leaderboards (e.g. for age groups, geographic locations, specific games, etc.), and the ability to "follow" and/or "friend" other users (i.e. adding users to a list of "friends" on the system platform). Other social interactions known in the art, but not listed here, may also be included.

Virtual meeting rooms are digital areas where users may send messages or chats with one another, play games together, and participate in social interactions with other users. The system may have virtual meeting rooms available, or users may create and design their own virtual meeting rooms. The owner of a virtual meeting room may allow open access to the virtual meeting room, or they may restrict access to certain users. The owner may invite users to join their virtual meeting room.

Social interactions may also include competitive races against the adjusted vertical ground reaction force signal of the same user (i.e. their previous scores), other users, a "computer", celebrities, and/or professionals. For example, a user may enable a "ghost" mode, where they can view their previous performances when repeating an activity, to compete against themselves. For example, in a game where a user is required to perform a jump, they can view a "ghost" of their avatar's best performance while repeating the activity, along with a display window showing the ghost's adjusted vertical ground reaction force signal, to encourage them to match or improve the performance. In another example, in a running game, the user may enable "ghost" mode to view the adjusted vertical ground reaction force signal of a 5000 meter professional runner, who recorded their adjusted vertical ground reaction force signal in the game for other users to copy. The user can work towards matching the professional runner's data to improve their own performance. In another example, a professional runner may create a virtual competition where users can compete against the professional for a month-long running challenge. The participating users' adjusted vertical ground reaction force signals can be compared to the professional's adjusted vertical ground reaction force signal to determine if any of the users beat the professional. Users who participate in and/or win the challenge may receive a virtual reward.

The method 1000 generally describes the process of determining an adjusted vertical ground reaction force signal for one leg. Optionally, method 1000 may be applied to determine the adjusted vertical ground reaction force signal for both of a user's legs, based, respectively, on data (e.g. force sensor readings and IMU data) collected for each leg. Method 1000 may be performed concurrently on the data collected for each leg in order to provide a user with real-time feedback of the adjusted vertical ground reaction force signal generated by each leg.

Figure 11:
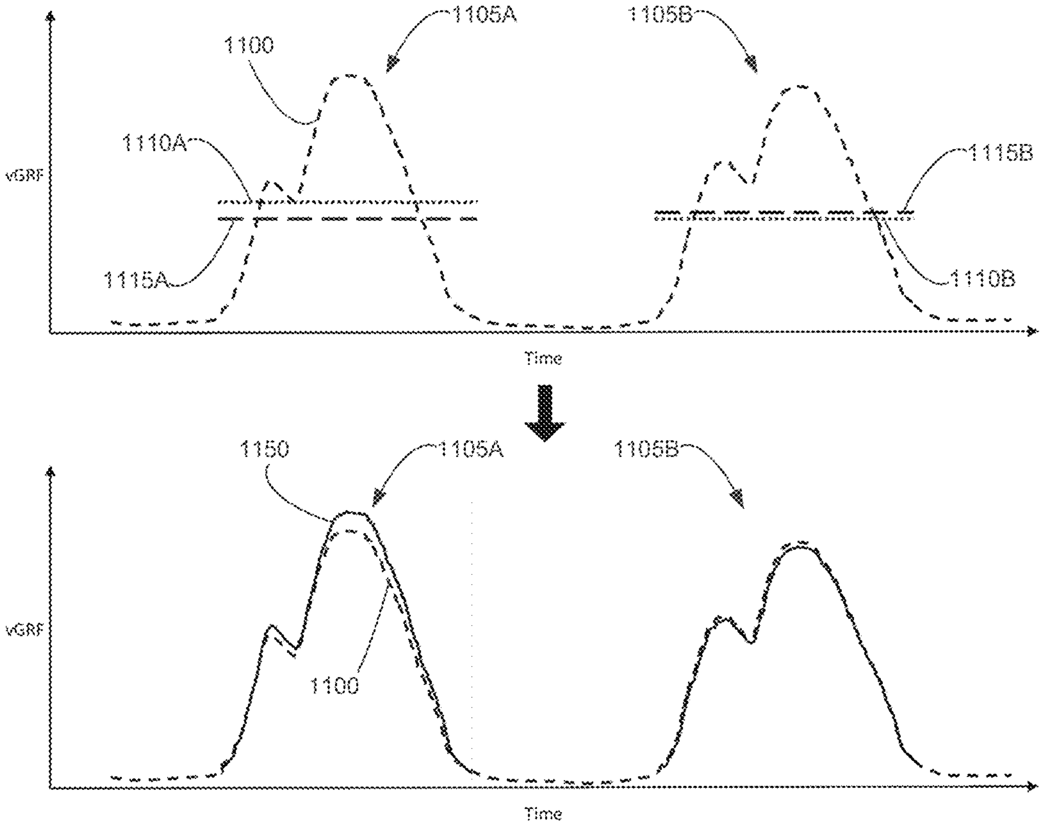
FIG. 11 is a plot illustrating an example of a magnitude-corrected force signal according to an example implementation of the method shown in FIG. 10.

FIG. 11 illustrates an example plot of an initial vertical ground reaction force signal 1100 (top plot) and a plot of an adjusted vertical ground reaction force signal 1150 (bottom plot). The adjusted vertical ground reaction force signal 1150 is illustrated after applying an implementation of method 1000.

FIG. 11 illustrates vertical ground reaction force signals over the course of two strides 1105A and 1105B. For the left-hand stride 1105A, a linear scaling factor was determined using an implementation of method 1000 by dividing the IMU mean vertical ground reaction force 1110A by the mean vertical ground reaction force 1115A determined from the force sensors. For the right-hand stride 1105B, a linear scaling factor was also determined using the implementation of method 1000 by dividing the IMU mean vertical ground reaction force 1110B by the mean vertical ground reaction force 1115B determined from the force sensors. The adjusted vertical ground reaction force signal 1150 is shown after scaling the signal data for the respective strides 1105 using the corresponding linear scaling factors.

Method of Determining Ground Reaction Force Data

The following is a description of a method of determining ground reaction force data that may be used by itself or in any combination or sub-combination with any other feature or features disclosed including the system for analyzing force sensor data, the method of identifying foot contact events, and the method for correcting the magnitude of a ground reaction force signal.

Measuring the ground reaction force resulting from a user performing an activity is an important biometric for monitoring human movement. Traditionally, ground reaction forces have been measured in laboratory settings using force plates and force plate-equipped treadmills. While some methods have been developed for measuring ground reaction forces without the use of force places, these methods often provide low accuracy results, are unable to predict more than one direction of ground reaction force, or are restricted to monitoring walking data.

In accordance with this aspect, a method of determining a ground reaction force is provided. Force sensor data is collected from a plurality of force sensors positioned underfoot over a first time period. A user mass, user speed and user slope can be obtained corresponding to the first time period. The force sensor data can be used along with the user mass, user speed and user slope to determine ground reaction force data with improved accuracy. The ground reaction force data can include multiple components of the ground reaction force (i.e. ground reaction force data corresponding to multiple directions).

To determine the ground reaction force data, the force sensor data, user mass, user speed and user slope can be provided as inputs to a machine learning model trained to predict multiple components of the ground reaction force. The machine learning model can be trained to output a corresponding vertical ground reaction force signal and a corresponding anterior-posterior ground reaction force signal.

IMU data from one or more IMUs can be used to determine one or more inputs to the machine learning model. For example, the slope and/or the user speed may be determined wholly or partially using IMU data. These IMU-derived inputs can be provided to the machine learning model in conjunction with the force sensor derived inputs in order to determine the ground reaction force data for the user.

Figure 12:
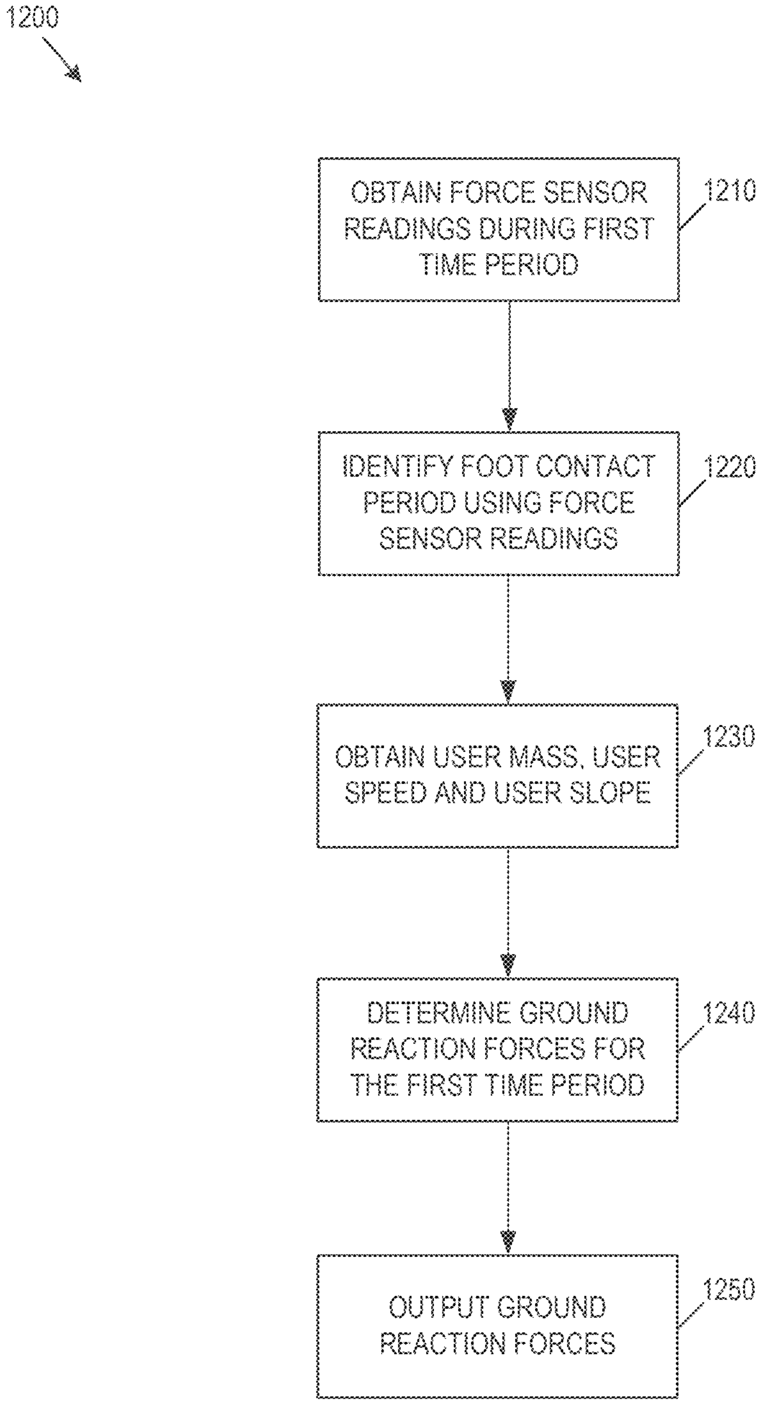
FIG. 12 is a flowchart illustrating an example of a method for determining a ground reaction force.

Referring now to FIG. 12, shown therein is an example method 1200 for determining ground reaction force data using force sensor data from a plurality of force sensors positioned underfoot. The method 1200 may be used with a plurality of sensors configured to measure human movement or human activity, such as sensors 106. Method 1200 is an example of a method for determining ground reaction forces in which a machine learning model can be used to determine the ground reaction force data based on sensor readings acquired from the plurality of force sensors.

At 1210, force sensor data can be obtained from a plurality of force sensors. The force sensor readings can be acquired during a first time period.

The force sensor data can be obtained for a plurality of specified foot regions. Each force sensor 106 in the plurality of force sensors can be assigned to a corresponding foot region 220. The force sensors in a sensor unit can be separated into a plurality of foot regions in various different ways. In some cases, the number of foot regions may be determined based on the sensor granularity of the sensing unit being used.

In the example shown in FIG. 2, the sensing unit 200 has been separated into five different foot regions 220*a*-220*e* in the anterior-posterior direction. Separating the force sensor data into five (5) specified foot regions may broaden the applicability of method 1200 to a variety of different force measurement systems. However, it should be understood that the number and configuration of foot regions can vary in different implementations of method 1200.

At 1220, at least one foot contact period can be identified within the first time period. The at least one foot contact period can be identified using the force sensor data acquired at 1210.

The foot contact period may be identified using various techniques, such as the example method 300 described herein above. Alternatively, IMU data (e.g. accelerometer data) may be used to identify the foot contact period.

As noted above, the sensor readings may be acquired over the course of a plurality of strides taken by a user. The sensor readings can be used to determine various data associated with individual strides.

A corresponding foot contact period can be identified for each stride. Each foot contact period may be identified using various techniques, such as the example method 300 described herein above. Alternatively, IMU data (e.g. accelerometer data) may be used to identify the foot contact period.

At 1230, a user mass, user speed, and user slope can be obtained. The user mass, user speed and user slope can be associated with the force sensor data for the first time period.

The user mass reflects the mass of the user performing the movement or activity being monitored. The user mass can be associated with the user generating the sensor readings captured by the force sensors and inertial measurement units. The user mass can be considered constant across each of the strides.

The user mass may be determined in various ways. Typically, the user mass can be determined prior to the movement or activity being monitored. For example, user mass may be measured using the force sensors underfoot of a user (e.g. as part of an initial calibration process). Alternatively, mass may be measured using a separate mass-measurement device such as a scale. In some cases, mass may be input manually, e.g. by a user interacting with an application on processing device 108. In some cases, determining the user mass may require converting the user's measured weight to a mass value.

The slope value and running speed value may be determined using the sensor readings acquired at 1210. Alternatively or in addition, one or both of the slope value and the running speed value may be determined based on data acquired from external devices, such as a treadmill on which a user is running.

Providing the slope value as an input to the machine learning model may allow the ground reaction force to be determined for a user over a variety of slopes or inclines. The slope value may be determined in various ways. For example, where a user is running or walking on a treadmill, the slope value may be determined based on the incline setting of the treadmill. The incline setting of the treadmill may be determined automatically, e.g. by connecting a processing device 108 to the treadmill using a wired or wireless communication interface and accessing the incline setting through the connection (e.g. through an application distributed in association with the treadmill). Alternatively, the incline setting may be input by a user, e.g. through an application running on processing device 108.

Alternatively, the slope value may be determined based on inertial measurement data received from an inertial measurement sensor. The inertial measurement sensor may be provided by an input unit 102 worn by a user (e.g. as part of a wearable device in the form of a sock, shoe or insole).

The slope value may be determined from the inertial measurement data in various ways. For example, the slope value may be determined by estimating a step height value for each stride. The step height may be determined by integrating the stride velocity (determined from the inertial measurement data) over the corresponding stride period. The result of the integration provides a stride displacement that includes components in each of the x, y, and z directions. The vertical component $\Delta d$, and horizontal component $\Delta d_y$ of the stride displacement may be used to determine the slope value 0 according to:

$$\tan\theta = \frac{\Delta d_z}{\Delta d_y}$$

Determining the slope value by estimating a step height value may be particularly desirable for users who are moving at lower speeds (e.g. walking).

Alternatively, the slope value may be determined by estimating a gravity vector value associated with the stride. A foot flat time can be identified for the stride. The direction of the gravity vector can be determined from the inertial measurement data. The direction of the gravity vector at the foot flat time can then be used to determine the slope value.

Determining the slope value based on the gravity vector value can include an initial calibration process in which the inertial measurement data is calibrated with the user's foot on flat ground. The difference in orientation between the gravity vector during the IMU calibration data and the gravity vector determined at the foot flat time during the stride can then be used to determine the slope value.

The method for determining the slope value may be selected based on user-specific calibration data provided to a processing device 108. In some cases, the method used to determine the slope value may be selected based on the foot strike pattern for a given user.

Certain foot strike patterns may make it more difficult to determine the foot flat time. For example, forefoot strike runners may not go through a foot flat time during a stride. In such cases, determining the slope value based on a gravity vector value may be less accurate. Accordingly, an alternative method of determining the slope value may be selected for users identified as forefoot strike runners.

Alternatively or in addition, the slope value may be determined based on force sensor data from the plurality of force sensors. For example, heel-strike runners experience less force in the heel region while running uphill as compared to running on flat ground. Accordingly, changes in the slope value may be determined by identifying trends in the force values. The changes in the slope value may be used to determine the slope value, for instance based on an initial calibration when running on flat ground. For example, the slope value may be determined using a machine learning model trained using known slope values (e.g. from training data acquired while a user is running on a treadmill) and force values for a user wearing insoles equipped with force sensors.

A separate slope value may be determined for each stride.

The running speed value may be determined in various ways. For example, where a user is running or walking on a treadmill, the running speed value may be determined based on the speed setting of the treadmill.

Alternatively, the running speed value may be determined based on sensor data received at 1210. As noted above, a plurality of strides can be identified using data from the sensor readings. Each stride may be identified based on times when the user's foot first contacts the ground (a foot-contact time) and/or times when the user's foot leaves the ground (a foot-off time).

Each stride can be defined to correspond to a stride period. The stride period generally refers to the time period over which a single gait cycle extends. The endpoints of the stride period may vary. For example, the stride period can be defined as the length of time between adjacent foot-contact times. Alternatively, the stride period can be defined as the length of time between adjacent foot-off times.

For each stride, the running speed may be determined based on a stride time and a stride length of the stride period corresponding to that stride. The running speed can be determined by dividing the stride length by the stride time.

The stride time and stride length may be determined using the sensor data acquired at 1210. For example, the stride time can be identified as the length of the corresponding stride period (e.g. the length of time between adjacent foot-off times or the length of time between adjacent foot-contact times).

A stride velocity can be determined using accelerometer data from the IMU. The accelerometer data can be integrated over the stride period to obtain the velocity. In some cases, the accelerometer data may need to be transformed to a global reference frame prior to integration. The accelerometer data can be transformed to a global reference frame based on the angle of the user's foot when the accelerometer data is acquired. The foot angle can be identified using a foot flat time determined for the stride and for the subsequent stride. Each foot flat time can be identified as a time of minimum gyroscope energy (as determined from gyroscope data received from the IMU) or as a time of maximal plantar force as determined from the force sensor readings.

The foot angle can then be determined based on integrated angular velocity data from the foot-contact time to the foot flat time of the subsequent stride (i.e. from the foot contact-time of the stride, past the foot-contact time of the subsequent stride to the next foot-flat time). The accelerometer data can then be transformed to the global reference frame based on the foot angle. The stride velocity can then be determined using the transformed accelerometer data.

Once the stride velocity has been determined, it can be used to determine the stride displacement. The stride velocity can be integrated over the length of time between adjacent foot contact periods (e.g. from one foot-contact time to the next) to determine the corresponding stride displacement. The stride length can then be determined based on a combination of the directional components of the stride displacement. The directional components of the displacement can be root-summed-squared to calculate the stride length.

A separate running speed may be determined for each stride.

At 1240, ground reaction force data can be determined for each foot contact period. The ground reaction force data can include a vertical ground reaction force signal and anterior-posterior ground reaction force signal. The ground reaction force data can be determined based on the user mass, the user speed, the user slope (from 1230), and the force sensor data (from 1210) for the plurality of specified foot regions during the corresponding foot contact period.

The ground reaction force data may be determined by inputting the user mass, the user speed, the user slope, and the force sensor data to a prediction model configured to output the corresponding vertical ground reaction force signal and the corresponding anterior-posterior ground reaction force signal. The prediction model may be a machine learning model trained to output the corresponding vertical ground reaction force signal and the corresponding anterior-posterior ground reaction force signal in response to receiving the user mass, the user speed, the user slope, and the force sensor data as inputs. The machine learning model can be trained using a vertical ground reaction force signal and an anterior-posterior ground reaction force signal measured by a force-instrumented treadmill. Accordingly, the ground reaction force data associated with the plurality of sensor readings can be determined by the machine learning model.

The ground reaction force data may be defined in various ways. For example, the ground reaction force data may be defined to include a vertical ground reaction force signal and an anterior-posterior ground reaction force signal. The ground reaction force data can be determined as time-continuous ground reaction force signals. The time-continuous ground reaction force data may be defined using a fully continuous time scale or a discretized time scale that includes time steps. The machine learning model can be trained to output the time-continuous ground reaction force data based on the user mass and the force values, slope value, and running speed value corresponding to each point in time or time step within a given stride.

Alternatively or in addition, the ground reaction force data can be defined to include a medial-lateral ground reaction force signal. The machine learning model can be trained to output the corresponding medial-lateral ground reaction force signal in response to receiving the user mass, the user speed, the user slope, and the force sensor data as inputs.

Alternatively or in addition, the ground reaction force data can be defined to include the free moment of the ground reaction force. The machine learning model can be trained to output the corresponding free moment of the ground reaction force in response to receiving the user mass, the user speed, the user slope, and the force sensor data as inputs.

Various different types of machine learning models may be used to determine the ground reaction force data. A non-linear machine learning model such as a neural network model can be used to determine the ground reaction force data. For example, the neural network may be a recurrent neural network. Non-linear machine learning models may provide greater accuracy in processing time-continuous data as compared to linear machine learning models.

Figure 13:
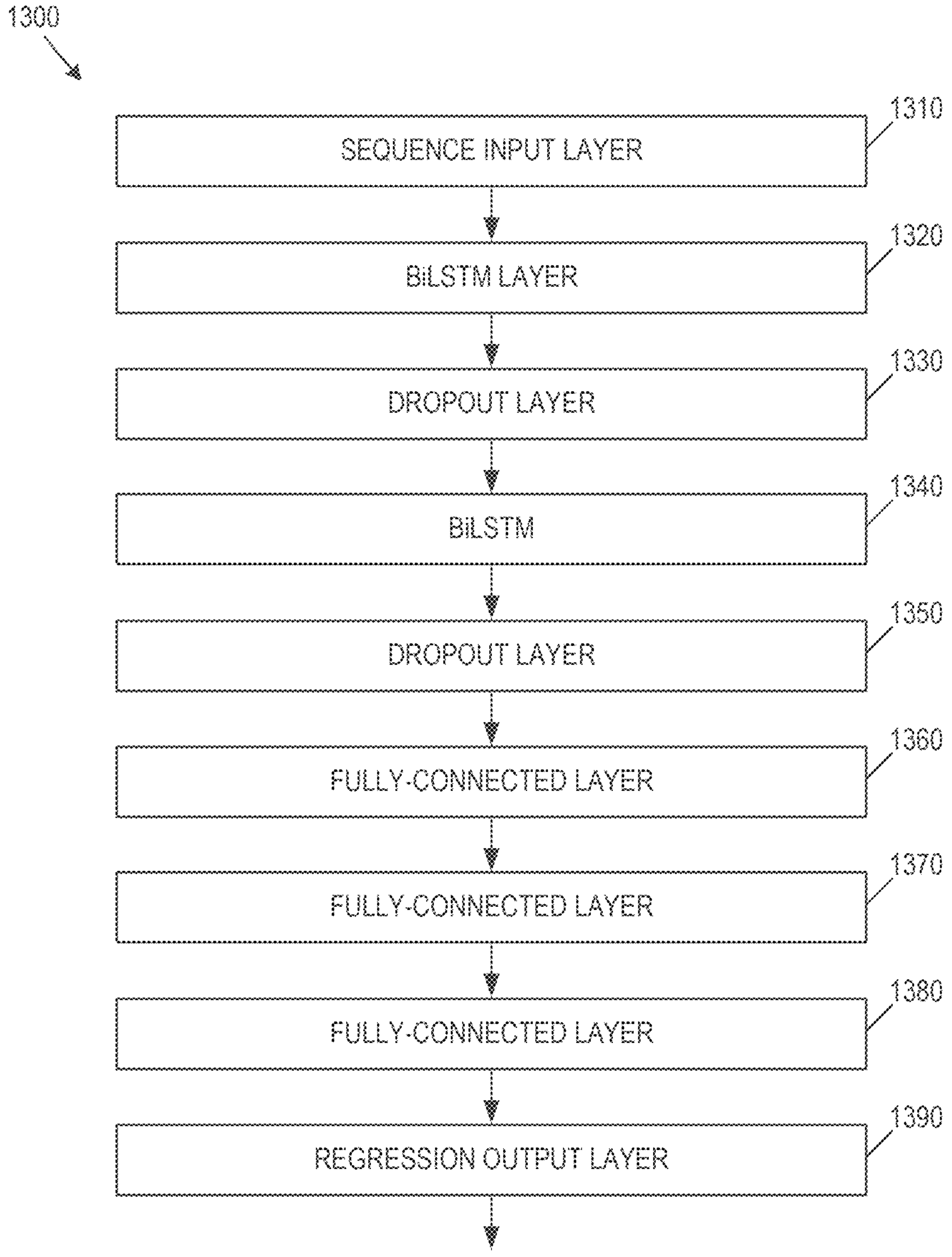
FIG. 13 is a block diagram of an example neural network model that may be used with the method of FIG. 12.

FIG. 13 illustrates an example of a recurrent neural network 1300. Recurrent neural network 1300 is an example of a machine learning model that may be trained to predict ground reaction force data, e.g. at step 1240 of method 1200. The neural network 1300 is an example of a single machine learning model configured to output multiple ground reaction force components (in the example illustrated, vertical ground reaction force signals and anterior-posterior ground reaction force signals).

Neural network 1300 includes an input layer 1310. The input layer 1310 may be configured as a sequence input layer. The input layer 1310 can be configured to receive the inputs to the machine learning model, such as the force sensor data from 1210 and the user mass, user speed and user slope from 1230.

The input layer 1310 can be configured to receive a different number or type of inputs depending on the particular configuration, and training, of the neural network model 1300. For instance, the input layer 1310 can be configured to receive 8 separate inputs (user mass, user speed and user slope, and five region-specific force values corresponding to force sensor data for 5 specified foot regions).

The input layer 1310 is connected to a first bidirectional long short-term memory (BiLSTM) layer 1320. The BILSTM layer 1320 can be defined to provide recurrent functionality to enable the model 1300 to learn from input data from prior time steps.

The BILSTM layer 1320 can be configured with a varied number of nodes or neurons. For example, the BILSTM layer 1320 may have 400 nodes, although greater or fewer nodes may be used in different implementations of network 1300.

The BiLSTM layer 1320 is connected to a first dropout layer 1330. The first dropout layer 1330 can be configured to prevent model overfitting. This may support generalization of the model to testing data.

Various different levels of dropout may be used by the first dropout layer 1330. For instance, a dropout of about 30% may be used in some implementations.

The first dropout layer 1330 is connected to a second bidirectional long short-term memory (BILSTM) layer 1340. As with BILSTM layer 1320, the second BiLSTM layer 1340 can be defined to provide recurrent functionality to enable the model 1300 to learn from input data from prior time steps.

The second BiLSTM layer 1340 can also be configured with a varied number of nodes or neurons. For example, the BILSTM layer 1340 may have 200 nodes, although greater or fewer nodes may be used in different implementations of network 1300.

The second BiLSTM layer 1340 is connected to a second dropout layer 1350. The second dropout layer 1350 can be configured to prevent model overfitting. This may further support generalization of the model to testing data.

Various different levels of dropout may be used by the second dropout layer 1350. For instance, a dropout of about 20% may be used in some implementations.

The second dropout layer 1350 is connected to a first fully-connected layer 1360. Each fully-connected layer generally operates as a feed-forward neural network in which all inputs from the previous layers are considered. In the example illustrated, the first fully-connected layer 1360 includes a hyperbolic tangent as an activation function.

The first fully-connected layer 1360 can be configured with a varied number of nodes or neurons. For example, the first fully-connected layer 1360 may have 300 nodes, although greater or fewer nodes may be used in different implementations of network 1300.

The first fully-connected layer 1360 is connected to a second fully-connected layer 1370. In the example illustrated, the second fully-connected layer 1370 also includes a hyperbolic tangent as an activation function.

The second fully-connected layer 1370 can be configured with a varied number of nodes or neurons. For example, the second fully-connected layer 1370 may have 150 nodes, although greater or fewer nodes may be used in different implementations of network 1300.

The second fully-connected layer 1370 is connected to a third fully-connected layer 1380. The third fully-connected layer 1380 can be configured with a varied number of nodes or neurons. For example, the third fully-connected layer 1380 may have 2 nodes, although greater or fewer nodes may be used in different implementations of network 1300. The number of nodes in the third fully-connected layer 1380 may vary depending on the number of outputs being generated by the model 1300.

The third fully-connected layer 1380 is connected to a regression output layer 1390. The regression output layer 1390 can be configured to implement optimization of the neural network 1300. The regression output layer can include a number of outputs based on the number of variable that the model is trained to generate. For example, the regression output layer can include two outputs (e.g. corresponding to a vertical ground reaction force signal and an anterior-posterior ground rection force signal).

In the example illustrated, recurrent neural network 1300 includes nine layers 1310-1390. However, it should be understood that a greater or fewer number of layers may be used to provide the recurrent neural network. Additionally, some of the layers 1310-1390 may be modified or substituted (e.g. replacing a dropout layer with a further fully-connected layer or with a dilution layer). Furthermore, the number of nodes within a given layer can be varied in different implementations of the neural network model.

Alternatively, a different type of machine learning model (including linear machine learning models) could be used to determine the ground reaction force data, such as, for example a support vector machine, a gradient boosted decision tree, a regression model and so on.

The machine learning model can be trained using training data that includes the set of inputs (e.g. user speed training data, and user slope training data, and force sensor training data) determined from sensor data along with user mass training data representing the mass of the user generating the corresponding training data.

The training data can also include measured data representing the force output by a user. For example, ground reaction force measurement training data may be measured using a force-instrumented treadmill that includes force plates usable to directly measure the ground reaction force data. The treadmill also allows the running speed and slope to be known from the operating settings of the treadmill while the training data is collected. The force sensor data and ground reaction force measurement training data can be measured concurrently while a user is performing an activity.

The training data can be collected from one or more users performing an activity. Once the machine learning model is trained using the training data, the machine learning model can be applied to determine the ground reaction force data of the same or different users performing the same or different activities.

The training process may vary depending on the type of machine learning model being implemented. For example, with a neural network model, an optimization algorithm can be applied to optimize the connection weights between the neurons and between layers of the neural network model. The optimization algorithm may employ a cost function based on the difference between the desired outputs (as determined by the force plates) and the predicted data output by model based on the given inputs. The neural network can be trained to minimize the cost function. The force sensor training data, the user mass training data, the user speed training data, and the user slope training data to the neural network to cause the neural network to output predicted ground reaction force data. The predicted data can then be compared to the measured ground reaction force data (determined from the ground reaction force measurement training data) using the cost function.

For example, the neural network can be a recurrent neural network. As shown in the example of FIG. 13, the final layer of the recurrent neural network can be a regression output layer. Training the neural network to minimize the cost function can be performed by optimizing the regression output layer. For instance, the regression output layer can be optimized to minimize a mean square error of the difference between the desired output data (the ground reaction force measurement training data) and the predicted data (the predicted ground reaction force data).

Various different types of optimization algorithms may be used. For example, Adam optimization may be used to optimize the regression output layer. Alternative optimization methods may also be used, such as gradient descent optimization for example.

Various different cost functions may be used. For example, the cost function may be implemented using a mean square error as described above. Alternative cost functions may also be used, such as root mean square error for example.

Once trained, the machine learning model can then be used, as at 1240, to determine the ground reaction force data based on force sensor data from the plurality of force sensors (and the IMU).

Optionally, the machine learning model may be enhanced for a user prior to being used to determine the ground reaction force data. For example, the machine learning model may be initially trained using training input data (e.g. force sensor training data, user mass training data, user speed training data, and user slope training data) and ground reaction force measurement training data from a plurality of users. This initially-trained machine learning model can then be enhanced for a particular user prior to determining the ground reaction force data corresponding to force sensor data acquired from that particular user.

Enhancing the machine learning model for a user can include adjusting the machine learning model to minimize a training error value for data measured from the particular user. For example, concurrent user-specific force sensor training data and user-specific ground reaction force measurement training data can be obtained for the particular user. The concurrent user-specific force sensor training data and user-specific ground reaction force measurement training data for the particular user may be referred to as user-specific adjusted training data.

The user-specific ground reaction force measurement training data may be obtained for the particular user in generally the same manner as the ground reaction force measurement data acquired for other users. For instance, the user-specific ground reaction force measurement training data may be obtained using a high-fidelity force measurement system, such as a force-instrumented treadmill, bathmat or flooring that includes one or more force plates or force mats. For example, the user-specific adjusted training data may be acquired during an initial calibration session where the particular user visits a testing facility (e.g. a laboratory or retail store). Optionally, the number of strides in the user-specific adjusted training data may be much less than the training data acquired for each user used to initially train the machine learning model.

The concurrent user-specific force sensor training data and user-specific ground reaction force measurement training data can then be used to re-train the machine learning model. The user-specific force sensor training data, the user-specific mass training data, the user-specific speed training data, and the user-specific slope training data can be input to the neural network to cause the neural network to output user-specific predicted data. This user-specific predicted data can be compared to user-specific desired output data (e.g. measured ground reaction force data determined from the user-specific ground reaction force measurement training data) to determine an error or cost function for the machine learning model. The machine learning model can be re-trained to minimize the cost function determined based on a user-specific difference between the user-specific desired output data and the user-specific predicted data. The machine learning model may be re-trained using the user-specific predicted data and the user-specific desired output data in addition to the predicted data and the measured ground reaction force data for the plurality of users that were used to initially train the machine learning model.

Enhancing the machine learning model for a particular user can provide improved accuracy in measurements for that user. This may be particularly advantageous for users with atypical or unique running styles that differ from the average running style of the users whose training data was used to initially train the machine learning model.

Different combinations of input data may be used to train (and optionally enhance) and implement the machine learning model. For example, the machine learning model may be trained to receive eight (8) inputs, namely a user mass value, a slope value, a running speed value, and five force values (e.g. one for each foot region).

The force values may be determined based on aggregate force data for the corresponding foot contact period. The sensor readings obtained at 1210 may include corresponding force sensor values from each of the force sensors in the plurality of force sensors.

The aggregate force data may be determined based on the sensor values received from multiple force sensors in the plurality of force sensors over the foot contact period. The aggregate force data may be determined based on the sensor values from all of the force sensors in the plurality of force sensors. Thus, a single corresponding aggregate force value may be determined for the entire sensor array.

Alternatively, the aggregate force data can be separated into a plurality of foot regions 220 (see e.g. FIG. 2). Each force sensor 106 in the plurality of force sensors can be assigned to a corresponding foot region 220. The aggregate force data for each foot region 220 can then be determined based on the sensor readings from the force sensors 106 corresponding to that foot region 220 (a region-specific set of sensor readings). For each specified foot region, the corresponding force value(s) can be provided in a region-specific force value dataset. Each region-specific force value dataset can be provided to the neural network as a separate input.

The sensor unit can be separated into a plurality of foot regions in various different ways. In the example shown in FIG. 2, the sensing unit 200 has been separated into five different foot regions 220*a*-220*e* in the anterior-posterior direction. However, the number and configuration of foot regions can vary.

The force sensor data can be obtained as continuous-time force sensor data over the first time period. Accordingly, the sensor readings may include a plurality of corresponding force sensor values from each of the force sensors in the plurality of force sensors at various time points throughout the time period (e.g. as time-continuous sensor readings or sensor readings at discrete time steps). The force values provided to the machine learning model can also include separate force values for each time step throughout the time period. Alternatively, a single force value may be provided to the machine learning model for the foot contact period. For instance, a mean force value or peak force value may be determined for the entire foot contact period.

In some cases, the inputs may be determined as a single value for each stride. For instance, a single slope and a single running speed can be determined for a given stride. The slope value may be determined as an average slope for that stride. The running speed may be determined as the average running speed for that stride. Optionally, a single slope value and/or single running speed value may be determined for multiple strides (e.g. as an average slope or average running speed).

In some cases, the inputs may include multiple values for each stride. For instance, inputs may be determined as time-continuous inputs that include multiple values at each time point or time step in a given stride. For instance, force sensor values may be determined as time-continuous inputs.

Alternatively, a different number of inputs may be used. For example, a different number of inputs may be used when the foot is segmented into a different number of regions 220. Alternatively or in addition, a different number of inputs can be used where additional inputs (e.g. user foot strike type) are included in addition to the example inputs described herein above. For instance, the user foot strike type may be used as an input that is defined based on the type of foot strike that the user performs while running.

As another example, the foot being evaluated (e.g. left foot vs. right foot) may be provided as an input. This may be particularly useful in implementations in which the ground reaction force data includes medial-lateral ground reaction force values.

Alternatively or in addition, some of the inputs may be adjusted or modified. For example, force values may be provided for only a subset of the foot-specific regions (e.g. including plantar force values in place of the whole foot force values).

At 1250, the ground reaction force data determined at 1240 can be output. For instance, the corresponding vertical ground reaction force signal and the corresponding anterior-posterior ground reaction force signal for each foot contact period can be output. This may provide a user with data representing the force applied by their foot when performing an activity like running or gaming for example. The output data can provide the user with insight into their level of performance while performing movement or an activity.

The ground reaction force data may be outputs (i.e. an output dataset) of the system. The outputs can be output directly through an output device to provide a user with feedback on the activity being monitored. For example, the outputs may be transmitted to a mobile application on the user's mobile device (e.g. a processing device 108). Alternatively or in addition, the outputs may be stored, e.g. for later review, comparison, analysis, or monitoring.

The outputs can be used as an input to a game. In particular, the outputs may correspond to a certain foot gesture, and foot gestures may be used to control the game (like buttons on a game controller). In particular, gestures performed in real life may be recreated in a game. For example, the vertical ground reaction force data that corresponds to a user running in real life may cause an avatar to run the same way in a game. Alternatively, gestures may not be recreated in a game, but may be used to execute controls in a game. For example, a step by a user in real life may serve to select an option in a game menu.

Gestures and outputs and their corresponding actions may be pre-programmed into a game or may be programmed by users. For example, the game may have a preprogrammed step gesture on the left foot that corresponds to an action in the game (e.g. selecting an option in a menu). However, in some cases, not all users are able to perform a step with their left foot (e.g. a user with no left foot). Instead, the user may be able to program their own foot gesture for the selection tool. The user may record another action (e.g. a step with the right foot with a lower vertical ground reaction force (vGRF)) that replaces the preprogrammed gesture).

Virtual environments, objects, and avatars may be generated, with which a user using the system can interact. The virtual environment and virtual objects can be altered based on the movements, gestures, and the outputs of users. Output devices (e.g. a television screen, a virtual reality headset, etc.) may be used to display the virtual environment to users. A user may visit a variety of virtual environments, including imaginary environments or environments that replicate real-life environments (e.g. Central Park, a friend's house, etc.). When a user moves around while wearing the carrier unit, they will move around in and interact with the virtual environment accordingly.

A gaming scaling factor may be applied to outputs in a game. The gaming scaling factor may be an integer (e.g. 1, 2, 5, 10, etc.) or it may not be an integer (e.g. 0.2, 1.5, 2.6, 6.9, etc.). In one example, the gaming scaling factor may be 1. In this case, the outputs are applied equivalently in a game (i.e. a 1:1 scaling). For example, the vertical ground reaction force applied to the ground when an avatar stamps their foot in a game is equivalent to the vertical ground reaction force a user exerts on the ground in real life. In another example, the gaming scaling factor may be 5. In this case, outputs are scaled 1:5 from real life to the game. In this case, the vertical ground reaction force applied to the ground when an avatar stamps their foot in a game is five times the vertical ground reaction force that a user applies to the ground in real life. Gaming experiences that are directly based on a user's outputs allow users to have a more realistic and immersive gaming experience than games that are not based on a user's biometrics (e.g. games played with buttons on a controller). Output scaling may allow for superhuman performance enhancements in a game. For example, an avatar whose vertical ground reaction force is scaled by a gaming scaling factor of 5 may be able to break through a glass floor when they stamp their foot in a game, but an avatar whose vertical ground reaction force is scaled by a gaming scaling factor of 1 may not be able to break through it. Different gaming scaling factors may also be applied to different outputs. For example, a gaming scaling factor of 2 may be applied to the vertical ground reaction force, but a gaming scaling factor of 0.5 may be applied to the anterior-posterior ground reaction force.

The outputs may also be applied to different environmental factors in a game. For example, the gravity in a game can be changed. The gravity can be changed to that of another planet, such as the gravity of Mars. The outputs can be applied to the new environmental factors, so a user can understand how they might perform in a different environment. The performance of the user under the original conditions and the simulated conditions can be shown on a visual display.

The virtual environment can display or generate an avatar representing the portion of a user's body to which the carrier unit is affixed. For example, if the carrier unit is a pair of insoles, a user's feet may be rendered in the virtual environment. The skins and/or shoes applied to the feet in the virtual environment may depend on the user's outputs, or they may be selected by the user. For example, if a user's outputs indicate that they are performing a leisurely task, they may be depicted wearing flip flops in the game environment. As another example, if the user's outputs indicate that they are running, they may be depicted wearing sneakers in the game environment. Special objects and/or abilities may be associated with the virtual skins and shoes. For example, virtual lasers or swords may extend from the virtual shoes that can be used to fight villains in a game. As another example, virtual shoes may contain a special feature, where they can build up energy if a user performs a certain task or reaches certain goals. The built-up energy can be used to create a burst of power in a game, such as a running game.

Alternatively, the virtual environment can display or generate an avatar for the user's entire body. The appearance of the avatar's body may depend on the user's outputs. For example, if large vertical ground reaction forces are frequently recorded for a user, it may be inferred that they regularly perform high-intensity physical activities such as running, and their avatar may appear lean. An avatar's appearance may also be location dependent. For example, if a user lives in a warm, dry climate, the avatar may be depicted in shorts and a t-shirt, with dried sand on their skin. Alternatively, if a user lives in the Arctic, their avatar may be depicted in a parka and furry boots. There may be location-dependent virtual items that can be unlocked. For example, if a user travels to another country in real life, they may unlock a special running shoe from that country. The carrier unit may contain a GPS system or another location-sensing system to enable the location-dependent items and features to be unlocked.

The outputs may also be used to model the dynamics of virtual objects and/or surroundings within a game. For example, if an avatar jumps on a trampoline in a game, the deflection of the trampoline in the game and the jump height of the avatar will be affected by the vertical ground reaction force applied to the ground by a user jumping in real life. The appearance of the surroundings will change based on the avatar's jump height (e.g. the higher the avatar jumps, the more sky (and less ground) that will be shown in the surroundings).

Additionally, the outputs may be used to control a character in a lifestyle game. These games may require a user to virtually embody a certain lifestyle and complete tasks involved with the lifestyle. For example, a user may embody the lifestyle of an Olympic runner in a game. The user will be required to train like an athlete, and the outputs can be used to determine if the user has successfully completed the training. They may also be required to complete other tasks relating to the lifestyle of an Olympic athlete, such as taking rest days, taking part in competitions, achieving sponsorships, going on press tours, going grocery shopping, etc.

The system may also contain safety features to prevent users from injuring themselves on their real life surroundings while gaming. Safety features may be especially important for gaming with virtual reality headsets, where vision is obstructed. One safety feature that may be included in the carrier unit is sensors and/or software that can detect potential or recent collisions of a user with surrounding objects. In response to a detected collision, the system may pause the game to check on the user using a pop-up window. For example, wherein the carrier unit is an insole, software for the Bluetooth system may detect if a user's pair of insoles is in close proximity to another user's pair of insoles. The system may alert the users that they are getting too close to each other and are at risk of a person-to-person collision. In a further example, the system may have a feature where users can measure out a safe playing area. The safe playing area is a real life zone in which a user may safely participate in a game, without risk of collision with surrounding objects. Before a gaming session starts, a user may be asked to walk around the safe playing area, which is recorded in the system. While playing the game, the user may receive feedback and alerts on where they are within the safe playing area. The user's position in the safe playing area may be shown on a visual display on the output or processing device and/or they may receive auditory alerts, visual alerts, tactile alerts, or some combination thereof to indicate they are getting close to or have gone past the edge of the safe playing area.

The system may be paired with other carrier devices in gaming scenarios. For example, the insoles may be paired with other wearable devices, such as wrist-worn IMUs. A gaming platform comprising multiple wearable game controllers at different locations on the body can encourage users to engage with a game using their full body, which may increase their workout and fitness during a game. The system may also be paired with fitness equipment. For example, the insoles can be paired with a treadmill for a running game. The incline of the treadmill can change in response to different virtual terrains (e.g. running up a virtual mountain), and the user's outputs, as determined from the insoles, can determine how they are performing in the game. Visual display carrier units, such as VR headsets, smart glasses, and smart goggles, may also be paired with the insoles to increase the immersivity of games.

The system may also contain additional sensor types, whose data can be used to augment gaming experiences. In particular, temperature sensors may provide various advantages for health, athletic, and gaming applications. The system may include one or more temperature sensors used to measure body or environmental temperature. In a first example, one or more temperature sensors (e.g. thermistors) may be included in a flexible printed circuit within the bulk of the insole. The one or more temperature sensors can detect temperature changes from the body. The temperature changes may be used in an algorithm that adjusts other sensor (e.g. force sensor) readings to account for temperature drift. Alternatively, the one or more temperature sensors may be used to measure the body temperature of users for health and gaming calculations (e.g. calorie burn calculations or task readiness calculations). In another example, the one or more temperature sensors may be affixed to the outside of the shoe or at other locations away from a user's body to determine the external temperature. The external temperature may be used in gaming to send safety messages and notifications to users (e.g. if the external temperature is hot, a user may receive a notification suggesting they hydrate more frequently). The external temperature may also be used to adjust health and gaming calculations and may be used to adjust the virtual environment in a game (e.g. if the external temperature is hot, the game may place the user in a virtual desert).

Additionally, the outputs may contribute to scoring in a game. For example, a performance score may be calculated from the outputs. If a user's outputs indicate that they are regularly exercising or increasing their exercise load and/or intensity, the number of points they earn in a game may increase. Increased points earning may incentivize users to increase their physical activity and improve their technique during gaming. The outputs may be stored, e.g. for later review, comparison with other users, analysis, or monitoring.

One or more normalization factors may be defined to allow performance scores to be determined fairly for different users. Normalization factors may be applied to account for factors such as mass, weight, age, gender, natural athletic ability, game skill, other physical characteristics, or some combination thereof.

For example, wherein the carrier unit is an insole containing force sensors, vertical ground reaction forces will be larger for heavier users than lighter users, as heavier users will naturally apply more force to the ground. However, normalization factors allow users of different sizes to obtain the same performance scores for performing equivalent activities.

The calculation of performance scores can also include modification factors such as multipliers and bonuses for successful completion of objectives including streaks, skillful movement combinations, and/or other unique game experiences such that performing the same in-game action may not yield the same performance scores each time.

The performance scores and/or outputs may also be used as metrics for zone training. Zone training is a type of athletic training which encourages users to keep their metrics within a range or "zone" of values over a predetermined period of time (e.g. the length of a game). Users may be shown their position in a zone in real-time and may be rewarded for staying within the zone and/or penalized for leaving the zone. For example, a user may be given a ground reaction force symmetry zone to stay within for a running game. During the game, the user will be encouraged to keep their ground reaction force symmetry in the designated zone to achieve maximum points.

The performance scores and/or the outputs can also be used to determine other gaming-related metrics for a user. For example, a user can be associated with one or more user levels. The user levels generally refer to the experience of a user within a game. User levels may be used to compare users to one another, or to establish progression in fitness and experience over time.

The performance scores and/or the outputs may also be used to assign and to track progress towards training goals within a predetermined time period. For example, based on a user's performance score over one week, a training goal can be generated for the user to achieve the same or a greater performance score the subsequent week. The performance scores can then be tracked the subsequent week to determine the user's percentage of progress towards achieving the training goal.

Training goals can relate to accumulated performance scores, system usage metrics and/or user outputs that should be achieved in a predetermined time period (session, day, week, month, year, season, etc.) or instantaneous values (i.e. a rate) that should be achieved at a certain point in time. Training goals may be suggested by the processing system based on previous activities, be chosen by the user, or be presented as part of a challenge from another user or group of users. Suggested training goals can become increasingly targeted for users as additional sensor data is collected by the system over time.

Training goals can be directed toward weight loss. Wherein the carrier unit is an insole containing force sensors, body weight or mass can be measured by the insoles. Alternatively, an external device may be used to measure body weight or mass and transmit the values to the input device 102, remote processing device 108, or cloud server 110. If a user has a training goal to lose a certain amount of weight, the processing system may recommend certain activities to help them accomplish their goal. In particular, the processing system may recommend fitness-related games that can be played with the carrier unit. For example, for an overweight user, the system may suggest low impact, high calorie burning games. The system may create a fitness-based game schedule for the user to follow, to encourage increased activity and intensity as the user's body weight or mass decreases (i.e. as their percentage of progress towards achieving the training goal increases). The system may also include a digital coach to help the user in their weight loss journey. A user may participate in virtual weight loss groups and/or rooms to encourage participation and support through interacting with other users with similar training goals. Weight loss may also be encouraged through badges, virtual gifts, streaks, and other virtual achievements.

Training goals may also be directed toward education. Specific games and activities may integrate educational concepts (e.g. a jumping game that helps users learn a new language). The same social interactions and virtual achievements in the weight loss example may also apply to a user's journey with an educational goal.

Additionally, the outputs may also be used to assess a user's technique when performing an activity or movement (i.e. their quality of movement). Wherein the carrier unit is an insole containing pressure or force sensors, a user's outputs may be recorded and stored in the system memory for an activity, such as running. As further data is collected for the user, the system may compare previous data against new data to determine differences in technique to notify the user of fatigue or of a potential injury. Alternatively, the system may compare data contralaterally (i.e. between opposing limbs) to determine differences in technique. To assess technique, a machine learning model may be trained on data that includes both "correct" and "incorrect" versions of an activity. In implementation, the model can then classify an activity as "correctly" or "incorrectly" performed. Alternatively, the model can be trained on data that includes rankings (e.g. by a clinician or sports scientist) on technique of certain activities (e.g. a 0 to 5 ranking, where 0 indicates that an activity was poorly executed and where 5 indicates that an activity was perfectly executed). In implementation, the system can reject exercise tasks below a certain ranking and/or output the ranked value. In another example, technique can be assessed based on conditions or restrictions set for each activity. For example, if running gait is the task being assessed, there may be a cut-off ground reaction force asymmetry used to assess movement quality (e.g. no more than 5% difference between feet). A user's outputs can be used to determine if the condition was met. If the user does not meet the condition or restriction, their technique may be deemed unacceptable.

In a further example, the outputs may also be used to determine a user's "readiness" to participate in a game or activity. At either intermediate or specified points in time, an exercise may be given to a user to assess their state of "task readiness". The exercise may include a jump, squat, balance, sprint, series of steps, or another physical exercise. The exercise may be included as part of a game or challenge or may be separate from game play. Task readiness refers to a user's ability to perform a task at a moment in time. Injury potential, technique, and/or fatigue state of the user may be incorporated in a task readiness score or may be pulled out of the task readiness score and displayed as a separate score. The task readiness, injury potential, technique, and/or fatigue state scores may be recorded over time and may be displayed in a metrics report. The metrics report may be used to quantify improvements and overall fitness. The real-time readiness scores of the user may be reported to the user on the input device 102, remote processing device 108, or cloud server 110. For example, on a display of the remote processing device, a poor task readiness score may be reported as a red bar, an average task readiness score as a yellow bar, and a good task readiness score as a green bar in the top corner of the display. The task readiness feedback may alert the user to a deteriorating quality of their movements, which can be used to make an informed decision on continuation of game play. The task readiness scores may be used to recommend games that are appropriate for the user's physical state (e.g. their fitness level) at a certain point in time. For example, consistently high task readiness scores over a period may indicate that a user should play more advanced games to improve their fitness level. The system may recommend more advanced games to the user or higher-level players to compete against. The task readiness scores may also be used to recommend rest periods for the user or to coach the user through auditory means, visual means, tactile means, or some combination thereof. For example, a virtual coach may be used to instruct the user on how to improve movement quality to gain more points, prevent injury, or achieve another goal in the game.

A virtual coach may be used to assist a user with meeting their training goals. The virtual coach may be trained through machine learning or other algorithms to give suggestions, notifications, and encouragement to the user relating to the training goal. Alternatively, a personal trainer, physiotherapist or other expert in the field may assess a user's historical outputs to develop and suggest training goals and paths to achieving training goals within the game.

Feedback may also be provided to users based on their outputs, their training goals, their task readiness, and their technique. For example, if a user goes on a run and the system calculates significant bilateral asymmetry for the vertical ground reaction force between the user's left and right foot, they may be provided with feedback to correct the asymmetry. Feedback may be provided in the form of haptic feedback, such as with vibrational motors embedded in the carrier unit.

Feedback may also be provided in the form of an audio signal. A user's outputs may be sonified and played in real time or post-activity for the user. For example, if a user goes on a run, their outputs can be sonified and played in real time. The user can then sonically identify changes in their outputs, and they can make real time adjustments to their running technique to maintain or improve their performance. Signal processing techniques may be used to increase the effects of sonification. For example, signals may be amplified, such that the sonification spans a broader range of tones than an unamplified signal, which may make it easier for users to identify changes in tone. Signals may also be layered. For example, the signals from the right and left foot may be added together prior to sonification, or the sonifications from the right and left foot may be played simultaneously. Signals may also be filtered to minimize noise, which may be distracting to a user once the signal is sonified. Visual feedback may also be provided by the system.

Users may review their feedback and data (e.g visualizations, sonifications, and haptics) during or after an activity. Real-time feedback may encourage users to continue to engage with the activity at a higher level of intensity or to increase their intensity. Post-activity data reviews may encourage users to understand their activity and movement statistics to prepare for improvements in the next activity.

Sonification of the outputs may also be used for artistic purposes. For example, the data may correspond to certain musical features, such as notes, instruments, tempos, and volumes. In a particular embodiment, the anterior-posterior ground reaction force may control the volume of a track. As the anterior-posterior ground reaction force increases, the volume may increase. Users may work together to create music. For example, if two users go running, one user's sonification may create a melody and the other user's sonification may create a harmony. In this regard, users can generate music in real time with their bodies. Similarly, users, such as DJs, may be able to mix music in real time. For example, a DJ may run on a treadmill at a concert while wearing the insoles, and by changing their running technique, they can cue tracks and increase or decrease the speed of tracks.

The outputs may also be used to create visualizations. Visualizations may be data driven (e.g. graphs) or artistic visuals (e.g. data-inspired paintings). For example, a user may be able to "paint" with their insoles by applying force in various areas of the foot and using foot gestures to create different "brush strokes". In another example, a large display screen may be used to show a user's outputs while they are running, racing, or gaming.

Additionally, information may be communicated to and/or between users through visual, audio, or haptic cues. For example, the system may send a haptic cue to a user's insoles to prompt them to complete a daily challenge based on the outputs. The results of their daily challenges may be compared with the results of other users. Alternatively, if cues are sent between users, a first user in a game may challenge a second user in a game to perform an activity by sending a haptic signal to the second user's carrier device. The communicated information may be based upon the two users' outputs. For example, the first user may send a haptic cue to the second user to challenge them to a run, where the user with the best vertical ground reaction force symmetry during the run will be declared the winner.

Users may also be able to create levels or challenges for other users based on their outputs. For example, in an impersonation game, a first user may be challenged to recreate the walk of a second user (such as a friend or celebrity), by replicating their anterior-posterior ground reaction force over one stride.

The outputs may be displayed on an output device, as part of the remote processing device 108 or cloud server 110. A user may also be able to interact with a visual display via an interactive medium (e.g. a touchscreen) on the output device. Examples of data visualizations that may be provided on the visual display based on sensor readings and/or derived values of a user using the carrier unit include foot pressure maps to show the pressure distribution on the insoles, foot pressure maps to show the movement of the center of pressure, points displays (e.g. performance score), pop-up notifications of errors in movement, pop-up notifications with suggestions to correct the movement, graphs showing changes in data over time, colour codes (e.g. different colour pop-ups for different performance scores or gestures), footprints whose shapes or depths are estimated based on the sensor readings and/or derived values, cumulative displays (e.g. accumulation of peak vertical ground reaction forces, which, when a certain level is reached, may be used to provide a burst of power for an avatar in a game), or some combination thereof. The data visualizations may be altered or enabled or disabled by users, with toggles, buttons, or other actions.

A user's output device may also display information (such as names, outputs, etc.) of other users in the same area using the same type of system. Carrier units may contain GPS systems or other location-sensing systems to enable viewing information of other users in the same area. Location-sensing may provide opportunities for virtual social interactions between users. Examples of social interactions include gift exchanges, meet-ups in virtual rooms, messaging, game challenges, cooperative games, competitive games, combination games (i.e. games with a competitive and cooperative aspect), tournaments, leaderboards (e.g. for age groups, geographic locations, specific games, etc.), and the ability to "follow" and/or "friend" other users (i.e. adding users to a list of "friends" on the system platform). Other social interactions known in the art, but not listed here, may also be included.

Virtual meeting rooms are digital areas where users may send messages or chats with one another, play games together, and participate in social interactions with other users. The system may have virtual meeting rooms available, or users may create and design their own virtual meeting rooms. The owner of a virtual meeting room may allow open access to the virtual meeting room, or they may restrict access to certain users. The owner may invite users to join their virtual meeting room.

Social interactions may also include competitive races against the outputs of the same user (i.e. their previous scores), other users, a computer character, celebrities, and/or professionals. For example, a user may enable a "ghost" mode, where they can view their previous performances when repeating an activity, to compete against themselves. For example, in a game where a user is required to perform a running activity, they can view a "ghost" of their avatar's best performance while repeating the activity, along with a display window showing the ghost's outputs, to encourage them to match or improve the performance. In another example, in a running game, a user may enable "ghost" mode to view the outputs of a 5000 meter professional runner, who recorded their outputs in the game for other users to copy. The user can work towards matching the professional runner's data to improve their own performance. In another example, a professional runner may create a virtual competition where users can compete against the professional for a month-long running challenge. The participating users' outputs can be compared to the professional's outputs to determine if any of the users beat the professional. Users who participate in and/or win the challenge may receive a virtual reward.

The method 1200 generally describes the process of determining ground reaction force data for one leg. Optionally, method 1200 may be applied to determine the ground reaction force data for both of a user's legs, based, respectively, on data (e.g. sensor readings and IMU data) collected for each leg. Method 1200 may be performed concurrently on the data collected for each leg in order to provide a user with real-time feedback of the ground reaction force data for each leg.

EXAMPLES

An implementation of the systems and methods described herein was tested. In particular, an implementation of method 400 was tested using force sensor data acquired from users running while wearing Orpyx LogR™ insoles incorporating force sensors. Each user ran for two minutes at three speeds (16 km/h, 20 km/h, 24 km/h).

The testing was conducted while users were running on a force-instrumented treadmill configured to measure the ground reaction force applied by each user. A positive threshold crossing value of 20N was used to identify foot-contact times based on the data from the force-instrumented treadmill. A negative threshold crossing value of 20N was used to identify foot-off times based on the data from the force-instrumented treadmill.

The implementation of method 400 was tested against seven other methods for detecting foot-contact and foot-off using the insole sensor data. The results from each method were compared against the foot-contact and foot-off times detected from the force-instrumented treadmill data.

Figure 14A:
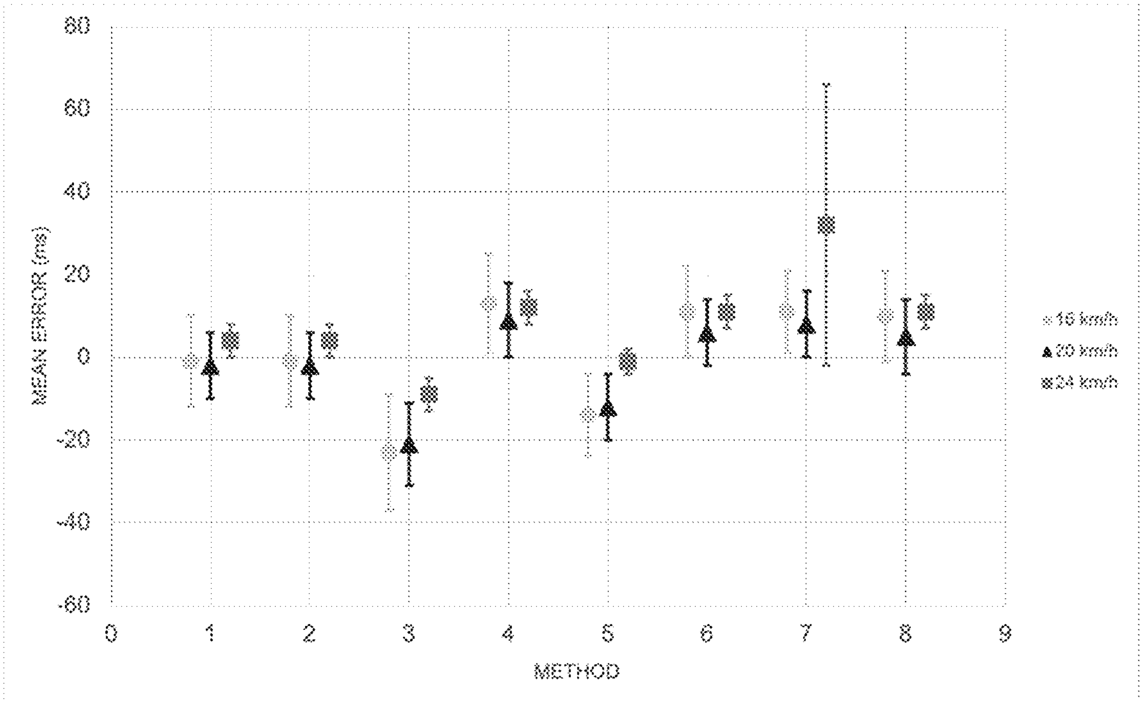
FIG. 14A is a plot illustrating the mean error of identifying a foot-contact time using various different techniques including an example implementation of the method shown in FIG. 4.

FIG. 14A shows a plot of the mean error and standard deviation of detecting foot-contact for all eight methods tested. In FIG. 14A, the mean error and standard deviation for the implementation of method 400 is shown as method 8 along the x-axis. The standard deviations (as shown by the vertical bars extending from the mean error points) illustrate the 0.95 confidence interval.

As shown in FIG. 14A, the implementation of method 400 shows fairly consistent results in detecting foot contact at different speeds.

Figure 14B:
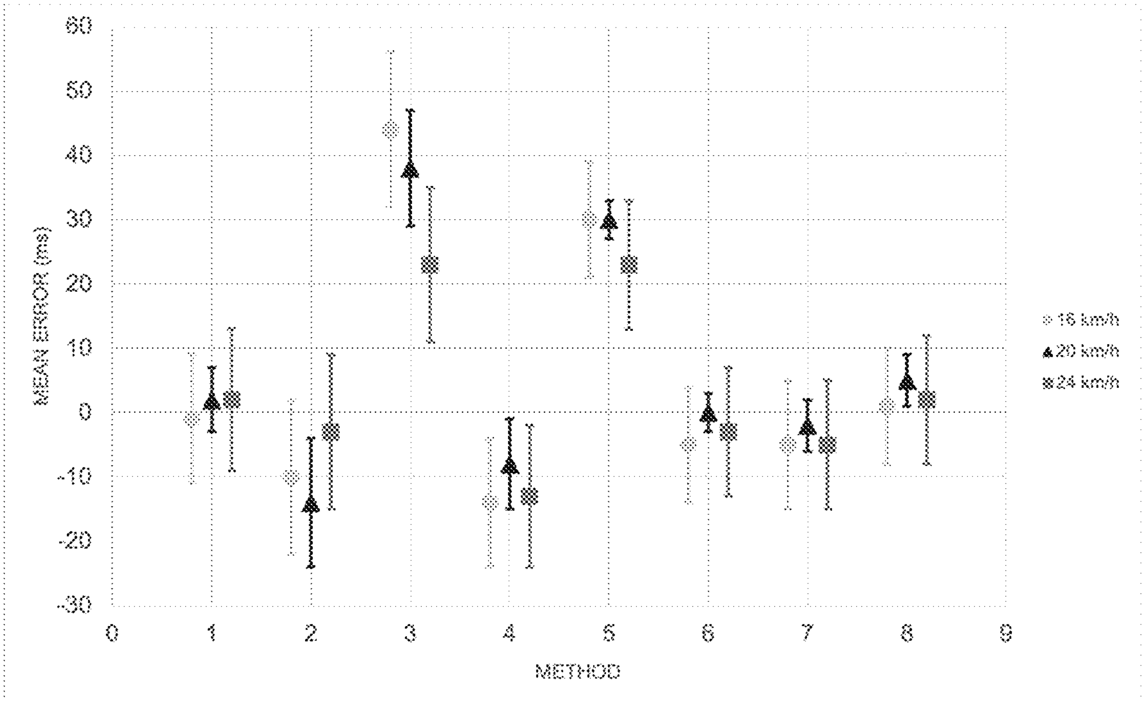
FIG. 14B is a plot illustrating the mean error of identifying a foot-off time using various different techniques including an example implementation of the method shown in FIG. 4.

FIG. 14B shows a plot of the mean error and standard deviation of detecting foot-off for all eight methods tested. In FIG. 14B, the mean error and standard deviation for the implementation of method 400 is shown as method 8 along the x-axis. The standard deviations (as shown by the vertical bars extending from the mean error points) illustrate the 0.95 confidence interval.

As shown in FIG. 14B, the implementation of method 400 shows fairly consistent results in detecting foot-off at different speeds. The mean error and standard deviation of the implementation of method 400 are also substantially consistent for detecting both foot-contact and foot-off.

An implementation of method 1000 was also tested using a plurality of force sensors and an IMU mounted in an insole and a neural network model trained to generate an IMU mean vertical ground reaction force using 4 inputs (a running speed of the user, a peak value of vertical acceleration, a peak value of fore-aft acceleration and a peak value of a sagittal plane gyroscope signal) was tested to evaluate the accuracy of determining the IMU mean vertical ground reaction force. The neural network model was trained using sensor data collected from 4 separate users, with each user taking approximately 4000 steps on a force-instrumented treadmill.

The IMU mean vertical ground reaction force determined by the tested implementation of method 1000 was compared against the mean vertical ground reaction force measured by the force-instrumented treadmill. The implementation of method 1000 and the force-instrumented treadmill were both configured to determine the mean vertical ground reaction for each stride.

Figure 15A:
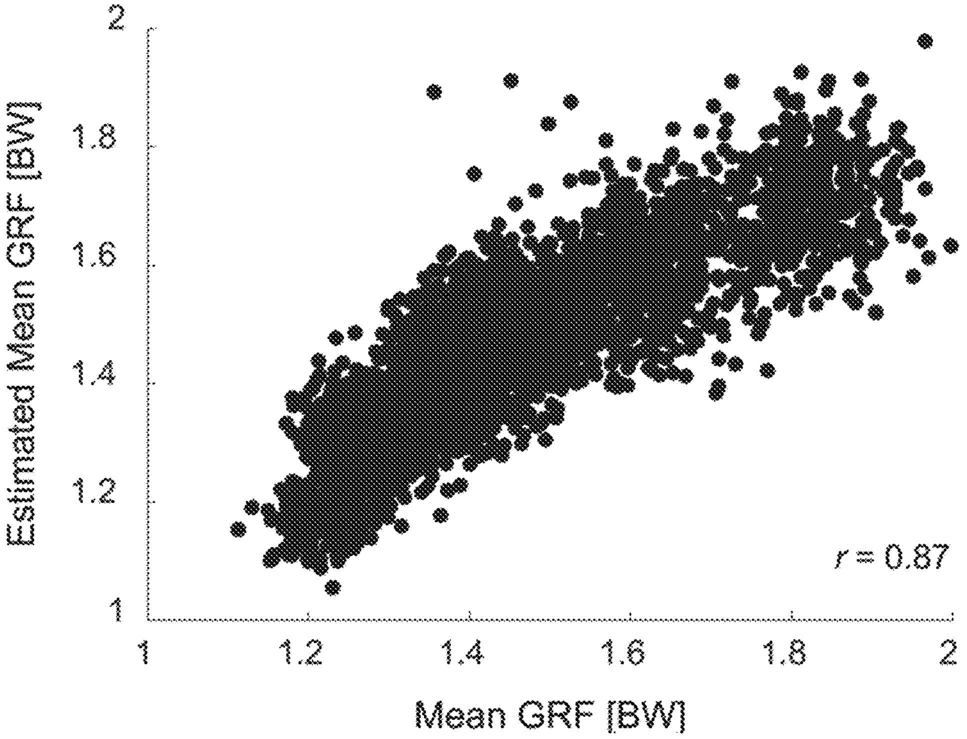
FIG. 15A is a plot illustrating an IMU mean ground reaction force determined according to an example implementation of the method shown in FIG. 10 (y-axis) and the mean ground reaction force determined using a force-instrumented treadmill (x-axis)

FIG. 15A shows a comparison of the IMU mean vertical ground reaction force as determined using the example implementation of method 1000 (y-axis) compared to the mean vertical ground reaction force determined by the force-instrumented treadmill (x-axis). The IMU mean vertical ground reaction force was determined using a neural network as described at step 1040 of method 1000. As shown in FIG. 15A, the plot shows substantially linear results with good correlation (R=0.87) indicating good accuracy in the estimated IMU mean vertical ground reaction force as determined by the example implementation of method 1000.

Figure 15B:
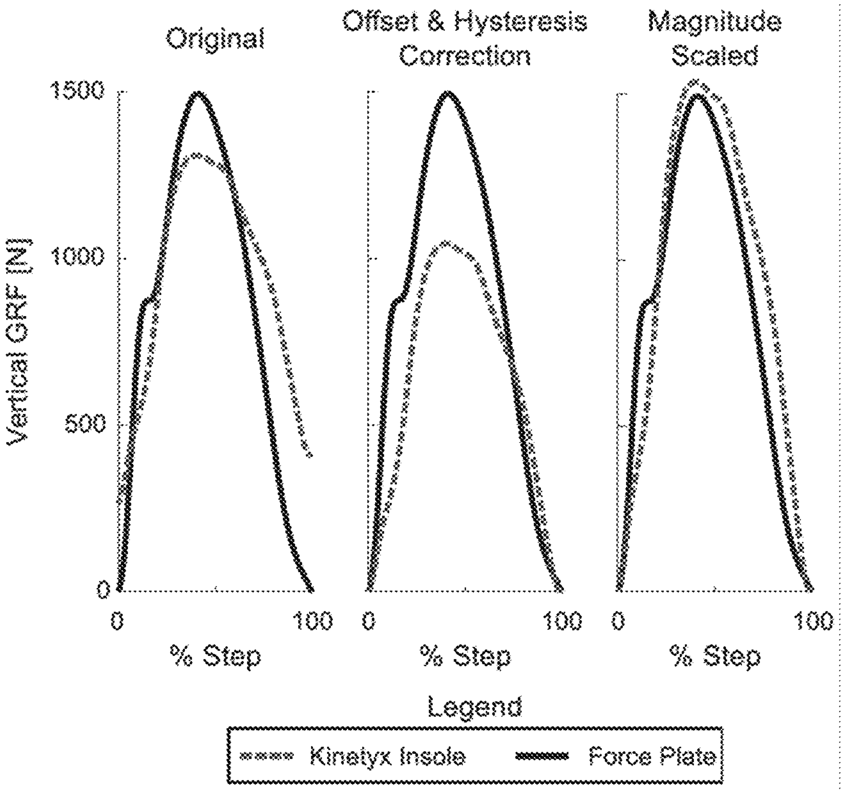
FIG. 15B is a diagram illustrating a series of plots showing an example of adjusting and scaling force signal values according to example implementations of the methods shown in FIGS. 7 and 8 and the force signal values determined using a force-instrumented treadmill.

Implementations of methods 700, 800, and 1000 were also tested using a plurality of force sensors mounted in an insole. FIG. 15B shows a series of plots providing a comparison of the force signal as determined from the force sensor data as compared to the force signal determined by the force-instrumented treadmill over the course of a foot contact period.

The left-hand plot shows the original force signal as determined from the force sensor data. The middle plot shows an adjusted and scaled force signal after applying an implementation of method 700 to account for drift offset and an implementation of method 800 to account for signal hysteresis. In the middle plot, the original force signal has been adjusted by lowering the signal to a baseline of ON. The adjusted and scaled force signal has also been stretched in the unloading portion of the foot contact period from the local maximum to the new baseline (as provided by the implementation of method 700). The right-hand plot shows a magnitude-corrected force signal after applying an implementation of method 1000 (in addition to the implementations of methods 700 and 800). As FIG. 15B illustrates, the magnitude-corrected force signal aligns more closely with the force signal determined by the force-instrumented treadmill as compared to the original force signal determined from the force sensor data.

An implementation of method 1200 was also tested using a plurality of force sensors and an IMU mounted in an insole and a neural network model trained to generate ground reaction force data include a vertical ground reaction force and an anterior-posterior ground reaction force using 8 inputs (a user mass, running speed, slope, 5 region-specific force values) to evaluate the accuracy of determining the ground reaction force data.

Sensor data was collected from 18 separate users wearing Pedar® insoles, with each user running under 11 running conditions for one minute each on a force-instrumented treadmill. The running conditions included running on level ground at running speeds of 2.6 m/s, 3.0 m/s. 3.4 m/s, and 3.8 m/s; running at an incline of +6° at 2.6 m/s, 2.8 m/s, and 3.0 m/s; and running at a decline of −6° at 2.6 m/s, 2.8 m/s, 3.0 m/s, 3.4 m/s. The mass of each user was also measured.

The method was validated using leave-one-out cross-validation, in which the model was trained with the data collected from 17 users under the various running conditions and then tested using the data collected from the 1 remaining user. This training process was repeated such that models trained using 18 different sets of training data were tested. During training, the desired outputs were defined using ground reaction force data obtained from the force-instrumented treadmill.

Figure 16:
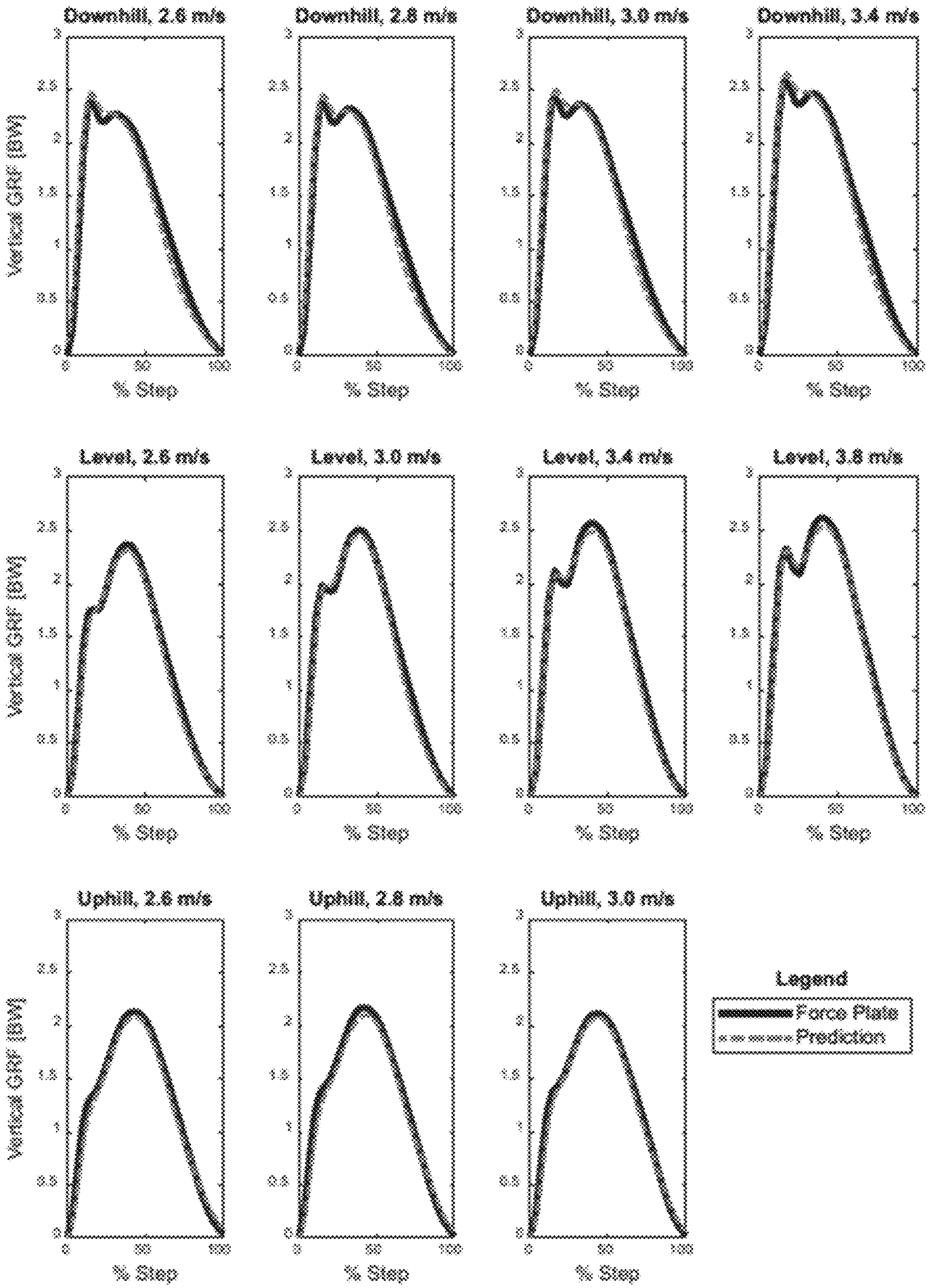
FIG. 16 is a diagram illustrating plots showing the vertical ground reaction force determined using an example implementation of the method shown in FIG. 12 (dashed line) and the vertical ground reaction force determined using a force-instrumented treadmill (solid line) for multiple users.

FIG. 16 shows eleven separate plots evaluating the determination of the vertical ground reaction force signal for each of the different running conditions for one user. Each plot shows a comparison of the vertical ground reaction force signal as determined using the example implementation of method 1200 and the vertical ground reaction force signal as determined by the force plates of the force-instrumented treadmill. It can be seen that the vertical ground reaction force values determined using the implementation of method 1200 align well with the vertical ground reaction force values measured by the force-instrumented treadmill.

Figure 17:
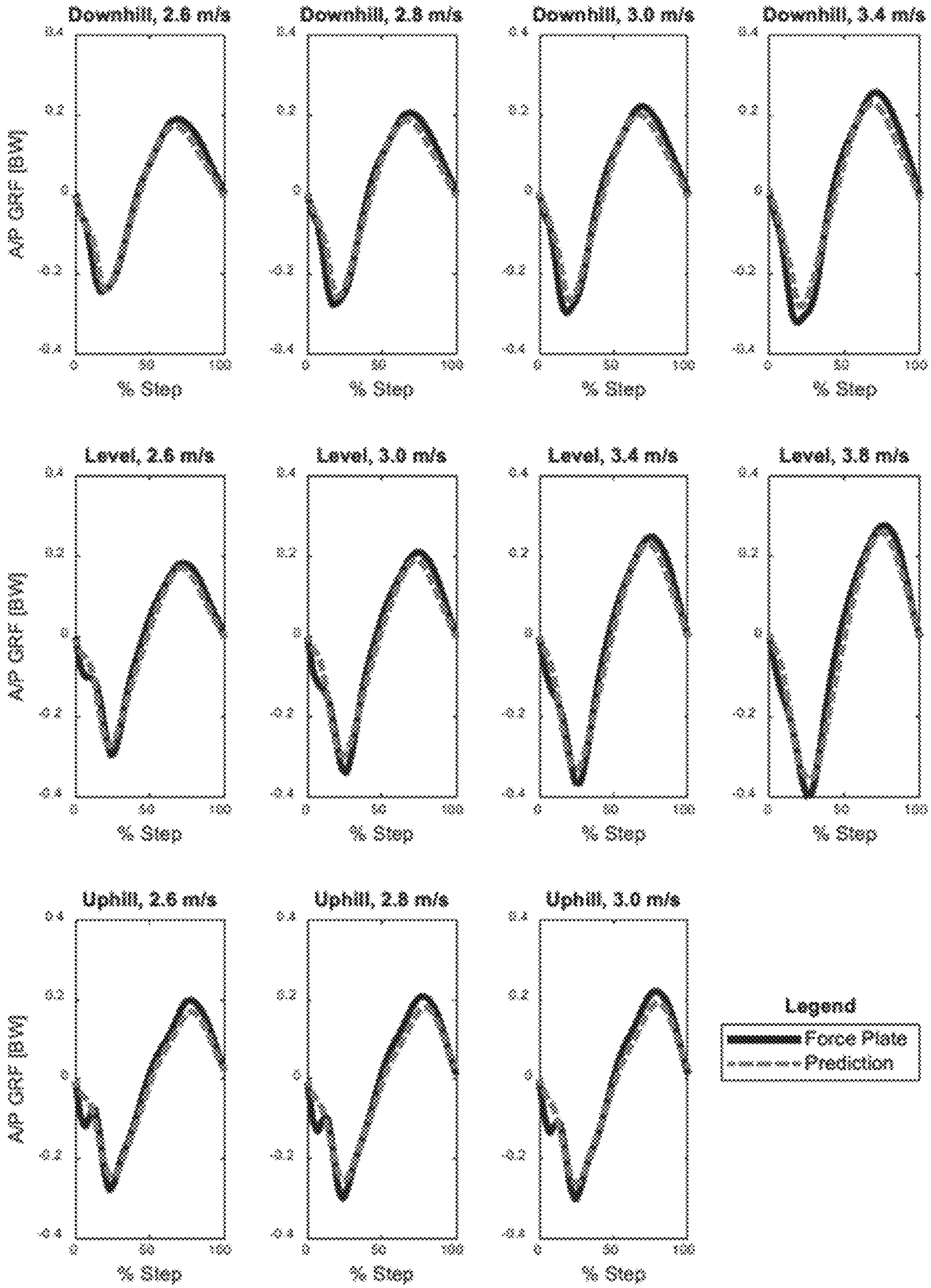
FIG. 17 is a diagram illustrating plots showing the anterior-posterior ground reaction force determined using an example implementation of the method shown in FIG. 12 (dashed line) and the anterior-posterior ground reaction force determined using a force-instrumented treadmill (solid line) for multiple users.

FIG. 17 shows eleven separate plots evaluating the determination of the anterior-posterior ground reaction force signal for each of the different running conditions for one user (the same user represented in the plots shown in FIG. 16). Each plot shows a comparison of the anterior-posterior ground reaction force signal as determined using the example implementation of method 1200 and the anterior-posterior ground reaction force signal as determined by the force plates of the force-instrumented treadmill. It can be seen that the anterior-posterior ground reaction force values determined using the implementation of method 1200 align well with the anterior-posterior ground reaction force values measured by the force-instrumented treadmill.

Tables 1-3 below show the root mean square error (in units of bodyweight) of determining ground reaction force data for all of the users across the various running conditions using the example implementation of method 1200 as compared to the ground reaction force data determined by the force plates of the force-instrumented treadmill.

Table 1 shows the root-mean square error (RMSE) of determining the vertical ground reaction force and the anterior-posterior ground reaction force for all users tested running on level ground at speeds of 2.6 m/s, 3.0 m/s. 3.4 m/s, as well as the correlation (r) of the recurrent neural network for the vertical and anterior-posterior (A/P) ground reaction force (GRF) components. All of the values in Table 1 are shown as mean values±standard deviations.

TABLE 1

| | | Level | | | |
|---|---|---|---|---|---|
| GRF | Model | 2.6 m/s | 3.0 m/s | 3.4 m/s | 3.8 m/s |
| Vertical | RMSE | 0.14 ± 0.04 | 0.15 ± 0.04 | 0.15 ± 0.05 | 0.16 ± 0.05 |
| | r | 0.99 ± 0.01 | 0.99 ± 0.01 | 0.99 ± 0.01 | 0.99 ± 0.01 |
| A/P | RMSE | 0.04 ± 0.01 | 0.05 ± 0.01 | 0.05 ± 0.02 | 0.06 ± 0.02 |
| | r | 0.98 ± 0.01 | 0.98 ± 0.01 | 0.98 ± 0.01 | 0.98 ± 0.01 |

Table 2 shows the root-mean square error of determining the vertical ground reaction force and the anterior-posterior ground reaction force for all users tested running downhill at a −6° decline at speeds of 2.6 m/s, 2.8 m/s, 3.0 m/s, 3.4 m/s as well as the correlation of the recurrent neural network for the vertical and anterior-posterior (A/P) ground reaction force (GRF) components. All of the values are shown as mean values±standard deviations.

TABLE 2

| | | 6° downhill | | | |
|---|---|---|---|---|---|
| GRF | Model | 2.6 m/s | 2.8 m/s | 3.0 m/s | 3.4 m/s |
| Vertical | RMSE | 0.15 ± 0.06 | 0.16 ± 0.06 | 0.16 ± 0.07 | 0.17 ± 0.06 |
| | r | 0.99 ± 0.01 | 0.99 ± 0.01 | 0.99 ± 0.01 | 0.99 ± 0.01 |
| A/P | RMSE | 0.05 ± 0.02 | 0.05 ± 0.02 | 0.06 ± 0.02 | 0.06 ± 0.02 |
| | r | 0.97 ± 0.02 | 0.97 ± 0.02 | 0.97 ± 0.02 | 0.98 ± 0.02 |

Table 3 shows the root-mean square error of determining the vertical ground reaction force and the anterior-posterior ground reaction force for all users tested running uphill at a +6° incline at speeds of 2.6 m/s, 2.8 m/s, and 3.0 m/s as well as the correlation of the recurrent neural network for the vertical and anterior-posterior (A/P) ground reaction force (GRF) components. All of the values are shown as mean values±standard deviations.

TABLE 3

| | | 6° Uphill | | |
|---|---|---|---|---|
| GRF | Model | 2.6 m/s | 2.8 m/s | 3.0 m/s |
| Vertical | RMSE | 0.13 ± 0.03 | 0.13 ± 0.03 | 0.14 ± 0.04 |
| | r | 0.99 ± 0.01 | 0.99 ± 0.01 | 0.99 ± 0.01 |
| A/P | RMSE | 0.04 ± 0.01 | 0.04 ± 0.01 | 0.04 ± 0.01 |
| | r | 0.98 ± 0.01 | 0.98 ± 0.01 | 0.98 ± 0.01 |

As Tables 1-3 demonstrate, the root-mean square error is consistently low for both the vertical ground reaction force (at most 0.17) and the anterior-posterior ground reaction force (at most 0.06) across all running conditions. There is also a strong correlation (at least 0.97) across all running conditions.

A further implementation of method 1200 was also tested using a plurality of force sensors and an IMU mounted in an insole and a neural network model trained to generate ground reaction force data including a vertical ground reaction force and an anterior-posterior ground reaction force using 8 inputs (a user mass, running speed, slope, 5 region-specific force values). This further implementation was tested to evaluate the accuracy of determining the ground reaction force data when the neural network model is enhanced for a particular user as compared to using a generic neural network model.

Figure 18:
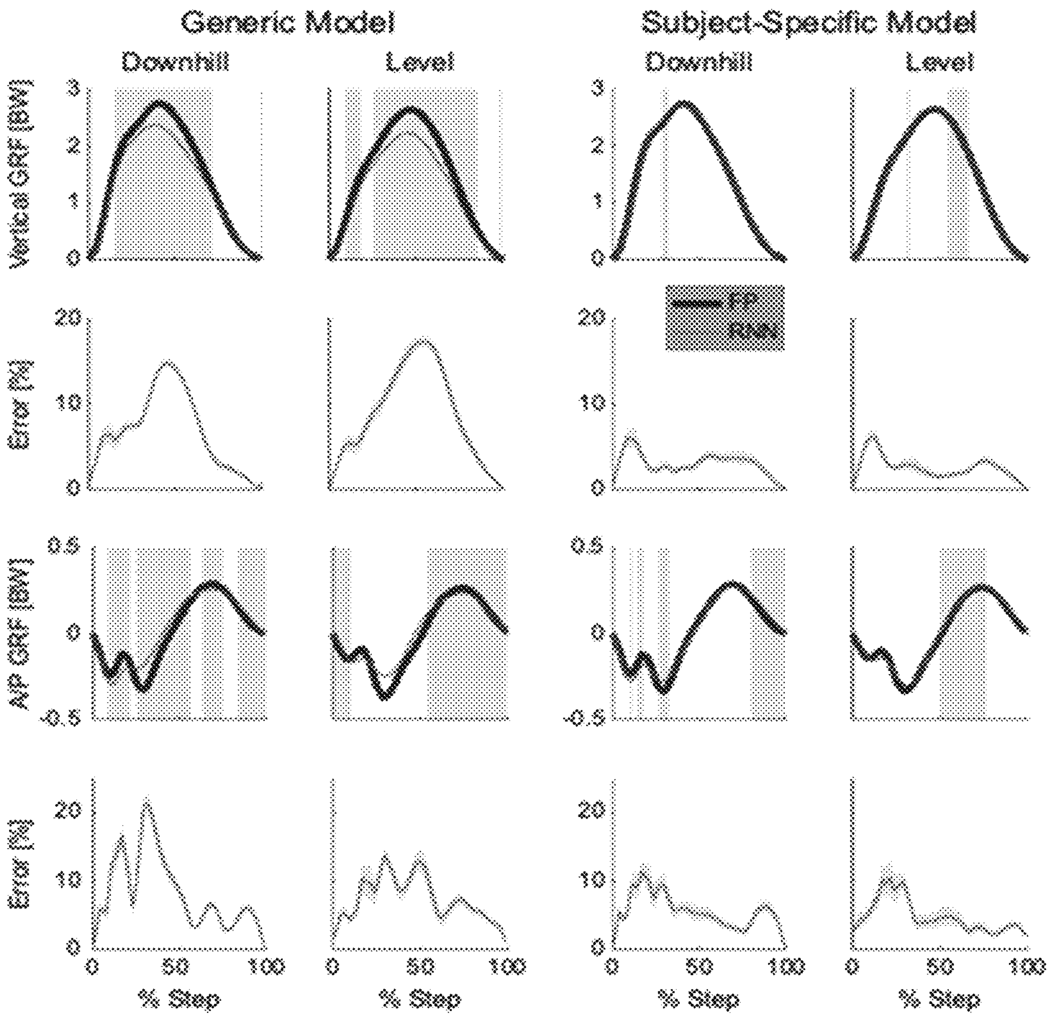
FIG. 18 is a diagram illustrating a series of plots showing the relative accuracy of ground reaction force data determined using an example implementation of the method shown in FIG. 12 with a generic model and an example implementation of the method shown in FIG. 12 with an enhanced user-specific model as compared to the ground reaction force data determined using a force-instrumented treadmill (solid line) for multiple users.

Training input data and ground reaction force measurement training data was acquired from seventeen subjects. This training input data and ground reaction force measurement training data was used to train an initial generic neural network model, in this example a recurrent neural network. A subject-specific model was then generated by enhancing the generic neural network model using a portion (approximately 10%) of the training input data and ground reaction force measurement training data from a particular subject. The portion of the training input data and ground reaction force measurement training data from the particular subject was used to re-train the generic model in order to generate the subject-specific model. The generic neural network model and subject-specific model were then applied to determine predicted ground reaction force data for the particular user while running downhill and on level ground. As shown in FIG. 18, the subject-specific model significantly improved the accuracy of the predicted ground reaction force data.

FIG. 18 shows a series of plots comparing the vertical ground reaction force signal and the anterior-posterior ground reaction force signal generated by the generic model and the subject-specific model based on sensor data acquired while the particular user was running downhill and on level (both at 3.4 m/s) terrain with the force signals generated based on force plate measurements. In addition, FIG. 18 shows plots of the percent error for the model-generated ground reaction force signals as compared to the force signals generated based on force plate measurements.

The top row in FIG. 18 shows an average of the vertical GRF from the force plate (FP) along with average recurrent neural network (RNN) predictions for the generic and subject-specific models. The shaded areas indicate signal regions where there were significant differences between the vertical GRF signal values generated by FP and RNN ($p<0.05$). As shown in FIG. 18, the subject-specific model reduced the size of the significantly different regions across all running conditions by 77% for the vertical GRF.

The second row in FIG. 18 shows the mean absolute percent error (plus/minus one standard deviation) for the generic and subject-specific models in the vertical direction.

The subject-specific model reduced the average percent error across all conditions from 7.7% to 2.9% for the vertical GRF.

The third row in FIG. 18 shows an average of the anterior/posterior (A/P) GRF from the FP along with average RNN predictions. The shaded areas indicate signal regions where there were significant differences between the anterior-posterior GRF signal values generated by FP and RNN ($p<0.05$). As shown in FIG. 18, the subject-specific model reduced the size of the significantly different regions across all running conditions by 53% for the A/P GRF.

The bottom row in FIG. 18 shows the mean absolute percent error (plus/minus one standard deviation) for the generic and subject-specific models in the A/P direction. The subject-specific model reduced the average percent error across all conditions from 8.0% to 5.2% for the A/P GRF.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A method for analyzing force sensor data from a plurality of force sensors positioned underfoot, the method comprising:

obtaining a sensor signal dataset based on sensor readings from the plurality of force sensors during a first time period, wherein the sensor signal dataset defines a series of signal values extending over the first time period;

based on the series of signal values, identifying a pair of interstride interval periods within the first time period, the pair of interstride interval periods including a foot contact interstride interval and a foot off interstride interval, wherein each interstride interval includes a subset of signal values from the series of signal values;

identifying a foot contact period by:

for each interstride interval, identifying an inflection point in the corresponding subset of signal values, wherein for each interstride interval, identifying the inflection point in the corresponding subset of signal values comprises:

identifying a threshold crossing value in the subset of signal values for that interstride interval;

dividing the interstride interval into a plurality of segments;

identifying a transition signal value in the subset of signal values for that interstride interval, wherein the transition signal value is identified at a transition point between adjacent segments in the plurality of segments;

tracing a unity line between the threshold crossing value and the transition signal value, the unity line identifying a series of unity line values within the interstride interval; and identifying the inflection point as a point of maximum difference between the unity line values and the subset of signal values;

identifying the foot contact period as a time period extending between the inflection points identified for the pair of interstride intervals;

outputting foot contact period data corresponding to the foot contact period; and generating feedback to the user, the feedback generated from an output dataset, the output dataset including the foot contact period data and/or an additional foot contact period data, the additional foot contact period data calculated based on the foot contact period data, the feedback comprising at least one of a haptic signal, an audio signal, a visual display, and an avatar.

2. The method of claim 1, further comprising computing at least one additional foot contact period data based on the foot contact period data.

3. The method of claim 1, wherein the foot contact interstride interval is identified by:

identifying a pair of subsequent positive threshold crossings in the series of signal values, wherein each positive threshold crossing is identified as a point in the first time period where the series of signal values is increasing and crosses a specified threshold value; and defining the foot contact interstride interval as a first interstride period extending between the pair of subsequent positive threshold crossings.

4. The method of claim 3, wherein the threshold crossing value for the foot contact interstride interval is identified at the second positive threshold crossing in the pair of subsequent positive threshold crossings, and wherein the transition signal value for the foot contact interstride interval is identified at the transition point at the beginning of the last segment in the plurality of segments.

5. The method of claim 3, wherein the foot off interstride interval is identified by:

identifying a pair of subsequent negative threshold crossings in the series of signal values, wherein each negative threshold crossing is identified as a location in the first time period where the series of signal values is decreasing and crosses a specified threshold value; and defining the foot off interstride interval as a second interstride period extending between the pair of subsequent negative threshold crossings.

6. The method of claim 5, wherein the threshold crossing value for the foot off interstride interval is identified at the first negative threshold crossing in the pair of subsequent negative threshold crossings, and wherein the transition signal value for the foot off interstride interval is identified at the transition point located at the end of the first segment in the plurality of segments.

7. The method of claim 5, wherein the specified threshold value is defined as 50% of the maximum signal value.

8. The method of claim 1, wherein the first time period is at least 5 seconds.

9. The method of claim 1, further comprising identifying a plurality of foot contact periods using a rolling window as the first time period.

10. The method of claim 9, further comprising:

identifying a swing phase time period that extends between a pair of adjacent foot contact periods, the pair of adjacent foot contact periods including a first foot contact period and a second foot contact period;

determining a minimum value of the signal values in the swing phase time period; and adjusting the signal values in the first foot contact period by subtracting the minimum value from each signal value in the first foot contact period.

11. The method of claim 1, wherein the foot contact period extends between a foot contact inflection point and a foot-off inflection point and the method further comprises accounting for signal hysteresis by:

identifying a local maximum signal value in the foot contact period;

identifying an unloading signal period extending between the maximum signal value and the foot-off inflection point; and scaling the signal values in the unloading signal period to span from a minimum value of the signal values in the swing phase time period to the local maximum signal value.

12. A system for analyzing force sensor data, the system comprising:

a plurality of force sensors positionable underfoot; and one or more processors communicatively coupled to the plurality of force sensors;

wherein the one or more processors are configured to:

obtain a sensor signal dataset based on sensor readings from the plurality of force sensors during a first time period, wherein the sensor signal dataset defines a series of signal values extending over the first time period;

based on the series of signal values, identify a pair of interstride interval periods within the first time period, the pair of interstride interval periods including a foot contact interstride interval and a foot off interstride interval, wherein each interstride interval includes a subset of signal values from the series of signal values;

identify a foot contact period by:

for each interstride interval, identifying an inflection point in the corresponding subset of signal values by:

identifying a threshold crossing value in the subset of signal values for that interstride interval;

dividing the interstride interval into a plurality of segments;

identifying a transition signal value in the subset of signal values for that interstride interval, wherein the transition signal value is identified at a transition point between adjacent segments in the plurality of segments;

tracing a unity line between the threshold crossing value and the transition signal value, the unity line identifying a series of unity line values within the interstride interval; and identifying the inflection point as a point of maximum difference between the unity line values and the subset of signal values;

identify the foot contact period as a time period extending between the inflection points identified for the pair of interstride intervals;

output foot contact period data corresponding to the foot contact period; and generate feedback to the user, the feedback generated from an output dataset, the output dataset including the foot contact period data and/or an additional foot contact period data, the additional foot contact period data calculated based on the foot contact period data, the feedback comprising at least one of a haptic signal, an audio signal, a visual display, and an avatar.

13. The system of claim 12, wherein the plurality of force sensors are disposed on an insole, a shoe, a compression-fit garment, or a sock.

14. The system of claim 12, wherein the one or more processors is further configured to:

compute at least one additional foot contact period data based on the foot contact period data;

output an output dataset, wherein the output dataset comprises the foot contact period data and/or the at least one additional foot contact period data; and use the output dataset as an input to a game.

15. The system of claim 14, wherein the one or more processors is further configured to generate an audio signal or a visual display based on the output dataset.

16. The system of claim 12, wherein the one or more processors are configured to identify the foot contact interstride interval by:

identifying a pair of subsequent positive threshold crossings in the series of signal values, wherein each positive threshold crossing is identified as a point in the first time period where the series of signal values is increasing and crosses a specified threshold value; and defining the foot contact interstride interval as a first interstride period extending between the pair of subsequent positive threshold crossings.

17. The system of claim 12, wherein the one or more processors are configured to identify the foot off interstride interval by:

identifying a pair of subsequent negative threshold crossings in the series of signal values, wherein each negative threshold crossing is identified as a location in the first time period where the series of signal values is decreasing and crosses a specified threshold value; and defining the foot off interstride interval as a second interstride period extending between the pair of subsequent negative threshold crossings.

18. The system of claim 12, wherein the one or more processors are further configured to filter the sensor signal dataset prior to identifying the pair of interstride intervals.

* * * * *